United States Patent
Rava et al.

(10) Patent No.: US 9,447,453 B2
(45) Date of Patent: Sep. 20, 2016

(54) RESOLVING GENOME FRACTIONS USING POLYMORPHISM COUNTS

(75) Inventors: Richard P. Rava, Redwood City, CA (US); Brian K. Rhees, Chandler, AZ (US); John P. Burke, Reno, NV (US)

(73) Assignee: Verinata Health, Inc., San Diego, CA (US)

( * ) Notice: Subject to any disclaimer, the term of this patent is extended or adjusted under 35 U.S.C. 154(b) by 10 days.

(21) Appl. No.: 13/445,778

(22) Filed: Apr. 12, 2012

(65) Prior Publication Data

US 2012/0264121 A1 Oct. 18, 2012

Related U.S. Application Data

(60) Provisional application No. 61/474,362, filed on Apr. 12, 2011.

(51) Int. Cl.
| | |
|---|---|
| *C12Q 1/68* | (2006.01) |
| *G06F 19/22* | (2011.01) |
| *G06F 19/24* | (2011.01) |
| *G06F 19/18* | (2011.01) |
| *C07H 21/04* | (2006.01) |

(52) U.S. Cl.
CPC ........... *C12Q 1/6809* (2013.01); *C12Q 1/6827* (2013.01); *C12Q 1/6883* (2013.01); *G06F 19/18* (2013.01); *C12Q 2600/156* (2013.01); *G06F 19/22* (2013.01); *G06F 19/24* (2013.01)

(58) Field of Classification Search
None
See application file for complete search history.

(56) References Cited

U.S. PATENT DOCUMENTS

| | | |
|---|---|---|
| 5,994,057 A | 11/1999 | Mansfield |
| 6,258,540 B1 | 7/2001 | Lo et al. |
| 6,403,315 B1 | 6/2002 | Drmanac |
| 6,440,706 B1 | 8/2002 | Vogelstein et al. |
| 6,555,315 B1 | 4/2003 | Short |
| 7,252,946 B2 | 8/2007 | Szasz |
| 7,332,277 B2 | 2/2008 | Dhallan |

(Continued)

FOREIGN PATENT DOCUMENTS

| | | |
|---|---|---|
| CN | 100519761 | 7/2009 |
| EP | 2 334 812 A2 | 6/2011 |

(Continued)

OTHER PUBLICATIONS

Jiang, P. et al. Bioinformatics 28(22):2833 (Sep. 2012).*

(Continued)

*Primary Examiner* — Diana B Johannsen
(74) *Attorney, Agent, or Firm* — Weaver Austin Villeneuve & Sampson LLP

(57) ABSTRACT

Methods of reliably estimating genomic fraction (e.g., fetal fraction) from polymorphisms such as small base variations or insertions-deletions are disclosed. Sequenced data from a multigenomic source is used to determine allele counts for one or more of the polymorphisms. For one or more of the polymorphisms, zygosity is assigned, and genomic fraction is determined from the zygosity and allele counts. Certain embodiments employ SNPs as the relevant polymorphism. The disclosed methods can be applied as part of an intentional, pre-designed re-sequencing study targeted against known polymorphisms or can be used in a retrospective analysis of variations found by coincidence in overlapping sequences generated from maternal plasma (or any other setting where a mixture of DNA from several people are present).

39 Claims, 14 Drawing Sheets

(56) References Cited

U.S. PATENT DOCUMENTS

| | | |
|---|---|---|
| 7,645,576 B2 | 1/2010 | Lo et al. |
| 7,888,017 B2 | 2/2011 | Quake et al. |
| 8,008,018 B2 | 8/2011 | Quake et al. |
| 8,137,912 B2 | 3/2012 | Kapur et al. |
| 8,195,415 B2 | 6/2012 | Fan et al. |
| 8,318,430 B2 | 11/2012 | Chuu et al. |
| 8,532,936 B2 | 9/2013 | Rava |
| 2002/0142324 A1 | 10/2002 | Wang et al. |
| 2003/0044388 A1 | 3/2003 | Dennis et al. |
| 2003/0064368 A1 | 4/2003 | Sakai et al. |
| 2003/0194704 A1 | 10/2003 | Penn et al. |
| 2004/0209299 A1 | 10/2004 | Pinter et al. |
| 2005/0221341 A1 | 10/2005 | Shimkets et al. |
| 2006/0046258 A1 | 3/2006 | Lapidus et al. |
| 2006/0121452 A1* | 6/2006 | Dhallan ............... 435/5 |
| 2006/0134599 A1 | 6/2006 | Toner et al. |
| 2006/0178835 A1 | 8/2006 | Marks |
| 2006/0257895 A1 | 11/2006 | Pinkel et al. |
| 2006/0286558 A1 | 12/2006 | Novoradovskaya et al. |
| 2007/0134658 A1 | 6/2007 | Bohmer et al. |
| 2007/0207466 A1 | 9/2007 | Cantor et al. |
| 2008/0020390 A1 | 1/2008 | Mitchell et al. |
| 2008/0050739 A1 | 2/2008 | Stoughton et al. |
| 2008/0064098 A1 | 3/2008 | Allickson |
| 2008/0070792 A1 | 3/2008 | Stoughton et al. |
| 2008/0138809 A1 | 6/2008 | Kapur et al. |
| 2008/0193927 A1 | 8/2008 | Mann et al. |
| 2008/0220422 A1 | 9/2008 | Shoemaker |
| 2008/0299562 A1 | 12/2008 | Oeth et al. |
| 2009/0026082 A1 | 1/2009 | Rothberg et al. |
| 2009/0029377 A1 | 1/2009 | Lo et al. |
| 2009/0087847 A1 | 4/2009 | Lo et al. |
| 2009/0098547 A1 | 4/2009 | Ghosh |
| 2009/0117542 A1 | 5/2009 | Maybruck et al. |
| 2009/0215042 A1 | 8/2009 | Sella-Tavor et al. |
| 2009/0270601 A1 | 10/2009 | Benner et al. |
| 2009/0291443 A1 | 11/2009 | Stoughton et al. |
| 2009/0299645 A1 | 12/2009 | Colby et al. |
| 2009/0307181 A1 | 12/2009 | Colby et al. |
| 2009/0317817 A1* | 12/2009 | Oeth et al. ............... 435/6 |
| 2009/0317818 A1 | 12/2009 | Ehrich et al. |
| 2010/0068711 A1 | 3/2010 | Umansky et al. |
| 2010/0093835 A1 | 4/2010 | McSwiggen et al. |
| 2010/0112575 A1 | 5/2010 | Fan et al. |
| 2010/0112590 A1 | 5/2010 | Lo et al. |
| 2010/0138165 A1 | 6/2010 | Fan et al. |
| 2010/0167954 A1 | 7/2010 | Earnshaw et al. |
| 2010/0184043 A1 | 7/2010 | Mitchell et al. |
| 2010/0184075 A1 | 7/2010 | Cantor et al. |
| 2010/0216151 A1 | 8/2010 | Lapidus et al. |
| 2010/0216153 A1 | 8/2010 | Lapidus et al. |
| 2010/0285537 A1 | 11/2010 | Zimmermann |
| 2011/0003293 A1 | 1/2011 | Stoughton et al. |
| 2011/0105353 A1* | 5/2011 | Lo et al. ............... 506/9 |
| 2011/0118145 A1 | 5/2011 | Akmaev et al. |
| 2011/0177517 A1 | 7/2011 | Rava et al. |
| 2011/0201507 A1 | 8/2011 | Rava et al. |
| 2011/0224087 A1 | 9/2011 | Quake et al. |
| 2011/0230358 A1 | 9/2011 | Rava |
| 2011/0245085 A1 | 10/2011 | Rava et al. |
| 2011/0312503 A1 | 12/2011 | Chuu et al. |
| 2011/0319272 A1 | 12/2011 | Fan et al. |
| 2012/0010085 A1 | 1/2012 | Rava et al. |
| 2012/0034603 A1 | 2/2012 | Oliphant et al. |
| 2012/0034685 A1 | 2/2012 | Sparks et al. |
| 2012/0040859 A1 | 2/2012 | Sparks et al. |
| 2012/0094849 A1 | 4/2012 | Rava et al. |
| 2012/0100548 A1 | 4/2012 | Rava et al. |
| 2012/0149582 A1 | 6/2012 | Rava et al. |
| 2012/0149583 A1 | 6/2012 | Rava et al. |
| 2012/0184449 A1 | 7/2012 | Hixon et al. |
| 2012/0214678 A1 | 8/2012 | Rava et al. |
| 2012/0214680 A1 | 8/2012 | Oeth et al. |
| 2012/0237928 A1 | 9/2012 | Rava et al. |
| 2012/0238738 A1 | 9/2012 | Hendrickson |
| 2013/0029852 A1 | 1/2013 | Rava et al. |
| 2013/0034546 A1 | 2/2013 | Rava et al. |
| 2013/0096011 A1 | 4/2013 | Rava et al. |
| 2014/0038830 A1 | 2/2014 | Srinivasan et al. |
| 2014/0199691 A1 | 7/2014 | Chuu et al. |

FOREIGN PATENT DOCUMENTS

| | | |
|---|---|---|
| EP | 2 513 339 | 10/2012 |
| EP | 1981995 | 7/2013 |
| GB | 2479476 A | 10/2011 |
| GB | 2479080 B | 1/2012 |
| GB | 2479471 A | 2/2012 |
| JP | 2006-508632 | 3/2006 |
| JP | 2013-509884 A | 3/2013 |
| WO | WO 96/19586 | 6/1996 |
| WO | WO 98/14275 | 4/1998 |
| WO | WO 98/44151 | 10/1998 |
| WO | WO 98/44151 A1 | 10/1998 |
| WO | WO 00/18957 | 4/2000 |
| WO | WO 00/18957 A1 | 4/2000 |
| WO | WO 03/004677 | 1/2003 |
| WO | WO 03/074723 | 9/2003 |
| WO | WO 03/074740 A1 | 9/2003 |
| WO | WO 2004/078999 A1 | 9/2004 |
| WO | WO 2005/039389 | 5/2005 |
| WO | WO 2006/010610 | 2/2006 |
| WO | WO 2006/028152 | 3/2006 |
| WO | WO 2006/028153 | 3/2006 |
| WO | WO 2007/100911 A2 | 9/2007 |
| WO | WO 2007/014709 | 12/2007 |
| WO | WO 2007/147074 A2 | 12/2007 |
| WO | WO 2009/013492 | 1/2009 |
| WO | WO 2009/013496 | 1/2009 |
| WO | WO 2009/046445 | 9/2009 |
| WO | WO 2010/033578 | 3/2010 |
| WO | WO 2011/051283 | 5/2011 |
| WO | WO 2011/051283 A1 | 5/2011 |
| WO | WO 2011/057094 A1 | 5/2011 |
| WO | WO 2011/090556 A1 | 7/2011 |
| WO | WO 2011/091046 A1 | 7/2011 |
| WO | WO 2011/091063 | 7/2011 |
| WO | WO 2012/019187 | 2/2012 |
| WO | WO 2012/019193 | 2/2012 |
| WO | WO 2012/019198 | 2/2012 |
| WO | WO 2012/019200 | 2/2012 |
| WO | WO 2012/071621 | 6/2012 |
| WO | WO 2012/078792 | 6/2012 |
| WO | WO 2012/088348 | 6/2012 |
| WO | WO 2012/103031 | 8/2012 |
| WO | WO 2012/103031 A2 | 8/2012 |
| WO | WO 2012/108920 | 8/2012 |
| WO | WO 2012/108920 A1 | 8/2012 |
| WO | WO 2012/142334 A2 | 10/2012 |
| WO | WO 2013/015793 | 1/2013 |

OTHER PUBLICATIONS

PCT Invitation to Pay Additional Fees dated Nov. 15, 2012 issued in International Patent Application No. PCT/US2012/033391.

U.S. Appl. No. 61/371,605, filed Aug. 6, 2010, Oliphant et al.

U.S. Appl. No. 13/087,842, filed Apr. 15, 2011, Rava.

U.S. Appl. No. 13/365,240, filed Feb. 2, 2012, Quake et al.

U.S. Appl. No. 13/400,028, filed Feb. 17, 2012, Rava et al.

U.S. Appl. No. 13/433,232, filed Mar. 28, 2012, Stoughton et al.

U.S. Office Action dated Mar. 13, 2012 issued in U.S. Appl. No. 13/368,035.

U.S. Office Action dated Jun. 28, 2012 issued in U.S. Appl. No. 13/323,683 with courtesy copy of pending claims.

U.S. Notice of Allowance dated Mar. 1, 2012 issued in U.S. Appl. No. 12/696,509, with courtesy copy of allowed claims.

European Search Report dated Feb. 22, 2012 issued in EP Patent Application 10 825 822.9.

European Examination Report dated Mar. 19, 2012 issued in EP Patent Application No. 10 825 822.9.

European Search Report dated Feb. 22, 2012 issued in EP Patent Application 10 830 938.6.

(56) References Cited

OTHER PUBLICATIONS

European Examination Report dated Mar. 16, 2012 issued in EP Patent Application No. 10 830 938.6.
European Search Report dated Feb. 22, 2012 issued in EP Patent Application 10 830 939.4.
European Examination Report dated Mar. 16, 2012 issued in EP Patent Application No. 10 830 939.4.
European Examination Report dated May 29, 2013 issued in EP App. EP 10 844 163.5.
UK Examination Report dated Dec. 16, 2011 issued in U.K. Patent Application No. 1108795.4.
UK Examination Report dated Dec. 7, 2011 issued in U.K. Patent Application No. 1114713.9.
UK Examination Report dated Jul. 15, 2011 issued in U.K. Patent Application No. 1107268.3.
UK Examination Report dated Jul. 15, 2011 issued in U.K. Patent Application No. 1108795.4.
UK Examination Report dated Jul. 15, 2011 issued in U.K. Patent Application No. 1108794.7.
UK Examination Report dated Jun. 24, 2011 issued in U.K. Patent Application No. 1106394.8.
UK Examination Report dated Nov. 15, 2011 issued in U.K. Patent Application No. 1107268.3.
PCT International Search Report and Written Opinion dated Feb. 28, 2011 for PCT Application No. PCT/US2010/058606.
PCT International Search Report and Written Opinion dated Mar. 1, 2011 issued in PCT Application No. PCT/US2010/058614.
PCT International Search Report and Written Opinion dated Apr. 4, 2011 issued in PCT Application No. PCT/US2010/058609.
PCT International Search Report and Written Opinion dated Apr. 11, 2011 issued in PCT Application No. PCT/US2011/021729.
PCT International Search Report and Written Opinion dated May 19, 2011 issued in PCT Application No. PCT/US2010/058612.
PCT International Search Report dated Mar. 11, 2013 issued in International Patent Application No. PCT/US2012/033391.
Ashoor et al. (2012) "Chromosome-selective sequencing of maternal plasma cell-free DNA for first-trimester detection of trisomy 21 and trisomy 18," Published online as DOI:10.1016/j.ajog.2012.01.029, to appear in: *American Journal of Obstetrics and Gynecology*, 22 pp.
Ashoor et al. "Fetal Fraction in Maternal Plasma Cell-Free DNA at 11-13 Week's gestation; Effect of Maternal and Fetal Factors," Published online Feb. 14, 2012 as DOI: 10.1159/000337373, 7 pp.
Bentley et al., (Nov. 6, 2008) "Accurate whole genome sequencing using reversible terminator chemistry," *Nature*, 456(7218)53-59.
Bianchi et al. (2012) "Genome-wide fetal aneuploidy detection by maternal plasma DNA sequencing," *Obstetrics and Gynecology*119(5):890-901.
Botezatu et al., "Genetic analysis of DNA excreted in urine: a new approach for detecting specific genomic DNA sequences from cells dying in an organism," *Clin. Chem.* Aug. 2000; 46(8 Pt 1):1078-84.
Butler et al., (Oct. 2007) "Short tandem repeat typing technologies used in human identity testing," *Bio Techniques*, 43(4):ii-v.
Butler et al., (Sep. 2003) "The development of reduced size STR amplicons as tools for analysis of degraded DNA," *J Forensic Sci.*, 48(5):1054-64.
Chan et al., (Jan. 2004) "Size distributions of maternal and fetal DNA in maternal plasma," *Clin Chem.* 50(1):88-92.
Chen et al., (Sep. 1996) "Microsatellite alterations in plasma DNA of small cell lung cancer patients," *Nat. Med.* 2(9):1033-5.
Chiu et al., (Dec. 23, 2008) "Noninvasive prenatal diagnosis of fetal chromosomal aneuploidy by massively parallel genomic sequencing of DNA in maternal plasma," *PNAS USA*105(51):20458-63.
Chiu et al., (Jul. 2009) "Non-invasive prenatal diagnosis by single molecule counting technologies," *Trends Genet.* 25(7): 324-31.
Chiu et al., (Mar. 2010) "Maternal plasma DNA analysis with massively parallel sequencing by ligation for noninvasive prenatal diagnosis of trisomy 21," *Clin. Chem.*56(3):459-63.
Chiu et al., (Jan. 11, 2011) "Non-invasive prenatal assessment of trisomy 21 by multiplexed maternal plasma DNA sequencing: large scale validity study," *BMJ*. 342:c7401, 9pp.
Chiu et al. (2012) "Noninvasive prenatal diagnosis empowered by high-throughput sequencing," *Prenatal Diagnosis*32(4):401-406.
Chu et al., (May 15, 2009) "Statistical model for whole genome sequencing and its application to minimally invasive diagnosis of fetal genetic disease," *Bioinformatics*, 25(10):1244-50.
Coble et al., (Jan. 2005) "Characterization of new miniSTR loci to aid analysis of degraded DNA," *J Forensic Sci.*, 50(1):43-53.
Dhallan et al., (Feb. 10, 2007) "A non-invasive test for prenatal diagnosis based on fetal DNA present in maternal blood: a preliminary study," *Lancet*.369(9560):474-81.
Ding et al. (2004) "MS analysis of single-nucleotide differences in circulating nucleic acids: Application to noninvasive prenatal diagnosis," *Proceedings of National Academy of Sciences*, 101(29):10762-10767.
Dixon et al., (Dec. 1, 2006) "Analysis of artificially degraded DNA using STRs and SNPs—results of a collaborative European (EDNAP) exercise," *Forensic Sci Int.*, 164(1):33-44.
Ehrich et al., (Mar. 2011) "Noninvasive detection of fetal trisomy 21 by sequencing of DNA in maternal blood: a study in a clinical setting," *Am J Obstet Gynecol.*, 204(3):20.e1-11.
Fan et al., (Oct. 1, 2007) "Detection of aneuploidy with digital polymerase chain reaction," *Anal Chem*.79(19):7576-9.
Fan et al., (Oct. 21, 2008) "Noninvasive diagnosis of fetal aneuploidy by shotgun sequencing DNA from maternal blood," *PNAS USA*. 105(42):16266-71.
Fan et al., (May 2009) "Microfluidic digital PCR enables rapid prenatal diagnosis of fetal aneuploidy," *Am J Obstet Gynecol*, 200(5):543.e1-7.
Fan et al., (Aug. 2010) "Analysis of the size distributions of fetal and maternal cell-free DNA by paired-end sequencing," *Clin Chem.* 56(8):1279-86.
Fan et al., (Dec. 8, 2010) "In principle method for noninvasive determination of the fetal genome," *Nature Precedings*10.1038/npre.2010.5373.1., 16 pp.
Fan et al., (May 3, 2010) "Sensitivity of noninvasive prenatal detection of fetal aneuploidy from maternal plasma using shotgun sequencing is limited only by counting statistics," *PLoS One.* 5(5):e10439, 7 pp.
Fan et al., (Jan. 2011) "Whole Genome Molecular Haplotyping of Single Cells," *Nat Biotechnol*. 29(1):51-7.
Ghanta et al., (Oct. 8, 2010) "Non-invasive prenatal detection of trisomy 21 using tandem single nucleotide polymorphisms," *PLoS One*, 5(10):e13184, 10 pp.
Grubwieser et al., (Mar. 2006) "A new "miniSTR-multiplex" displaying reduced amplicon lengths for the analysis of degraded DNA," *Int J Legal Med*.120(2):115-20.
Hanson et al., (Nov. 15, 2005) "Whole genome amplification strategy for forensic genetic analysis using single or few cell equivalents of genomic DNA," *Anal Biochem.*, 346(2):246-57.
Harris et al., "Single-molecule DNA sequencing of a viral genome," *Science*. Apr. 4, 2008; 320(5872):106-9.
Harrison et al., (Nov. 12, 1984) "Polymer-stimulated ligation: enhanced ligation of oglio- and-polynucleotides by T4 RNA ligase in polymer solutions," *Nucleic Acids Res.* 12(21):8235-51.
Hayashi et al., "Regulation of inter- and intramolecular ligation with T4 DNA ligase in the presence of polyethylene glycol," *Nucleic Acids Res.* Oct. 10, 1986; 14(19):7617-31.
Hill et al., "Characterization of 26 new miniSTR loci" Poster #44—17th *International Symposium on Human Identification*, Nashville, TN Oct. 10-12, 2006.
Huang et al., "Isolation of cell-free DNA from maternal plasma using manual and automated systems," *Methods Mol Biol*. 2008; 444:203-8.
Hung et al., "Detection of circulating fetal nucleic acids: a review of methods and applications," *J Clin Pathol*. Apr. 2009; 62(4):308-13.
Illumina, "Preparing samples for CHIP sequencing of DNA," E-pub at grcf.jhmi.edu/hts/protocols/11257047_ChIP_Sample_Prep.pdf. 2007, 15 pp.

(56) References Cited

OTHER PUBLICATIONS

International, The International HapMap Project. Nature. 2003;426:789-96.
Jama et al., "Quantification of Cell-Free Fetal DNA Levels in Maternal Plasma by STR Analysis," *ACMG Annual Clinical Genetics Meeting Poster*398; Mar. 24-28, 2010. Available online at http://acmg.omnibooksonline.com/2010/data/papers/398.pdf and http://acmg.omnibooksonline.com/2010/index/html, 2 pp.
Jorgez et al., "Improving enrichment of circulating fetal DNA for genetic testing: size fractionation followed by whole genome amplification," *Fetal Diagn Ther*. 2009; 25(3):314-9.
Ju et al., "Four-color DNA sequencing by synthesis using cleavable fluorescent nucleotide reversible terminators," *PNAS USA*, 2006; 103(52):19635-19640.
Kidd et al., "Developing a SNP panel for forensic identification of individuals," *Forensic Sci Int*. Dec. 1, 2006; 164(1):20-32.
Koide et al., (Jul. 2005) "Fragmentation of cell-free fetal DNA in plasma and urine of pregnant women," *Prenat. Diagn*, 25(7):604-7.
Kozarewa et al., (Apr. 2009) "Amplification-free Illumina sequencing-library preparation facilitates improved mapping and assembly of GC-biased genomes," *Nat Methods*. 6(4):291-295.
Lazinski & Camilli, Modified protocol for Illumina paired-end library construction. Available online at http://genomics.med.tufts.edu/documents/htseq_protocol_for_illumina_paired.pdf on Feb. 27, 2009. [Notified by Author Lazinski on May 8, 2012 that paper was first made available online on Feb. 27, 2009.], 10 pp.
Leon et al., "Free DNA in the serum of cancer patients and the effect of therapy," *Cancer Res*. Mar. 1977: 37(3):646-50.
Levy et al., (Sep. 4, 2007) "The Diploid Genome Sequence of an Individual Human," *PLoS Biol*. 5(10):e254.
Li et al., (Jun. 2004) "Size separation of circulatory DNA in maternal plasma permits ready detection of fetal DNA polymorphisms," *Clin Chem*.50(6):1002-11.
Liao et al., "Targeted massively parallel sequencing of maternal plasma DNA permits efficient and unbiased detection of fetal alleles," *Clin Chem*. Jan. 2011; 57(1):92-101.
Liu et al., (2007) "Feasibility study of using fetal DNA in maternal plasma for non-invasive prenatal diagnosis," *Acta Obstet Gynecol Scand*. 86(5):535-41.
Lo et al., (Aug. 16, 1997) "Presence of fetal DNA in maternal plasma," *Lancet*350(9076):485-7.
Lo et al., (Apr. 1998) "Quantitative analysis of fetal DNA in maternal plasma and serum: implications for noninvasive prenatal diagnosis," *Am J Hum Genet*. 62(4):768-75.
Lo, Y.M., (Dec. 10, 1998) "Prenatal Diagnosis of Fetal RhD Status by Molecular Analysis of Maternal Plasma," *The New England Journal of Medicine*, pp. 1734-1738.
Lo et al., (1999) "Rapid clearance of fetal DNA from maternal plasma," *Am J Hum Genet*. 64(1):218-24.
Lo et al., "Increased fetal DNA concentrations in the plasma of pregnant women carrying fetuses with trisomy 21," *Clin Chem*. Oct. 1999; 45(10):1747-51.
Lo et al., (Aug. 7, 2007) "Digital PCR for the molecular detection of fetal chromosomal aneuploidy," *PNAS USA*.104(32):13116-21.
Lo, Y.M., (Jan. 2008) "Noninvasive prenatal diagnosis of fetal chromosomal aneuploidies by maternal plasma nucleic acid analysis," *Clin Chem*.,54(3):461-466.
Lo, Y. M., (2009) "Noninvasive prenatal detection of fetal chromosomal aneuploidies by maternal plasma nucleic acid analysis: a review of the current state of the art," *BJOG*, 116: 152-157.
Lo et al., (Dec. 8, 2010) "Maternal plasma DNA sequencing reveals the genome-wide genetic and mutational profile of the fetus," *Sci Transl Med*. 2(61):61ra91.
Lun et al., (2008) "Microfluidics Digital PCR Reveals a Higher than Expected Fraction of Fetal DNA in Maternal Plasma," *Clinical Chemistry*, 54(10):1664-1672.
Lun et al. (2008) "Noninvasive prenatal diagnosis of monogenic diseases by digital size selection and relative mutation dosage on DNA in maternal plasma," *Proceedings of National Academy of Sciences*, 105(50):19920-19925.

Mckernan et al., "Sequence and structural variation in a human genome uncovered by short-read, massively parallel ligation sequencing using two-base encoding," *Genome Res*. Sep. 2009; 19(9):1527-41.
Metzker, (Jan. 2010) "Sequencing technologies—the next generation," *Nat Rev Genet*. 11(1):31-46.
Nakamoto et al., "Detection of microsatellite alterations in plasma DNA of malignant mucosal melanoma using whole genome amplification," *Bull Tokyo Dent Coll*. May 2008; 49(2):77-87.
Nicklas et al., "A real-time multiplex SNP melting assay to discriminate individuals," *J. Forensic Sci*. Nov. 2008; 53(6):1316-24.
Norton et al. "Non-Invasive Chromosomal Evaluation (NICE) Study: Results of multicenter, Prospective, Cohort Study for Detection of Fetal Trisomy 21 and Trisomy 18," Published online as DOI: 10..1016/j.ajog.2012.05.021, 30 pp.
Pakstis et al., "Candidate SNPs for a universal individual identification panel," *Hum Genet*. May 2007; 121(3-4):305-17.
Pakstis et al., "SNPs for a universal individual identification panel," *Hum Genet*. Mar. 2010; 127(3):315-24.
Pathak et al., "Circulating cell-free DNA in plasma/serum of lung cancer patients as a potential screening and prognostic tool," *Clin Chem*. Oct. 2006; 52(10):1833-42.
Pertl et al., "Detection of male and female DNA in maternal plasma by multiplex florescent polymerase chain reaction amplification of short tandem repeats," *Hum Genet*. Jan. 2000; 106(1)45-9.
Pheiffer et al., "Polymer-stimulated ligation: enhanced blunt- or cohesive-end ligation of DNA or deoxyribooligoncleotides by T4 DNA ligase in polymer solutions," *Nucleic Acids Res*. Nov. 25, 1983; 11(22):7853-71.
Pushkarev et al., "Single-molecule sequencing of an individual human genome," *Nat Biotechnol*. Sep. 2009; 27(9):847-50.
Quail et al., "A large genome center's improvements to the Illumina sequencing system," *Nat Methods*. Dec. 2008; 5(12):1005-10.
Schwartzenbach et al., "Cell-free tumor DNA in blood plasma as a marker for circulating tumor cells in prostate cancer," *Clin Cancer Res*. Feb. 1, 2009; 15(3):1032-8.
Schwartzenbach et al., "Comparative evaluation of cell-free tumor DNA in blood and disseminated tumor cells in bone marrow of patients with primary breast cancer," *Breast Cancer Res*. 2009; 11(5):R71, 9 pp.
Sehnert et al., "Optimal Detection of Fetal Chromosomal Abnormalities by Massively Parallel DNA Sequencing of Cell-Free Fetal DNA from Maternal Blood," *Clinical Chemistry*, Jul. 2011, vol. 57 No. 7:1042-1049. E-pub on Apr. 25, 2011 as doi:10.1373/clinchem. 2011.165910, 8 pp.
Sparks et al. "Non-invasive Prenatal Detection and Selective Analysis of Cell-free DNA Obtained from Maternal Blood: Evaluation for Trisomy 21 and Trisomy 18," E-Pub on Jan. 27, 2012 as DOI: 10.1016/j.ajog.2012.01.030, 33 pp.
Su et al., "Human urine contains small, 153-250 nucleotide-sized, soluble DNA derived from the circulation and may be useful in the detection of colorectal cancer," *J Mol Diagn*. May 2004; 6(2):101-7.
Tong et al. (2006) "Noninvasive prenatal detection of fetal trisomy 18 by epigenetic allelic ratio analysis in maternal plasma: Theoretical and empirical considerations," *Clinical Chemistry*52(2):2194-2202.
Tong et al., "Noninvasive prenatal detection of trisomy 21 by an epigenetic-genetic chromosome-dosage approach," *Clin Chem*. Jan. 2010; 56(1):90-8.
Vallone et al., "Demonstration of rapid multiplex OCR amplification involving 16 genetic loci.," *Forensic Sci Int Genet*. Dec. 2008; 3(1):42-5.
Voelkerding et al., "Digital Fetal Aneuploidy Diagnosis by Next-Generation Sequencing," *Clin Chem*. Mar. 2010; 56(3):336-8.
Voelkerding et al., "Next generation sequencing: from basic research to diagnostics," *Clin Chem* Apr. 2009; 55(4):641-58.
Vogelstein & Kinzler, Digital PCR. *PNAS* Aug. 1999; 96:9236-9241.
Wheeler et al., "The complete genome of an individual by massively parallel DNA sequencing," *Nature*. Apr. 17, 2008; 452(7189):872-6.
Wright et al., "The use of cell-free nucleic acids in maternal blood for non-invasive prenatal diagnosis," *Hum Reprod Update*. Jan.-Feb. 2009; 15(1):139-51.

(56) References Cited

OTHER PUBLICATIONS

Zimmerman & Pheiffer, "Macromolecular crowding allows blunt-end ligation by DNA ligase from rat liver or *Escheridia coli.,*" *PNAS USA*. Oct. 1983; 80(19)5852-6.
U.S. Office Action dated Feb. 24, 2014 issued in U.S. Appl. No. 12/958,347.
Australian Examiner's First Report dated Mar. 18, 2014 issued in AU 2012242698.
European Office Action dated Feb. 5, 2014 issued in EP 12 716 939.9.
U.S. Office Action dated Jul. 11, 2012 issued in U.S. Appl. No. 13/461,582.
U.S. Final Office Action dated Dec. 26, 2012 issued in U.S. Appl. No. 13/461,582.
U.S. Office Action dated Oct. 8, 2014 issued in U.S. Appl. No. 13/461,582.
PCT International Preliminary Report on Patentability and Written Opinion dated Oct. 24, 2013 issued in International Patent Application No. PCT/US2012/033391.
Chinese Office Action dated Sep. 28, 2014 issued in CN 201280028976.9.
Angeloni D., (May 24, 2007) "Molecular analysis of deletions in human chromosome 3p21 and the role of resident cancer genes in disease", *Briefings Functional Genomics* 6(1):19-39.
Bowcock et al., (1990) "Exclusion of the Retinoblastoma Gene and Chromosome 13q as the Site of a Primary Lesion for Human Breast Cancer," *Am J Hum Genet*, 46:12.
Caramazza et al., (2010) "Chromosome 1 abnormalities in myeloid malignancies: a literature survey and karyotype-phenotype associations," *Eur J Hematol*,84:191-200.
Craig et al. (1990) "Ordering of cosmid clones covering the Herpes simplex virus type I (HSV-1) genome: a test case for fingerprinting by hybrisation," *Nucleic Acids Research*, 18(9):2653-2660.
Eisenmann et al., (2009) "5q—myelodysplastic syndromes: chromosome 5q genes direct a tumor-suppression network sensing actin dynamics", *Oncogene*, 28:3429-3441.
Fanciulli et al., (2010) "Gene copy number variation and common human disease," *Clin Genet* 77(3):201-213.
Fonatsch C., (Jun. 2010) "The role of chromosome 21 in hematology and oncology", *Genes, Chromosomes and Cancer*, 49(6):497-508.
Harris et al., (2011) "Genome-wide array-based copy No. profiling in human placentas from unexplained stillbirths," *Prenatal Diagn* 31(10):932-944.
Howe et al., (Aug. 1990) "Retinoblastoma growth suppressor and a 300-kDa protein appear to regulate cellular DNA synthesis," *PNAS (USA)* 87:5883-5887.
Illanes et al., (Sep. 2007) "Early detection of cell-free fetal DNA in maternal plasma," *Early Human Dev* 83(9):563-566.
Jongsma et al., (2002) "Molecular evidence for putative tumour suppressor genes on chromosome 13q specific to BRCA1 related ovarian and fallopian tube cancer," *J Clin Pathol: Mol Path* 55(5):305-309.
Joosten et al., (Mar. 1997) "Full Monosomy 21, Prenatally Diagnosed by Fluorescent in Situ Hybridization," *Prenatal Diagn.* 17(3):271-5.
Langmead, et al., (2009) "Ultrafast and memory-efficient alignment of short DNA sequences to the human genome", *Genome Biology*, 10:R25.1-R25.10.
Le Cam (1956) "On the Asymptotic Theory of Estimation and Testing Hypotheses" *Proceedings of the Third Berkeley Symposium on Mathematical Statistics and 20 Probability*, Berkeley CA: University of CA Press, 1:129-156.
Margulies, M., et al., (2005) "Genome sequencing in microfabricated high-density picolitre reactors", and Supplemental Materials *Nature* 437:376-380.
Park et al., (Oct. 2008) "Unraveling the Biologic and Clinical Complexities of HER2," *Clinical Breast Cancer*, 8(5):392-401.
Redon et al., (Nov. 23, 2006), "Global Variation in copy number in the human genome," *Nature*, 444:444-454.
Rygaard et al., (1990) "Abnormalities in Structure and Expression of the Retinoblastoma Gene in Small Cell Lung Cancer Cell Lines and Xenografts in Nude Mice," *Cancer Res* 50:5312-5317.
Sato et al., (1990) "Allelotype of Breast Cancer: Cumulative Allele Losses Promote Tumor Progression in Primary Breast Cancer," *Cancer Res.*, 50:7184-7189.
Sebat et al., (Apr. 20, 2007) "Strong association of de novo copy number mutations with autism", *Science*, 316(5823):445-449.
Shaikh et al. (2009) "High-resolution mapping and analysis of copy number variations in the human genome: A data resource for clinical and research applications", *Genome Res*.19:1682-1690.
Soni , (2007) "Progress toward Ultrafast DNA Sequencing Using Solid-State Nanopores", *Clin Chem* 53(11):1996-2001.
Varmus H., (1984) "The Molecular Genetics of Cellular Oncogenes," *Ann Rev Genetics* 18:553-612.
Vosranova et al., (2008) "Partial monosomy 7q34-qter and 21pter-q22.13 due to cryptic unbalanced translocation t(7;21) but not monosomy of the whole chromosome 21: a case report plus review of the literature," *Molecular Cytogen*. 1:13.
Walsh et al., (2008) "Rare Structural Variants Disrupt Multiple Genes in Neurodevelopmental Pathways in Schizophrenia," *Science*, 320:539-543.
U.S. Final Office Action dated Jun. 18, 2015 issued in U.S. Appl. No. 13/461,582.
UK Examination Report dated Mar. 9, 2012 in U.K. Patent Application No. 1108795.4.
Chinese Second Office Action dated Apr. 13, 2015 issued in CN 201280028976.9.
European Office Action dated Mar. 10, 2015 issued in EP 12 716 939.9.
Japanese Office Action dated Apr. 22, 2015 issued in JP 2014-505313.
Amaral, et al., (Aug. 12, 2009) "Application of massive parallel sequencing to whole genome SNP discovery in the porcine genome," BMC Genomics, Biomed Central Ltd, London, UK, 10(1):374.
Lee et al., (Dec. 31, 2009) "Improving the efficiency of genomic loci capture using oligonucleotide arrays for high throughput resequencing," BMC Genomics, Biomed Central Ltd, London, UK, 10(646):1-12.
Li et al., (Jun. 1, 2009) "SNP detection for massively parallel whole-genome resequencing," Genome Research, 19(6):1124-1132.
Turner, et al., (Sep. 1, 2009) "Methods for Genomic Partitioning", Annual Review of Genomics and Human Genetics, 10(1):263-284.
Ashoor, et al., "Chromosome-selective sequencing of maternal plasma cell-free DNA for first-trimester detection of trisomy 21 and trisomy 18", American Journal of Obstetrics and Gynecology, 2012, 22.
Ashoor, et al., "Fetal Fraction in maternal plasma cell-free DNA at 11-13 weeks' gestation: effect of maternal and fetal factors", 2012, 7.
Bentley, et al., "Accurate whole human genome sequencing using reversible terminator chemistry", Nature, vol. 456, No. 7218, Nov. 6, 2008, 53-59.
Beroukhim, et al., "The landscape of somatic copy-number alteration across human cancers", Nature, vol. 463, Feb. 2010, 899-905.
Bianchi, et al., "Genome-Wide Fetal Aneuploidy Detection by Maternal Plasma DNA Sequencing", Obstetrics and Gynecology, vol. 119, No. 5, May 5, 2012, 890-901.
Borsting, "Multiplex PCR, amplicon size and hybridization efficiency on the NanoChip electronic microarray", Int J. Legal Med. vol. 118, 2004, 75.
Botezatu, et al., "Genetic Analysis of DNA excreted in urine: a new approach for detecting specific genomic DNA sequences from cells dying in an organism", Clin Chem. 46(8 Pt1), Aug. 2000, 1078-84.
Buck, et al., "Design Strategies and Performance of Custom DNA Sequencing Primers", Biotechniques vol. 27, 1999, 528-536.
Butler, et al., "Short tandem repeat typing technologies used in human identity testing", Biotechniques 43(4), Sep. 2003, ii-v.
Butler, et al., "The Development of reduced size STR amplicons as tools for analysis of degraded DNA", J. Forensic Sci 48(5), 2003, 1054-64.

(56) References Cited

OTHER PUBLICATIONS

Chan, et al., "Size Distributions of maternal and fetal DNA in Maternal Plasma", Clin. Chem 50(1), Jan. 2004, 88-92.
Chen, et al., "Microsatellite alterations in plasma DNA of small cell lung cancer patients", Nat Med. 2(9), 1996, 1033-5.
Chiang, et al., "High-resolution mapping of copy-number alterations with massively parallel sequencing", Nature Methods, vol. 6, No. 1 (2009), published online: doi:10.1038/nmeth.1276, Nov. 30, 2008, 99-103.
Chiu, et al., "Maternal Plasma DNA Analysis with Massively Parallel Sequencing by Ligation for Noninvasive Prenatal Diagnosis of Trisomy 21", Clinical Chemistry 56:3, 2010, 459-463.
Chiu, et al., "Non-invasive prenatal assessment of trisomy 21 by multiplexed maternal plasma DNA sequencing: large scale validity study", BMJ 342, 2011, c7401.
Chiu, et al., "Non-invasive prenatal diagnosis by single molecule counting technologies", Trends Genet. 25 (7), Jul. 2009, 324-31.
Chiu, et al., "Noninvasive prenatal diagnosis of fetal chromosomal aneuploidy by massively parallel genomic sequencing of DNA in maternal plasma", Proc Natl Acad Sci 105(51), Dec. 23, 2008, 20458-63.
Chu, et al., "Statistical model for whole genome sequencing and its application to minimally invasive of fetal genetic disease", Bioinformatics 25(10), May 15, 2009, 1244-40.
Clarke, et al., "Effects of chemotherapy and hormonal therapy for early breast cancer on recurrence and 15-year survival: an overview of randomised trials", Lancet vol. 365, 2005, 1687-1717.
Clarke, et al., "Effects of radiotherapy and of differences in the extent of surgery for early breast cancer on local recurrence and 15-year survival: an overview of the randomised trials", Lancet vol. 366, 2005, 2087-2106.
Coble, et al., "Characterization of New MiniSTR Loci to Aid Analysis of Degraded DNA", J Forensic Sci, 50(1), Jan. 2005, 43-53.
Deng, et al., "Enumeration and microfluidic chip separation of circulating fetal cells early in pregnancy from maternal blood", American journal of Obstetrics & Gynecology, vol. 199, Issue 6, Dec. 2008, S134.
Dhallan, et al., "A non-invasive test for prenatal diagnosis based on fetal DNA present in maternal blood: a preliminary study", Lancet 369(9560), Feb. 10, 2007, 474-81.
Ding, et al., "MS analysis of single-nucleotide differences in circulating nucleic acids: Application to noninvasive prenatal diagnosis", Proceedings of National Academy of Sciences 101(29), 2004, 10762-10767.
Dixon, et al., "Analysis of artificially degraded DNA using STRs and SNPs-results of a collaborative European (EDNAP) exercise", Forensic Sci Int 164(1), 2006, 33-44.
Ehrich, "Noninvasive detection of fetal trisomy 21 by sequencing of DNA in maternal blood: a study in a clinical setting", Am J Obstet Gynecol, 204(3), Mar. 2011, 205.e1-11.
Fan, et al., "Analysis of the size distributions of fetal and maternal cell-free Dna by paired-end sequencing", Clin. Chem 56(8), Aug. 2010, 1279-86.
Fan, et al., "Detection of aneuploidy with digital polymerase chain reaction", Anal Chem. 79(19), Oct. 1, 2007, 7576-9.
Fan, et al., "In principle method for noninvasive determination of the fetal genome", Nature Precedings: Nature Precedings 10.1038/npre, 2010, 5373.1.
Fan, et al., "Microfluidic digital PCR enables rapid prenatal diagnosis of fetal aneuploidy", Am J Obstet Gynecol 200(5), May 2009, 543.e1-7.
Fan, et al., "Noninvasive diagnosis of fetal aneuploidy by shotgun sequencing DNA from maternal blood", Proc Natl Acad Sci 105(42), Oct. 21, 2008, 16266-71.
Fan, et al., "Sensitivity of noninvasive prenatal detection of fetal aneuploidy from maternal plasma using shotgun sequencing is limited only by counting statistics", PLoS One 5(5), May 3, 2010, e10439.
Fan, et al., "Whole-genome molecular haplotyping of single cells", Nature Biotechnology, Advanced Online Publication, Dec. 19, 2010, 9 pages.
Frohling, et al., "Chromosomal Abnormalities in Cancer", New England Journal of Medicine, vol. 359, 2008, 722-734.
Ghanta, et al., "Non-Invasive Prenatal Detection of Trisomy 21 Using Tandem Single Nucleotide Polymorphisms", PLos ONE, vol. 5, Issue 10, e13184, Oct. 2010, 10 pages.
Goossens, et al., "Simultaneous mutation and copy No. variation (CNV) detection by multiplex PCR—based GS-FLX sequencing", Human Mutation, vol. 30, Issue 3, Dec. 2008, 472-476.
Grubweiser, et al., "A new "miniSTR-multiplex" displaying reduced amplicon lengths for the analysis of degrade DNA", Int J. Legal Med 120(2), 2006, 115-20.
Hanson, et al., "Whole genome amplification strategy for forensic genetic analysis using single or few cell equivalents of genomic DNA", Anal Biochem. 346(2), Nov. 15, 2005, 246-57.
Harris, et al., "Single-Molecule DNA Sequencing of a Viral Genome", Science 320, Apr. 4, 2008, 106-109 and Suppl. Materials 1-25.
Harrison, et al., "Polymer-stimulated ligation: enhanced ligation of oligo-and polynucleotides by T4 RNA ligase in polymer solutions", Nucleic Acids Research vol. 12 No. 21 1984, 1984, 8235-51.
Hayashi, et al., "Regulation of inter-and intramolecular ligation with T4 DNA ligase in the presence of polyethylene glycol", Nucleic Acids Res. 14(19), Oct. 10, 1986, 7617-31.
Hill, et al., "Characterization of 26 new miniSTR Loci", Poster #44 — 17th International Symposium on Human Identification, Nashville, TN, Oct. 1012, 2006, 1.
Hoffman, et al., "The genome-enabled electronic medical record", Journal of Biomedical Informatics 10 (2007) published online, Mar. 15, 2006, 44-46.
Huang, "Isolation of cell-free DNA from maternal plasma using manual and automated systems", Methods Mol Biol. 444, 2008, 203-8.
Hung, "Detection of circulating fetal nucleic acids: a review of methods and applications", J Clin Pathol 62(4), 4/62/2009, 308-13.
Illumina, "Preparing Samples for ChIP sequencing of DNA", E-pub at grcf.jhmi.edu/hts/protocols/11257047_ChIP_Sample_Prep.pdf., 2007, 15.
International, "The International HapMap Consortium Project", Nature 426:789-96, 2003, 8.
Jama, et al., "Quantification of cell-free fetal DNA Levels on maternal plasma by STR analysis", 2010 ACMG Annual Clinical Genetics Meeting, 2010, 2.
Jensen, et al., "Detection of Microdeletion 22q11.2 in a Fetus by Next-Generation Sequencing of Maternal Plasma", Clinical Chemistry 58:7; doi:10.1373/clinchem.2011.180794, May 4, 2012,.
Jiang, et al., "FetalQuant: deducing fractional fetal DNA concentration from massively parallel sequencing of DNA in maternal plasma", Bioinformatics, vol. 28, No. 22, 2012, 2883-2890.
Jorgez, et al., "Improving Enrichment of circulating fetal DNA for genetic testing: size fractionation followed by whole gene amplification", Fetal Diagn Ther 2009, 2009, 6.
Ju, et al., "Four-Color DNA Sequencing by Synthesis Using Cleavable Florescent Nucleotide Reversible Terminators", PNAS vol. 103, No. 52, 2006, 19635-19640.
Kidd, et al., "Developing a SNP panel for forensic identification of individuals", Forensic Science International 164 ( 2006), 2006, 20-32.
Kim, et al., "rSW-seq: algorithm for detection of copy number alterations in deep sequencing data", BMC Bioinformatics, vol. 11, Aug. 18, 2010, 432.
Koide, et al., "Fragmentation of cell-free fetal DNA in plasma and urine of pregnant women", www.interscience.wiley.com, Mar. 14, 2005, 4.
Kozarewa, et al., "Amplification-free Illumina sequencing-library preparation facilitates improved mapping and assembly of GC-biased genomes", UKPMC Funders Group Author Manuscript, Oct. 1, 2009, 12.
Lazinski, et al., "Modified Protocol for Illumina Paired-End Library Construction", http://genomics.med.tufts.edu/documents/htseq_protocol_for_illumina_paired.pdf, Feb. 27, 2009, 10.

(56) References Cited

OTHER PUBLICATIONS

Leon, et al., "Free DNA in the Serum of Cancer Patients and the Effect of Therapy", Cancer Research 37, Mar. 1, 1977, 646-650.
Levy, et al., "The Diploid Genome Sequence of an Individual Human", PLoS Biology, vol. 5, Issue 10, Oct. 2007, 2113- 2144.
Li, et al., "Size separation of circulatory DNA in maternal plasma permits ready detection of fetal DNA polymorphisms", Clinical Chemistry 50:6, 2004, 1002-11.
Liao, et al., "Targeted Massively parallel sequencing of maternal plasma DNA permits efficient and unbiased detection of fetal alleles", Clinical Chemistry 57:1, 2011, 92-101.
Liu, et al., "Feasibility study of using fetal DNA in maternal plasma for non-invasive prenatal diagnosis", Acta Obstet Gynecol Scand. 86(5), 2007, 535-41.
Lo, et al., "Digital PCR for the molecular detection of fetal chromosomal aneuploidy", Proc Natl Acad Sci USA. 104(32), Aug. 7, 2007, 13116-21.
Lo, et al., "Increased fetal DNA concentrations in the plasma of pregnant women carrying fetuses with trisomy 21", Clinical Chemistry 45:10, 1999, 1747-51.
Lo, et al., "Maternal plasma DNA sequencing reveals the genome-wide genetic and mutational profile of the fetus", Sci Transl Med. 2(61):, Dec. 8, 2010, 61ra91.
Lo, et al., "Noninvasive prenatal detection of fetal chromosomal aneuploidies by maternal plasma nucleic acid analysis: a review of the current state of the art", BJOG, vol. 116, 2009, 152-157.
Lo, et al., "Noninvasive prenatal diagnosis of fetal chromosomal aneuploidies by maternal plasma nucleic acid analysis", Clin Chem. 54(3), Jan. 2008, 461-466.
Lo, et al., "Prenatal diagnosis of fetal RhD Status by molecular analysis of maternal plasma", The New England Journal of Medicine, Dec. 10, 1998, 1734-1738.
Lo, et al., "Presence of fetal DNA in maternal plasma and serum", Lancet. 350(9076), Aug. 16, 1997, 485-7.
Lo, et al., "Quantitative analysis of fetal DNA in maternal plasma and serum: implications for noninvasive prenatal diagnosis", Am J Hum Genet 62(4), Apr. 1998, 768-75.
Lo, et al., "Rapid Clearance of fetal DNA from Maternal Plasma", Am J Hum Genet. 64(1), 1999, 218-24.
Lun, et al., "Microfluidics digital PCR Reveals a Higher than expected fraction of fetal DNA in maternal plasma", Clinical Chemistry, vol. 54, No. 10, 2008, 1664-1672.
Lun, "Noninvasive prenatal diagnosis of monogenic diseases by digital size selection and relative mutation dosage on DNA in maternal plasma", Proceedings of National Academy of Sciences 105(50), 2008, 19920-19925.
Mckernan, et al., "Sequence and structural variation in a human genome uncovered by short-read, massively parallel ligation sequencing using two-base encoding", Genome Res. 19(9), Sep. 2009, 1527-41.
Metzker "Sequencing technologies- the next generation", Nat Rev Genet. 11(1), Jan. 2010, 31-46.
Mullighan, et al., "Genome-wide profiling of genetic alterations in acute lymphoblastic leukemia: recent insights and future directions.", Leukemia vol. 23, Feb. 26, 2009, 1209-1218.
Meyerson, et al., "Advances in understanding cancer genomes through second-generation sequencing", Nature Reviews Genetics, vol. 11, 2010, 685-696.
Nakamoto, "Detection of Microsatellite alterations in Plasma DNA of Malignant Mucosal Melanoma Using Whole Genome Amplification", Bull Tokyo Dent Coll. May 2008; 49(2), May 2008, 77-87.
Nicklas, "A real-time multiplex SNP melting assay to discriminate individuals", J. Forensic Sci. 53(6):, Nov. 2008, 1316-24.
Norton, et al., "Non-invasive chromosomal evaluation (NICE) study: results of multicenter, prospective, cohort study for detection of fetal trisomy 21 and trisomy 18", Published online, May 21, 2012, 30 pgs.
Pakstis, et al., "Candidate SNPs for a universal individual identification panel", Hum Genet. 121(3-4), May, 2007, 305-17.
Pakstis, et al., "SNPs for a universal individual identification panel", Hum Genet. 127(3):, Mar. 2010, 315-24.
Pandey, et al., "Chapter 3 Applied Biosystems Solid Systems: Ligation-Based Sequencing", Next Generation Genome Sequencing: Towards Personalized Medicine 2008. Edited by Michael Janitz., 2008, 14.
Park, et al., "A single-tube protocol for next gen library construction increases", Cancer Research 71(8): Suppl. 1, Abstract No. 4851, Apr. 15, 2011.
Pathak, et al., "Circulating Cell-Free DNA in Plasma/Serum of Lung Cancer Patients as a Potential Screening and Prognostic Tool", Clin Chem. 52(10):, Oct. 2006, 1833-42.
Pennisi, E. "Semiconductors Inspire New Sequencing Technologies", Science 327, Mar. 5, 2010, 1190.
Pertl, et al., "Detection of male and female fetal DNA in maternal plasma by multiplex fluorescent polymerase chain reaction amplification of short tandem repeats", Hum Genet. 106(1), Jan. 2000, 45-9.
Peters, D. et al., "Noninvasive Prenatal Diagnosis of a Fetal Microdeletion Syndrome", New England Journal of Medicine 365;19, Correspondence, Nov. 10, 2001, 1847-1848.
Pheiffer, et al., "Polymer- stimulated ligation: enhanced blunt — or cohesive-end ligation of DNA or deoxyribooligonucleotides by T4 DNA ligase in polymer solutions", Nucleic Acids Res.11(22), Nov. 25, 1983, 7853-71.
Pui, et al., "Acute lymphoblastic leukaemia", Lancet vol. 371, 2008, 1030-1043.
Pushkarev, et al., "Single-molecule sequencing of an individual human genome", Nat Biotechnol. 27(9):, Sep. 2009, 847-50.
Quail, et al., "A large genome center's improvements to the Illumina sequencing system", Nature Methods, 5, 2008, 1005-1010.
Schwarzenbach, et al., "Cell-free Tumor DNA in Blood Plasma As a Marker for Circulating Tumor Cells in Prostate Cancer", Clin Cancer Res. 15(3):, Feb. 1, 2009, 1032-8.
Schwarzenbach, et al., "Comparative evaluation of cell-free tumor DNA in blood and disseminated tumor cells in bone marrow of patients with primary breast cancer", Breast Cancer Res. 11(5), 2009, R71.
Sehnert, et al., "Optimal Detection of Fetal Chromosomal Abnormalities by Massively Parallel DNA Sequencing of Cell-Free Fetal DNA from Maternal Blood", Clinical Chemistry, Jul. 2011, vol. 57 No. 7, E-pub on Apr. 25, 2011 as doi:10.1373/clinchem.2011. 165910., Apr. 25, 2011, 1042-1049.
Shendure, et al., "Next-generation DNA sequencing", Nature Biotechnology 26(10), 2008, 1135-1145.
Sparks, et al., "Non-invasive prenatal detection and selective analysis of cell-free DNA obtained from maternal blood: evaluation for trisomy 21 and trisomy 18", published online, Jan. 30, 2012, 33 pages.
Su, et al., "Human Urine Contains Small, 150 to 250 Nucleotide-Sized, Soluble Dna Derived from the Circulation and May be useful in the Detection of Colorectal Cancer", J Mol Diagn. 6(2), May 2004, 101-7.
Teixeira, et al., "Multiple numerical chromosome aberrations in cancer: what are their causes and what are their consequences?", Seminars in Cancer Biology, vol. 15, Issue 1, Feb. 2005, 3-12.
Thorstenson, et al., "An Automated Hydrodynamic Process for Controlled, Unbiased DNA Shearing", Genome Research 8, 1998, 848-855.
Tong, et al., "Noninvasive prenatal detection of trisomy 21 by an epigenetic-genetic chromosome-dosage approach", Clin Chem. 56(1), Jan. 2010, 90-8.
Tong, et al., "Noninvasive Prenatal Detection of Fetal Trisomy 18 by Epigenetic Allelic Ratio Analysis in Maternal Plasma: Theoretical and Empirical Considerations", Clinical Chemistry 52:12, 2006, 2194-2202.
Vallone, et al., "Demonstration of rapid multiplex Pcr amplification involving 16 genetic loci", Forensic Sci Int Genet. 3(1), Dec. 2008, 42-5.
Voelkerding, et al., "Digital Fetal Aneuploidy diagnosis by next-generation sequencing", Clin Chem. 56(3), Mar. 2010, 336-8.
Voelkerding, et al., "Next-Generation Sequencing: From Basic Research to Diagnostics", Clinical Chemistry 55:4, 2009, 641-658.

(56) References Cited

OTHER PUBLICATIONS

Vogelstein, et al., "Digital PCR", PNAS USA, vol. 96, 1999, 9236-9241.
Wheeler, et al., "The complete genome of an individual by massively parallel DNA sequencing", Nature. 452(7189), Apr. 17, 2008, 872-6.
Wright, et al., "The use of cell-free fetal nucleic acids in maternal blood for non-invasive prenatal diagnosis", Hum Reprod Update. 15(1), Jan.-Feb. 2009, 139-51.
Yamazawa, et al., "Monozygotic female twins discordant for Silver-Russell syndrome and hypomethylation of H19-DMR", J. Human Genetics, vol. 53, 2008, 950-955.
Zimmerman, et al., "Macromolecular crowding allows blunt-end ligation by DNA ligases from rat liver or *Escherichia coli*", Proc Natl Acas Sci USA. 80(19), Oct. 1983, 5852-6.
U.S. Office Action dated Nov. 13, 2014 issued in U.S. Appl. No. 13/555,037.
U.S. Notice of Allowance dated Jun. 16, 2015 issued in U.S. Appl. No. 13/555,037.
U.S. Office Action dated Jun. 10, 2015 issued in U.S. Appl. No. 13/600,043.
U.S. Notice of Allowance dated Jun. 3, 2015 issued in U.S. Appl. No. 13/555,010.
Australian Office Action dated Aug. 29, 2013 issued in AU Application No. 2011207561.
Chinese Third Office Action dated Sep. 17, 2015 issued in CN 201280028976.9.
PCT International Search Report dated Dec. 12, 2013 issued in PCT Application No. PCT/US2013/023909.
PCT International Preliminary Report on Patentability dated Jan. 29, 2015 issued in PCT Application No. PCT/US2013/023909.

\* cited by examiner

RESOLVING GENOME FRACTIONS USING POLYMORPHISM COUNTS

CROSS-REFERENCE TO RELATED APPLICATIONS

This application claims the benefit of and priority to U.S. Provisional Application Ser. No. 61/474,362, filed Apr. 12, 2011, the contents of which are incorporated herein by reference in their entirety and for all purposes.

BACKGROUND

The discovery of free floating fetal DNA (sometimes termed "cell free DNA" or "cfDNA") in maternal blood allows the possibility of detecting chromosomal abnormality, aneuploidy, and aberration from blood samples. Fractional abundance of fetal DNA in maternal blood plasma is not constant and varies with a variety of factors including sample handling and gestational age.

When using DNA sequencing to identify chromosomal aberrations or genetic defects it is important to know the relative abundance of fetal DNA in the total population of DNA. For example, when fetal fraction is known, the statistical power (the probability of identifying anomalous cases, or the sensitivity) can be calculated by permutation methods or via integration of linear combinations or convolutions of non-central F distributions from alpha to infinity where alpha critical point for the significance (maximum likelihood of falsely calling an anomaly) of the population of scores under the null hypothesis of no aberration.

A drawback of existing methods for detecting fetal fraction is that they reply upon measures of the abundance of sex chromosomes (which can only be used to reliably measure relative abundance of male embryonic DNA) or mRNA sequence of genes known to be differentially expressed between pregnant and embryonic tissue (which is subject to variability of expression due to gestational age or other factors).

Estimation of fetal fraction can be difficult because of several nuisance factors including: parental ethnic differential population genetics parameters and sequencing errors. Therefore it is desirable to have methods robust in the presence of these and other commonly occurring confounding factors.

SUMMARY

Certain disclosed embodiments relate to computational methods of reliably measuring the relative abundance of fetal free floating DNA by sequencing a maternal blood sample.

In specific embodiments, the invention provides methods of reliably estimating fetal fraction from polymorphisms such as small base variations or insertions-deletions which are robust with respect to parental ethnicity, embryo sex, gestational age and other environmental factors. Many examples disclosed herein employ SNPs as the relevant polymorphism. The invention can be applied as part of an intentional, pre-designed re-sequencing study targeted against known polymorphismsor can be used in a retrospective analysis of variations found by coincidence in overlapping sequences generated from maternal plasma (or any other setting where a mixture of DNA from several people are present).

This document presents techniques for the estimation of fractional abundance of fetal DNA in maternal blood samples. Certain disclosed techniques use the observed allele frequencies of SNPs found by chance or found in panels of pre-known SNPs designed for the purpose of estimating fetal fraction.

While much of the disclosure concerns estimating the fraction of fetal nucleic acid in a sample, the invention is not so limited. The techniques and apparatus described herein can be employed in many instances to estimate the fraction of nucleic acid from one genome in a mixture of two genomes, which may or may not be related as parent and child genomes.

Certain aspects of the disclosure pertain to methods of estimating the fraction of fetal DNA in DNA obtained from a bodily fluid of a pregnant individual. Such methods may be characterized by the following operations: (a) receiving a sample of the bodily fluid; (b) extracting DNA from the sample under conditions that extract DNA of both a maternal genome and a fetal genome present in the bodily fluid; (c) sequencing the extracted DNA with a nucleic acid sequencer under conditions that produce DNA segment sequences containing one or more polymorphisms; (d) mapping the DNA segment sequences derived from sequencing the DNA in the bodily fluid to one or more designated polymorphisms on a reference sequence; (e) determining allele frequencies of the mapped DNA segment sequences for at least one of the designated polymorphisms; (f) classifying the at least one designated polymorphism based on a combination of the zygosity of the pregnant individual and the zygosity of the fetus; and (g) estimating the fraction of fetal DNA in the DNA obtained from the pregnant individual using the allele frequencies determined in (e) and the combination of zygosities from (f).

The mapping may be performed using a computational apparatus programmed to map nucleic acid sequences to the one or more designated polymorphisms. In general, any of operations (d)-(g) may be performed on one or more processors running under program instructions.

In certain embodiments, the DNA obtained from a bodily fluid of a pregnant individual is cell-free DNA obtained from the plasma of the pregnant individual. Typically, the sequencing is conducted without selectively amplifying any of the one or more designated polymorphisms.

In certain embodiments, mapping the DNA segments obtained from the blood of the individual carrying the fetus comprises computationally mapping the segments to a database of polymorphisms. In certain embodiments, the classifying in (f) classifies the at least one designated polymorphism into one of the following combinations: (i) the pregnant individual is homozygous and the fetus is homozygous, (ii) the pregnant is individual homozygous and the fetus is heterozygous, (iii) the pregnant individual is heterozygous and the fetus is homozygous, and (iv) the pregnant individual is heterozygous and the fetus is heterozygous.

Various filtering operations may be employed. These include, for example, removing from consideration any polymorphism classified in combination (i) or combination (iv). In another example, the methods further include filtering the at least one designated polymorphisms to remove from consideration any polymorphism having a minor allele frequency of greater than a defined threshold. In yet another example, the methods include an operation of filtering the at least one designated polymorphisms to remove from consideration any polymorphism having a minor allele frequency of less than a defined threshold.

The classifying operation may be implemented in various ways. For example, it may involve applying a threshold to the allele frequency determined in (e). In another example, the classifying operation involves applying the allele frequency data from (e), obtained for a plurality of polymorphisms, to a mixture model. In one implementation, the mixture model employs factorial moments.

The fetal fraction determined as described herein may be used for various applications. In some examples, the methods described herein include an operation of executing program instructions on the one or more processors to automatically record the fraction of fetal of DNA as determined in (g) in a patient medical record, stored on a computer readable medium, for the pregnant individual. The patient medical record may be maintained by a laboratory, physician's office, a hospital, a health maintenance organization, an insurance company, or a personal medical record website. In another application, the estimate of the fraction of fetal DNA is used to prescribe, initiate, and/or alter treatment of a human subject from whom the maternal test sample was taken. In another application, the estimate of the fraction of fetal DNA is used to order and/or perform one or more additional tests.

Another aspect of the disclosure concerns apparatus for estimating the fraction of fetal DNA in DNA obtained from a bodily fluid of a pregnant individual. Such apparatus may be characterized by the following features: (a) a sequencer configured to (i) receive DNA extracted from a sample of the bodily fluid comprising DNA of both a maternal genome and a fetal genome, and (ii) sequence the extracted DNA under conditions that produce DNA segment sequences containing one or more designated polymorphisms; and (b) a computational apparatus configured to (e.g., programmed to) instruct one or more processors to perform various operations such as those described with two or more of the method operations described herein. In some embodiments, the computational apparatus is configured to (i) map nucleic acid sequences to the one or more designated polymorphisms on a reference sequence, (ii) determine allele frequencies of the mapped DNA segment sequences for at least one of the designated polymorphisms, (iii) classify the at least one designated polymorphism based on a combination of the zygosity of the pregnant individual and the zygosity of the fetus, and (iv) estimate the fraction of fetal DNA in the DNA obtained from the pregnant individual using the allele frequencies and the combination of zygosities.

In certain embodiments, the apparatus also includes a tool for extracting DNA from the sample under conditions that extract DNA of both the maternal genome and the fetal genome. In some implementations, the apparatus includes a module configured to extract cell-free DNA obtained from plasma of the pregnant individual for sequencing in the sequencer.

In some examples, the apparatus includes a database of polymorphisms. The computational apparatus may be further configured to instruct the one or more processors to map the DNA segments obtained from the blood of the individual carrying the fetus by computationally mapping the segments to the database of polymorphisms. The sequences in the database is an example of a reference sequence. Other examples of reference sequences are presented below.

In certain embodiments, the computational apparatus is further configured to instruct the one or more processors to classify the at least one designated polymorphism into one of the following combinations: (i) the pregnant individual is homozygous and the fetus is homozygous, (ii) the pregnant is individual homozygous and the fetus is heterozygous, (iii) the pregnant individual is heterozygous and the fetus is homozygous, and (iv) the pregnant individual is heterozygous and the fetus is heterozygous. In some embodiments, the computational apparatus is further configured to instruct the one or more processors to remove from consideration any polymorphism classified in combination (i) or combination (iv).

In certain embodiments, the computational apparatus is further configured to instruct the one or more processors to remove from consideration any polymorphism having a minor allele frequency of greater than a defined threshold. In some embodiments, the computational apparatus is further configured to instruct the one or more processors to filter the one or more designated polymorphisms to remove from consideration any polymorphism having a minor allele frequency of less than a defined threshold. In certain embodiments, the computational apparatus is further configured to instruct the one or more processors to classify the at least one designated polymorphism by applying a threshold to the allele frequency.

In certain embodiments, the computational apparatus is further configured to instruct the one or more processors to classify the at least one designated polymorphism by applying the allele frequency data obtained for a plurality of polymorphisms, to a mixture model. The mixture model may employ factorial moments.

In certain embodiments, the computational apparatus is further configured to instruct the one or more processors to automatically record the fraction of fetal of DNA in a patient medical record, stored on a computer readable medium, for the pregnant individual. The patient medical record may be maintained by a laboratory, physician's office, a hospital, a health maintenance organization, an insurance company, or a personal medical record website.

Another aspect of the disclosure concerns methods of estimating a fraction of fetal DNA in DNA obtained from a bodily fluid of a pregnant individual according to the following operations: (a) mapping segments of DNA obtained from the bodily fluid of the pregnant individual to a plurality of polymorphism sequences, wherein the DNA was sequenced under conditions that identify the plurality of polymorphism sequences; (b) determining an allele frequency of the mapped nucleic acids for each of the plurality polymorphism sequences; and (c) applying the allele frequencies to a mixture model to obtain an estimate of the fraction of fetal DNA in the DNA obtained from the blood of the individual carrying the fetus. Any one or more of operations (a)-(c) may be performed on one or more processors running under program instructions. In certain embodiments, operation (c) involves executing instructions on the one or more processors for solving a series of equations for factorial moments of allele frequency data for each of the plurality of polymorphism sequences. In some embodiments, the mixture model accounts for sequencing error.

In certain embodiments, the methods additionally include computationally removing allele frequencies for polymorphisms identified has being heterozygous in both the fetus and the pregnant individual. In some implementations, prior to (c), the methods include an operation of computationally removing allele frequencies for polymorphisms identified has being homozygous in both the fetus and the pregnant individual. In some implementations, prior to (c), the methods include an operation of computationally removing allele frequencies for polymorphisms identified has being heterozygous in the pregnant individual.

The DNA obtained from a bodily fluid of a pregnant individual may be cell-free DNA obtained from the plasma of the pregnant individual. The mapping of the nucleic acids obtained from bodily fluid may be implemented by mapping the segments to a database of polymorphisms.

The methods of this aspect of the disclosure may further include sequencing the DNA from the bodily fluid of pregnant individual with a nucleic acid sequencer under conditions that produce DNA segment sequences containing the polymorphism sequences.

In some implementations, the mapping in (a) comprises identifying a plurality of biallelic polymorphism sequences. In other embodiments, the mapping in (a) comprises mapping the segments of DNA to a plurality of pre-defined polymorphism sequences.

In some embodiments, the methods of this aspect additionally include executing program instructions on the one or more processors to automatically record the fraction of fetal of DNA as determined in (c) in a patient medical record, stored on a computer readable medium, for the pregnant individual. The patient medical record may be maintained by a laboratory, physician's office, a hospital, a health maintenance organization, an insurance company, or a personal medical record website.

Based on the estimate of the fraction of fetal DNA, the methods of this aspect may further include prescribing, initiating, and/or altering treatment of a human subject from whom the maternal test sample was taken. Based on the estimate of the fraction of fetal DNA, the methods of this aspect may further include ordering and/or performing one or more additional tests.

In accordance with yet another aspect of the disclosure, methods are provided for estimating the fraction of fetal DNA in DNA obtained from a bodily fluid of a pregnant individual using the following operations: (a) receiving a sample of the bodily fluid; (b) extracting DNA from the sample under conditions that extract DNA of both a maternal genome and a fetal genome present in the bodily fluid; (c) sequencing the extracted DNA with a nucleic acid sequencer under conditions that produce DNA segment sequences; (d) comparing the DNA segment sequences derived from the bodily fluid and from the comparison identifying one or more biallelic polymorphisms; (e) determining allele frequencies of the DNA segment sequences for at least one of the identified polymorphisms; (f) classifying the at least one identified polymorphism based on a combination of the zygosity of the pregnant individual and the zygosity of the fetus; and (g) estimating the fraction of fetal DNA in the DNA obtained from the pregnant individual using the allele frequencies determined in (e) and the combination of zygosities from (f).

The mapping may be performed using a computational apparatus programmed to map nucleic acid sequences to the one or more designated polymorphisms. In general, any of operations (d)-(g) may be performed on one or more processors running under program instructions.

In certain implementations of this aspect, the DNA segment sequences have a length of between about 20 base pairs and about 300 base pairs.

In certain embodiments of this aspect, the classifying in (f) classifies the at least one identified polymorphism into one of the following combinations: (i) the pregnant individual is homozygous and the fetus is homozygous, (ii) the pregnant is individual homozygous and the fetus is heterozygous, (iii) the pregnant individual is heterozygous and the fetus is homozygous, and (iv) the pregnant individual is heterozygous and the fetus is heterozygous. The methods may further include removing from consideration any polymorphism classified in combination (i) or combination (iv).

In accordance with various embodiments, the methods of this aspect may include filtering and/or classifying operations as described herein in connection with other aspects. For example, the methods of this aspect may include filtering the one or more identified polymorphisms to remove from consideration any polymorphism having a minor allele frequency of greater than a defined threshold. In some cases, the classifying the at least one identified polymorphism includes applying a threshold to the allele frequency determined in (e). The use of mixture models may as described herein may be employed to classify the identified polymorphisms.

Another aspect of the disclosure concerns apparatus for estimating a fraction of fetal DNA and including the following elements: (a) a sequencer configured to (i) receive DNA extracted from a sample of the bodily fluid comprising DNA of both a maternal genome and a fetal genome, and (ii) sequence the extracted DNA to produce sequence segments of DNA; and (b) a computational apparatus configured to instruct one or more processors to (i) map the sequence segments of DNA obtained from the bodily fluid of the pregnant individual to a plurality of polymorphism sequences, (ii) determine an allele frequency for each of the plurality of polymorphism sequences from the mapped sequence segments of DNA, and (iii) apply the allele frequencies to a mixture model to obtain an estimate of the fraction of fetal DNA in the DNA obtained from the blood of the individual carrying the fetus.

Yet another apparatus for estimating the fraction of fetal DNA includes the following elements: (a) a sequencer configured to (i) receive DNA extracted from a sample of the bodily fluid comprising DNA of both a maternal genome and a fetal genome, and (ii) sequence the extracted DNA under conditions that produce DNA segment sequences; and (b) a computational apparatus configured to instruct one or more processors to (i) compare the DNA segment sequences derived from the bodily fluid and from the comparison identifying one or more biallelic polymorphisms, (ii) determine allele frequencies of the DNA segment sequences for at least one of the identified polymorphisms, (iii) classify the at least one identified polymorphism based on a combination of the zygosity of the pregnant individual and the zygosity of the fetus, and (iii) estimate the fraction of fetal DNA in the DNA obtained from the pregnant individual using the allele frequencies and the combination of zygosities.

The instructions and/or hardware employed in the apparatus aspects described herein may provide for execution of any one or more of the computational or algorithmic operations of the method aspects disclosed herein, regardless of whether such operations are explicitly recited above.

These and other features and advantages of the disclosed embodiments will be described in more detail below with reference to the associated drawings.

DETAILED DESCRIPTION

Introduction and Overview

Figure 1:
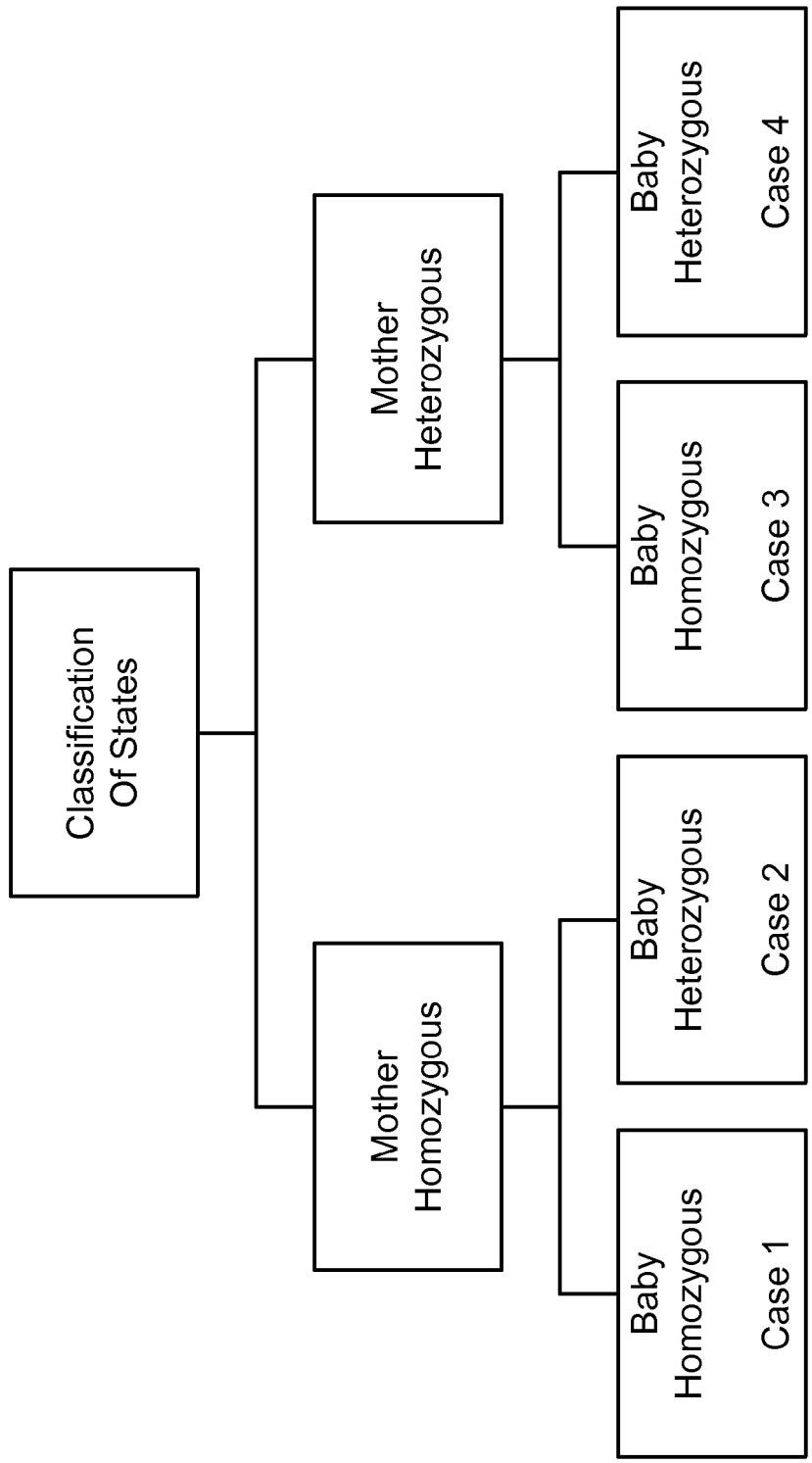
FIG. 1 is a block diagram depicting classification of fetal and maternal zygosity states for a given genomic position.

Certain disclosed embodiments involve analyzing DNA taken from a pregnant female's blood and using the analysis to estimate the fraction of that DNA that comes from the fetus. The fetal fraction of DNA may then be used to ascribe some level of confidence to another metric or characterization of the fetus based on independent analysis of the DNA taken from the mother's blood. For example, a fetal DNA sample taken from maternal blood may be separately analyzed to detect aneuploidy in the fetus being carried by the pregnant female. The aneuploidy determination made by this separate analysis may be given by a statistically grounded confidence level based on the fractional amount of fetal DNA present in the DNA taken from the mother's blood. Relatively low fractions of fetal DNA in the total complement of DNA suggest a low confidence in any characterization based upon fetal DNA.

Typically, though not necessarily, the analyzed DNA in the mother's blood is cell-free DNA, although in some embodiments, it may be cell-bound DNA. Cell-free DNA is taken from the mother's plasma. The amount of fetal DNA in the cell-free DNA content taken from pregnant females varies widely depending on a variety of factors including the gestational age of the fetus. For typical pregnant human females, it is currently believed that about 5-20% of the cell-free DNA is fetal DNA. However, it is not uncommon for the fetal fraction to be significantly lower (e.g., about 1% or lower). In such cases, any separate characterization of the fetal DNA may be inherently suspect. On the other hand, some researchers have reported maternal cell-free DNA samples having fetal DNA fractions as high as 40% or 50%.

In certain implementations described herein, determination of fetal fraction of maternal DNA relies on multiple DNA sequence readings at sequence sites known to harbor one or more polymorphisms. Typically, though not necessarily, such polymorphisms are single nucleotide polymorphisms (SNP). Other types of suitable polymorphisms include deletions, STRs (Short Tandem Repeats), insertions, indels (including microindels), etc. Further examples are presented below. In certain embodiments, the polymorphism sites are found on a "reference sequence" as described below. In some embodiments, the polymorphism sites are discovered while aligning sequence tags to one another and/or a reference sequence.

Certain disclosed methods make use of the fact that a fetus's DNA sequences at the polymorphism sites under consideration may not correspond to those of its mother. For example, the mother's DNA at the site of a particular SNP may be homozygous, while the fetus's version of the SNP will be heterozygous. Hence, a collection of sequence samples taken for the SNP in question will be heterogeneous with the majority of the sequences containing the major allele and the remaining fraction containing the minor allele. The relative amounts of the major and minor alleles are determined by the fraction of fetal DNA in the sample.

It should be mentioned that in a homozygous sample both copies of a given SNP or other polymorphism contain the same allele, while a heterozygous SNP or other polymorphism contains one copy of the major allele and one copy of the minor allele. One knows, therefore, that DNA taken exclusively from a heterozygous individual should contain 50% of the major allele and 50% of the minor allele. This knowledge can be used in elucidating the fraction of fetal DNA as outlined below. As explained more fully below, various methods disclosed herein consider only polymorphisms in which there are only two alleles in the maternal and fetal DNA, collectively.

In some implementations, the DNA taken from the mother's blood is read many times, with the total number of reads mapping to a particular site of a polymorphism being deemed the "coverage" of the polymorphism, and the number of reads mapping to the minor allele for that polymorphism being deemed the minor allele count. The ratio of minor allele count to coverage is important in various implementations.

Certain of the methods disclosed herein identify and characterize four cases of polymorphisms in DNA samples that comprise DNA from both the mother and the fetus. FIG. 1 below depicts these four cases. Specifically, in a first case, which is rather uninteresting, both the mother and the fetus are homozygous at the particular polymorphism being considered. In such case, every sequence in the DNA sample containing the polymorphism in question will contain the same allele and no information can be gleaned about the relative amounts of DNA from the mother and the fetus. It should be noted, however, that this case could be interesting in the sense that it allows the researcher or technician to gain some idea of the relative error rate of the DNA sequencing apparatus used to generate the sequence data under consideration.

The second case that the analysis will encounter is a polymorphism for which the pregnant female is homozygous and the fetus is heterozygous. In this case, a relatively small, but nevertheless significant, fraction of the detected sequences will contain the minor allele. Specifically, in this second case, the frequency of the minor allele is nominally given by the fraction of fetal DNA in the mother's bloodstream divided by two.

In a third case, the polymorphism under consideration is heterozygous in the mother's DNA and homozygous in the fetus's DNA. In this situation, the frequency of the minor allele is nominally given by 0.5 minus one-half of the fraction of fetal DNA in the DNA sample.

Finally, in the fourth case, the polymorphism under consideration is heterozygous in both the mother and the fetus. In this case, it is expected that the frequency of the major and minor alleles will both be 0.5. As with the first case, the fourth case is relatively uninteresting for determining the fetal fraction of DNA.

If the researcher, technician, or software tasked with determining the fraction of fetal DNA in a sample knew for a given polymorphism which of the four cases that polymorphism belonged to, then the fraction of fetal DNA could be directly estimated, assuming that the polymorphism under consideration fell into either case two or case three. In practice, however, one never has this knowledge a priori. Therefore computational apparatus is required to perform the operations described herein.

In certain embodiments, described elsewhere herein, a thresholding technique is employed to classify a single polymorphism into one of the four cases. Once the polymorphism is so classified, and found to reside in either case 2 or 3, the fetal fraction can be estimated. In other embodiments, the technique considers multiple polymorphisms distributed throughout all or a portion of the genome. As illustrated in the specific examples, multiple different SNPs across the genome may be used for this purpose.

In particular embodiments, the allele frequency is determined for a number of different polymorphisms in a DNA sample taken from a mother's blood sample. For this plurality of polymorphisms, some fraction will correspond to zygosity case 1, another fraction will correspond to case 2, a third fraction will correspond to case 3, and a final fraction will correspond to case 4. These fractions will sum to a value of 1. A mixture model or related technique may be employed to tease out one or more statistical properties of the polymorphisms in each of these four categories. Specifically, a mixture model may be employed to determine a mean and optionally the variance for each of the four cases encountered in a DNA sample taken from a pregnant female's blood. In specific embodiments, this is the mean and variance associated with the frequency of the minor allele in relation to the total number of counts for a polymorphism under consideration (coverage). As elaborated elsewhere herein, the mean values for each of these four categories, or at least the second and third categories, are directly related to the fetal fraction in the DNA taken from the mother's blood.

In a specific implementation employing mixture models, one or more factorial moments are calculated for each position where a polymorphism is being considered. For example, a factorial moment (or a collection of factorial moments) is calculated using multiple SNP positions considered in the DNA sequence. As shown in equation 4 below, each of the various factorial moments is a summation over all the various SNP positions under consideration for the ratio of minor allele frequency to coverage for a given position. As shown in equation 5 below, these factorial moments are also related to the parameters associated with each of the four zygosity cases described above. Specifically, they related to the probability for each of the cases as well as the relative amounts of each of the four cases in the collection of polymorphisms under consideration. As explained, the probability is a function of the fraction of fetal DNA in the cell-free DNA in the mother's blood. As explained more fully below, by calculating a sufficient number of these factorial moments (which are shown in equation 4), the method provides a sufficient number of expressions to solve for all the unknowns. The unknowns in this case would be the relative amounts of each of the four cases in the population of polymorphisms under consideration as well as the probabilities (and hence fetal DNA fractions) associated with each of these four cases. See equation 5. Similar results can be obtained using other versions of mixture models as represented in equations 7-12 below. These particular versions make use of only polymorphisms falling into cases 1 and 2, with polymorphisms for cases 3 and 4 being filtered by a thresholding technique.

Thus, the factorial moments may be used as part of a mixture model to identify the probabilities of any combination of the four cases of zygosity. And, as mentioned, these probabilities, or at least those for the second and third cases, are directly related to the fraction of fetal DNA in the total cell-free DNA in the mother's blood.

It should also be mentioned that sequencing error may be employed to reduce the complexity of the system of factorial moment equations that must be solved. In this regard, it should be recognized that the sequencing error actually can have any one of four results (corresponding to each of the four possible bases at any given polymorphism position).

In certain embodiments, tags are aligned with a reference chromosome or genome, and biallelic polymorphisms are identified. These polymorphisms are not predefined or otherwise identified prior to alignment. They are simply identified during alignment and then characterized based on their zygosities and minor allele counts as described herein. This information is used to estimate genome fractions as described herein.

The lengths of the tags used in embodiments described herein will generally be determined by the sequencing method employed to generate the tags. The methods are robust across a wide range of tag lengths. In certain implementations, the tags are between about 20 to 300 base pairs in length (or about 30 to 100 base pairs in length).

Figure 2:
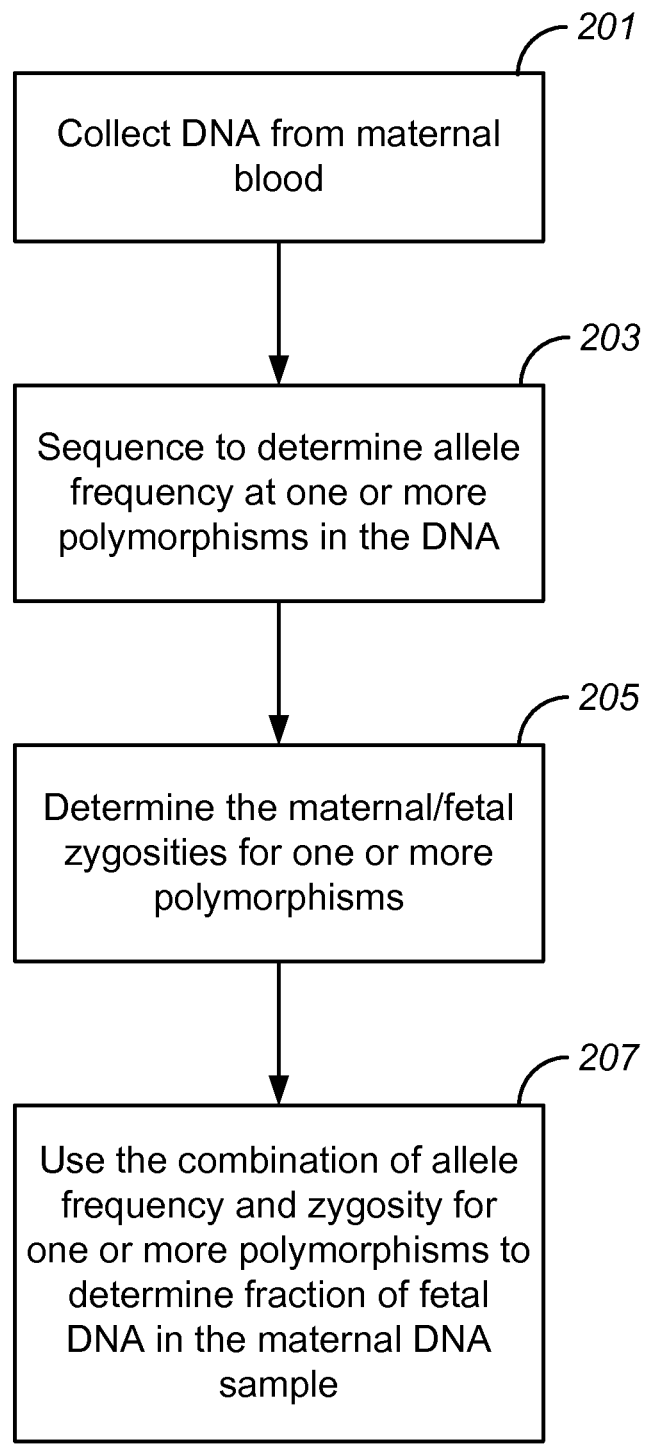
FIG. 2 is an example process flow for implementing some of the disclosed embodiments.

An example process flow for implementing some of the disclosed embodiments is shown in FIG. 2. As depicted there, the process begins at 201 with collection of DNA (cell-free or cell bound) from maternal blood or other bodily fluid. From this DNA multiple sequences mapped to one or more polymorphisms in a reference sequence. This mapping provides an allele frequency for each of the polymorphisms. See block 203.

More specifically, the process at block 203 may involve reading sequences of the collected DNA at locations of multiple polymorphisms. In some cases, these may be generated as part of the process for ploidy determinations or other determination made with respect to the fetal DNA. Thus, in some embodiments, separate sequences need not be generated. The read sequences are aligned to a reference sequence to maximize alignment using BLAST or a similar tool.

The reference sequence may be provided as a database of polymorphisms. In some cases, this is an allele search reference set produced from a combinatorial expansion of all polymorphism definitions (e.g., in the case where the polymorphisms are SNPs, all SNP sequences). See the appendix for example. In a specific example, the sequences are about 100 to 150 base pairs in length.

Returning to FIG. 2, the method determines the maternal/fetal zygosity combination for one or more the polymorphisms considered in the operation of block 203. See block 205. A mixture model may be employed for this purpose in certain embodiments. As mentioned, the combinations are as follows: M&F homozygous, M homozygous and F heterozygous, M heterozygous and F homozygous, and M&F heterozygous.

Finally, as illustrated at block 207, the method uses the combination of zygosity case allele frequency at one or more of the polymorphisms to estimate the fractional amount of fetal component in the DNA from the maternal sample.

DEFINITIONS

The following discussion is provided as an aid in understanding certain aspects and advantages of the disclosed embodiments.

The term "read" refers to a sequence read from a portion of a nucleic acid sample. Typically, though not necessarily, a read represents a short sequence of contiguous base pairs in the sample. The read may be represented symbolically by the base pair sequence (in ATCG) of the sample portion. It may be stored in a memory device and processed as appropriate to determine whether it matches a reference sequence or meets other criteria. A read may be obtained directly from a sequencing apparatus or indirectly from stored sequence information concerning the sample.

The term "tag" also refers to short sequences from a nucleic acid sample. Typically, a tag contains associated information such as the location of the sequence in the genome. For some purposes, the terms read and tag are interchangeable herein. Typically, however, sequence reads are aligned to a reference sequence, and reads that map at only one site on the reference genome are called tags. The "segment sequence" is sometimes used herein interchangeably with "tag."

Frequently herein "reads" are described as sequences of nucleic acids that are 36 base pairs in length (36mers). Of course, the disclosed embodiments are not limited to this size. Smaller and larger reads are suitable in many applications. For applications that align reads to the human genome, a read of size 30 base pairs or greater is generally considered sufficient to map a sample to a single chromosome. Much larger tags/reads are suitable for some applications. With whole genome sequencing, reads on the order of 1000 base pairs or greater may be used. In certain embodiments, a read may have a length of between about 20 and 10,000 base pairs, or between about 30 and 1000 base pairs, or between about 30 and 50 base pairs.

A "reference sequence" is a sequence of a biological molecule, which is frequently a nucleic acid such as a chromosome or genome. Typically multiple reads are members of a given reference sequence. In certain embodiments, a read or tag is compared to a reference sequence to determine whether the reference sequence contains the read sequence. This process is sometimes referred to as alignment.

In various embodiments, the reference sequence is significantly larger than the reads that are aligned to it. For example, it may be at least about 100 times larger, or at least about 1000 times larger, or at least about 10,000 times larger, or at least about $10^5$ times larger, or at least about $10^6$ times larger, or at least about $10^7$ times larger.

In one example, the reference sequence is that of a full length human genome. Such sequences may be referred to as genomic reference sequences. In another example, the reference sequence is limited to a specific human chromosome such as chromosome 13. Such sequences may be referred to as chromosome reference sequences. Other examples of reference sequences include genomes of other species, as well as chromosomes, sub-chromosomal regions (such as strands), etc. of any species.

In various embodiments, the reference sequence is a consensus sequence or other combination derived from multiple individuals. However, in certain applications, the reference sequence may be taken from a particular individual.

The term "alignment" refers to the process of comparing a read or tag to a reference sequence and thereby determining whether the reference sequence contains the read sequence. If the reference sequence contains the read, the read may be mapped to the reference sequence or, in certain embodiments, to a particular location in the reference sequence. In some cases, alignment simply tells whether or not a read is a member of a particular reference sequence (i.e., whether the read is present or absent in the reference sequence). For example, the alignment of a read to the reference sequence for human chromosome 13 will tell whether the read is present in the reference sequence for chromosome 13. A tool that provides this information may be called a set membership tester. In some cases, an alignment additionally indicates a location in the reference sequence where the read or tag maps to. For example, if the reference sequence is the whole human genome sequence, an alignment may indicate that a read is present on chromosome 13, and may further indicate that the read is on a particular strand of chromosome 13.

A "site" is a unique position in a reference sequence corresponding to a read or tag. In certain embodiments, it specifies the identity of a chromosome (e.g., chromosome 13), a strand of the chromosome, and an exact position in the chromosome.

"polymorphic site" is a locus at which nucleotide sequence divergence occurs. The locus may be as small as one base pair. Illustrative markers have at least two alleles, each occurring at frequency of greater than 1%, and more typically greater than 10% or 20% of a selected population. A polymorphic site may be as small as one base pair. The terms "polymorphic locus" and "polymorphic site" are herein used interchangeably.

"polymorphic sequence" herein refers to a nucleic acid sequence e.g. a DNA sequence, that comprises one or more polymorphic sites e.g one SNP or a tandem SNP. Polymorphic sequences according to the present technology can be used to specifically differentiate between maternal and non-maternal alleles in the maternal sample comprising a mixture of fetal and maternal nucleic acids.

Detailed Embodiments

Typically, the processes described herein employ a reference sequence that spans one or more polymorphisms and is associated with the DNA being sampled. A reference sequence may be, for example, the human genome, a chromosome, or a region in a chromosome. One or more of the polymorphisms can be designated for the purpose of estimating fetal DNA fraction. Polymorphisms that are designated for use in determining fetal fraction are polymorphisms that are pre-known. For example, a comprehensive listing of references, facts and sequence information on pre-known STRs, and related population data are compiled in STRBase, which may be accessed via the World Wide Web at ibm4.carb.nist.gov:8800/dna/home.htm. Sequence information from GenBank® (http://www2.ncbi.nlm.nih.gov/cgi-bin/genbank) for commonly used STR loci is also accessible through STRBase. Information of pre-known SNPs can be accessed via are available from publicly accessible databases including, but not limited to Human SNP Database at world wide web address wi.mit.edu, NCBI dbSNP Home Page at world wide web address ncbi.nlm.nih.gov, world wide web address lifesciences.perkinelmer.com, Applied Biosystems by Life Technologies™ (Carlsbad, Calif.) at world wide web address appliedbiosystems.com, Celera Human SNP database at world wide web address celera.com, the SNP Database of the Genome Analysis Group (GAN) at world wide web address gan- .iarc.fr. In one embodiment, the SNPs designated for determining fetal fraction are selected from the group of 92 individual identification SNPs (IISNPs) described by Pakstis el al. (Pakstis et el. Hum Genet 127:315-324 [2010]), which have been shown to have a very small variation in frequency across populations ($F_{st}$<0.06), and to be highly informative around the world having an average heterozygosity≥0.4. SNPs that are encompassed by the method of the invention include linked and unlinked SNPs. To designate suitable tandem SNP sequences, the International HapMap Consortium database can be searched (The International HapMap Project, Nature 426:789-796 [2003]). The database is available on the world wide web at hapmap.org.

The polymorphisms so employed may be panels of preknown polymorphisms designated for determining fetal DNA fraction or they may be found by chance in an analysis of maternal DNA for other purposes such as mapping sample DNA tags to chromosomes.

In certain embodiments, the method comprises sequencing DNA in a sample using a mixture of genomes e.g. a maternal sample comprising fetal and maternal cell-free DNA, to provide a plurality of sequence tags that map to sequences comprising pre-known polymorphic sites on a reference genome, and using the tags mapped at the pre-known sites to determine the fetal fraction as described in detail below. Alternatively, following sequencing of the DNA, the sequence tags that are obtained by the sequencing technology e.g. NGS, are mapped to a reference genome, e.g. hg19, and sequence tags mapping to sites at which polymorphisms occur by chance i.e. not pre-known, are used to determine the fetal fraction.

The reference sequence to which sequence tags are mapped to pre-known polymorphic sites, can be a published reference genome or it can be an artificial database or other pre-defined collection of sequences for the polymorphisms under consideration. Each of the database sequences will span the one or more nucleotides associated with the polymorphism. As one example, see the list of polymorphism sequences presented below in "Appendix 1."

In various embodiments, the number of polymorphisms employed to estimate fetal DNA fraction is at least 2 polymorphisms, and more particularly for each of at least about 10 polymorphisms, and more preferably for each of at least about 100 polymorphisms.

In one example, SNP coverage and allele frequency are determined by aligning generated sequences to a reference genome constructed from combinatory expansion of the SNP definitions. The amplicon database contains bi-allelic variation information surrounded by, e.g., at least about 50 bases of flanking sequence. For example an amplicon with variation information string "[g/c]" (representing alternate alleles "g" and "c" may look like:

```
atcg . . . accg[g/c]ccgt . . .
```

In some cases, the procedure to input the amplicon database and generated sequences and output SNP/allele counts is as follows.
1. Create an allele search reference set from combinatorial expansion of the SNP definitions. For each sequence in the amplicon database, for each allele in the variation information string, create an allele sequence with the variation information string replaced by the allele.
   a. For example, considering the above example amplicon sequence two sequences would be created: 1) atcg . . . accgGccgt . . . And 2) atcg . . . accgCccgt . . . .
   b. An example of a full allele search reference set can be found in the Allele Search Database Sequence Listing.
2. Map sequences to the allele search reference set keeping only mappings that match only one sequence in the search set.
3. Allele count is determined by counting the number of sequences that match its allele sequence.

The methods disclosed herein assume a "normal" pregnancy, i.e., a pregnancy in which the mother is carrying only one fetus, and not twins, triplets, etc. Those of skill will appreciate modifications which account for non-normal pregnancies, particularly those in which the number of fetuses is known.

As indicated, when determining fetal fraction, the method sequences the DNA in the sample from maternal blood and counts the sequence tags that map to each sequence of polymorphism(s) under consideration. For each polymorphism, the method tallies the total number of reads that map to it (the coverage) and the numbers of sequence tags associated with each allele (the allele counts). In a simple example, a polymorphism having a coverage of 5, may have 3 reads of allele B and 2 reads of allele A. In this example, allele A is deemed the minor allele and allele B is deemed the major allele.

In some embodiments, this operation makes use of very fast sequencing tools such as massively parallel DNA sequencing tools. Examples of such tools are described in more detail below. In some cases, many thousands or millions of tag sequences are read for a single sample. Preferably, sequencing is performed in a manner that allows quick and direct assignment of sequenced DNA to particular predefined sequences harboring polymorphisms under consideration. Generally, there is sufficient information for this purpose in tags of size 30 base pairs or greater. Tags of this size can be unambiguously mapped to sequences of interest. In a specific embodiment, the tag sequences employed in the process are 36 base pairs in length.

The tags are mapped to a reference genome or to sequences in an allele sequence database (e.g., see Appendix 1 as previously mentioned) and the number of tags so mapped is determined. This will provide both the coverage and minor allele count for each polymorphism under consideration. In some cases, this may be done concurrently with mapping each tag to one of the 23 human chromosomes and determining the number of mapped tags per chromosome.

As mentioned, coverage is the total number of read sequences that map to a given polymorphism in a reference sequence. Allele count in the total number of read sequences mapping to such polymorphism that have an allele. The sum of all allele counts must equal the coverage. The allele with the highest count is the major allele, and the allele with the lowest count is the minor allele. In certain embodiments, the only information needed to estimate fetal DNA fraction is the coverage and minor allele count for each of a plurality of polymorphisms. In some embodiments, a base calling error rate of the DNA sequencing apparatus is also used.

It is useful to consider the mathematical or symbolic underpinnings of certain methods disclosed herein. As mentioned, in various examples, sequences generated from maternal blood are aligned (superimposed so that identical bases are maximized) to a reference genome or other nucleic acid sequence. Given a genomic position, j, and a set of sequences aligned to the reference, let the number of occurrences of each of the four DNA bases ("a", "t", "g", and "c", also called "alleles"), among the aligned sequences be w(j,1), w(j,2), w(j,3), and w(j,4) respectively. For the purposes of this discussion one may assume without loss of generality that all variations are bi-allelic. Hence the following notations may be used:

Major Allele Count at genomic position j as $B \equiv B_i = \{b_j\} \equiv w_{j,i}^{(1)} = \max_{i \in \{1,2,3,4\}}\{w_{j,i}\}$ as the first order statistic of counts at position j (The major allele, b, is the corresponding argmax. Subscripts are used when more than one SNP is being considered.)

Minor Allele Count at position j as $A \equiv A_i = \{a_j\} = w_{j,i}^{(2)}$ as the second order statistic of counts (i.e. the second highest allele count) at position j, Coverage at position j as $D \equiv D_j = \{d_i\} = A_j + B_j$, and Sequencing machine error rate is denoted e.

When the context is clear, for convenience notations are used interchangeably; for example, A, Ai, or {ai} may be used interchangeably for the minor allele or the minor allele count. Subscripts may or may not be used depending if more than one SNP is being considered. (SNPs are used for purposes of example only. Other types of polymorphisms may be used as discussed elsewhere herein).

In FIG. 1, the basis for the four states of polymorphism zygosity is depicted. As illustrated, the mother may be homo or heterozygous at a given polymorphism. Similarly, the baby may be either heterozygous or homozygous at the same position. As illustrated, cases 1 and 2 are the polymorphism cases in which the mother is homozygous. If the baby and the mother are both homozygous, the polymorphism is a case 1 polymorphism. As indicated above, this situation is typically not particularly interesting. If the mother is homozygous and the baby is heterozygous, the fetal fraction, f, is nominally given by two times the ratio of the minor allele to the coverage. In the polymorphism case where the mother is heterozygous and the baby is homozygous (case 3 in FIG. 1), the fetal fraction is nominally one minus two times the ratio of the minor allele to the coverage. Finally, in the case where both the mother and the fetus are heterozygous, the minor allele fraction should always be 0.5, barring error. The fetal fraction cannot be derived for polymorphisms falling into case 4.

The four cases will now be further elaborated.

Case 1: Mother and Baby Homozygous
In this case, baring sequencing error or contamination, no differences should be observed.

$$E(\text{min allele frequency}) = E(A) = 0.$$

Figure 3:
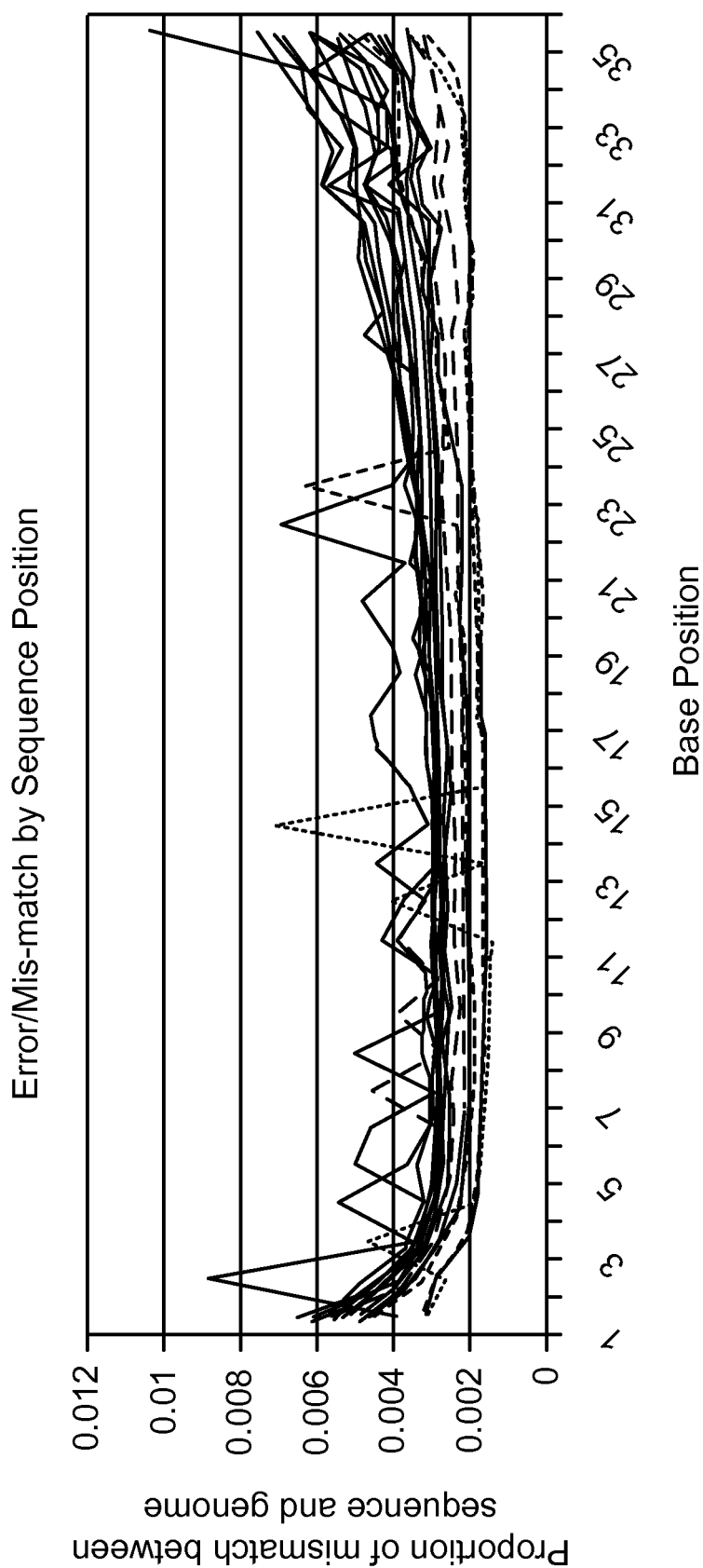
FIG. 3 presents error estimates by sequenced base position over 30 lanes of Illumina GA2 data aligned to human genome HG18 using Eland with default parameters.

In practice A~(is distributed as) a Binomial distribution which is approximated well by the Poisson distribution for low np. The distribution rate parameter for Binomial or Poisson is related to the sequencing error rate, e and the coverage D. FIG. 3 shows mismatch frequencies of generated 36mer sequences aligned to a Human reference genome.

This case contains no information about the fetal fraction. FIG. 3 presents error estimates by sequenced base position over 30 lanes of Illumina GA2 data aligned to Human Genome HG18 using Eland with default parameters.

Case 2: Mother Homozygous and Baby Heterozygous
In this case, for small fetal fraction (f), the observed allele frequencies will be markedly different. With the major allele usually occurring at frequency several times more than the minor allele.
Barring error, given a single SNP position (D,A), $E(A) = Df/2$ and an unbiased estimate for f is $2A/D$
Barring error, A~Binomial(f/2,D). Mean Df/2, Variance (1−f/2)Df/2. [Approximately Normal dist if D>15].

Case 3: Mother Heterozygous and Baby Homozygous
In this case the observed frequencies for major and minor alleles are close and A/D is just under 0.5.
Barring error, $E(A) = D(1-f)/2$, and $E(1-(2A/D)) = f$
Barring error, A~Binomial((1−f)/2, D). Mean D((1−f)/2), Variance $D/4(1-f^2)$.

Case 4: Mother Heterozygous and Baby Heterozygous
Note that, barring error, there are two sub-cases for this.
Case 4.1: The Allele from the Father is Different from the Mother's Alleles
This would introduce a third allele which would be the minor allele with $E(A) = Df/2$. These cases should not have an effect upon estimations for f because the procedure for assigning sequences to amplicons will filter out these cases when the reference SNPs are bi-allelic.
Case 4.2: The Allele from the Father Matches One of the Mother's Alleles
In this case, barring error, the two alleles would appear at 1:1 proportion so that this case is not useful for fetal fraction estimation.
Barring error, $E(A) = 0.5$, and A~Binomial(0.5,D) truncated at 0.5.

Figure 4:
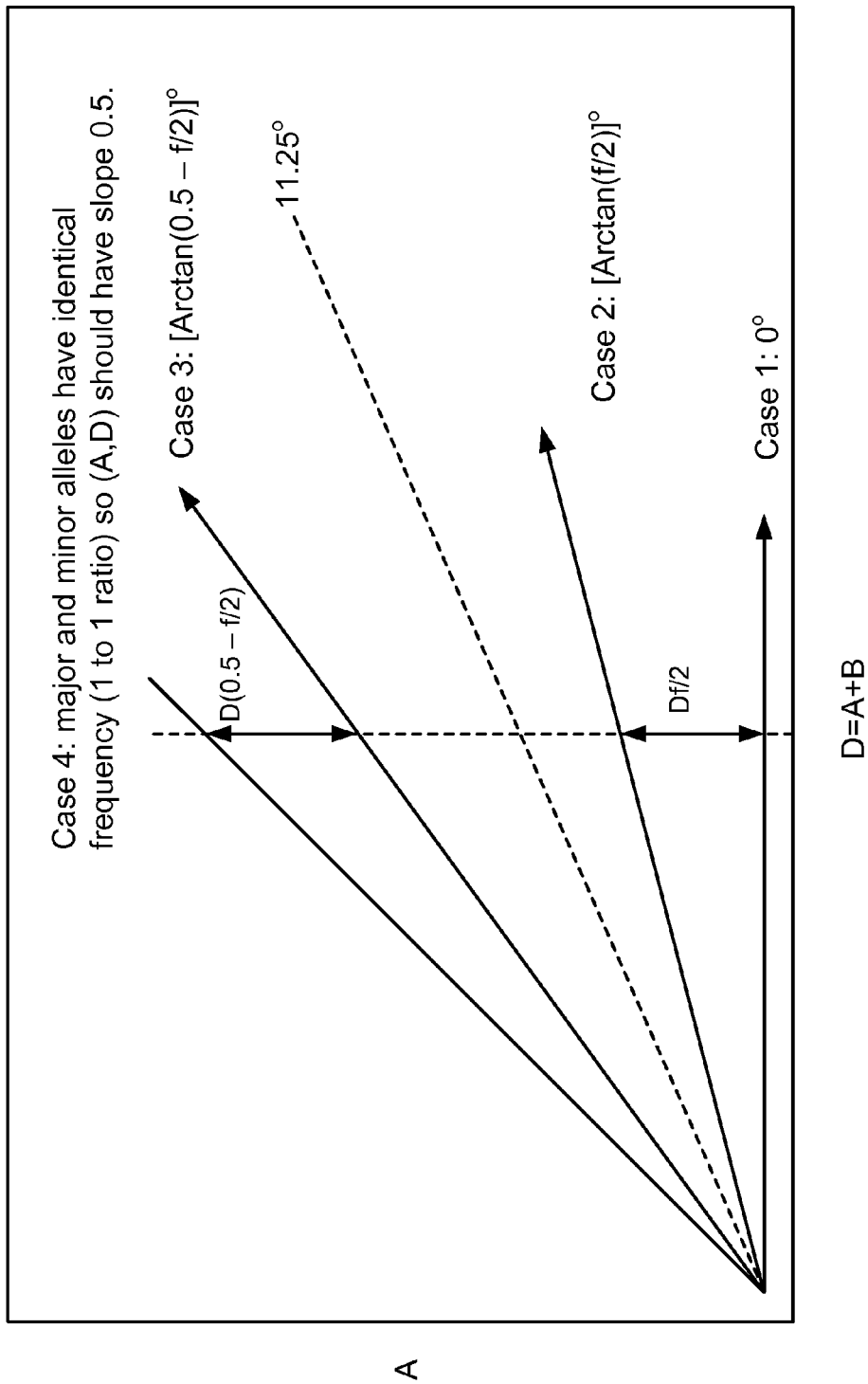
FIG. 4 is a plot of minor allele count A versus coverage D (assuming no error) for heterozygosity cases 1 through 4.

FIG. 4 presents a plot of minor allele count A versus coverage D (assuming no error) for heterozygosity cases 1 through 4.

In various embodiments, the method broadly concerns analyzing the allele frequency at one or more SNPs (or other polymorphisms) to classify the polymorphisms as being in either case 2 and/or case 3. Using the allele frequency in conjunction with the classification, the method can estimate the fetal fraction.

In some cases, given minor allele count A and coverage D, in other words a single point (D,A), for an individual SNP position allows methods to make a single point estimate. For example, certain methods classify a SNP with allele count (D,A) into a single case and derive a fetal fraction estimate as follows:

ES1.1 Simple Thresholds to Decide Case
Given an individual position (SNP),
1. Decide on case 1 with a decision function like 2A/D<e or a defined critical value of Binomial(e,D) or Poisson (De). One may also use an alternative distribution within the scope of this invention). No fetal fraction (f) estimate.
2. Decide on case 4 if 2A/D>(0.5−e) or some critical value of Binomial(0.5,D), (or other suitable approximating distribution). Do not use the position for an estimate of f.
3. Otherwise, decide on case 2 if 2A/D<0.25 (or some other manually set or automatically estimated threshold). Fetal fraction f estimated as 2A/D
4. Otherwise case 3. Use fetal fraction estimate f=(1−2A/D).

Accuracy can be gained by combining allele count information from several SNPs to estimate fetal fraction.

Method EM1: Combine Multiple SNPs by Averaging.
Take mean, median, other center measurement (for example: Tukey bi-weight, M-estimators, etc. . . . ). Weighted averages may also be used. For an example of how weights may be defined see EM2.4 below. Additionally robust measures of center may be used.

Method EM2 Simultaneous Estimation from Case 2 and Case 3 by Transformation
For occasions where f is less than X % case 3 points (D,A) can be transformed to be coincident with case 2 points. From this line a common slope can be calculated via regression through the origin (see FIG. 5).

One theoretical drawback of methods based on transformation is the case 2 and 3 binomial distributions will have different shape. At typical fetal fraction levels (<10%) case 2 data will have a distribution close to Poisson skewed to the right and case 3 will have a distribution close to normal.

Figure 5:
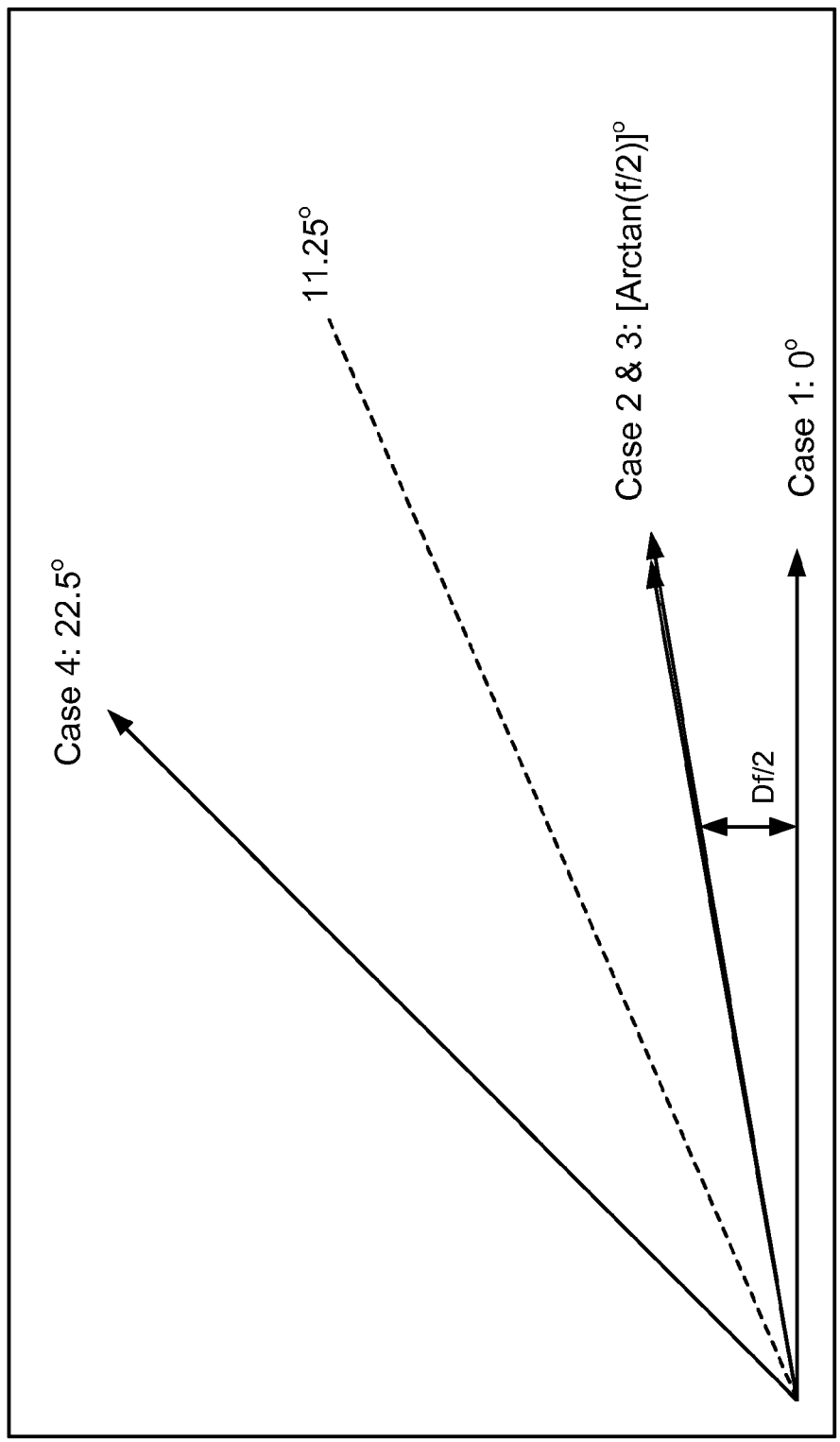
FIG. 5 depicts transformation of Case 3 data onto Case 2.

FIG. 5 depicts the transformation of Case 3 data onto Case 2. Now a single regression can estimate f from both cases simultaneously.

Method for Calculating EM2.3:

Step 1: Throw out Case 4 Data

For each data point (D,A) if A>(0.5D−T1) then exclude (D,A) from further analysis. T1(D,A) a real valued function.

Step 2: Transform Case 3 Data

Figure 6:
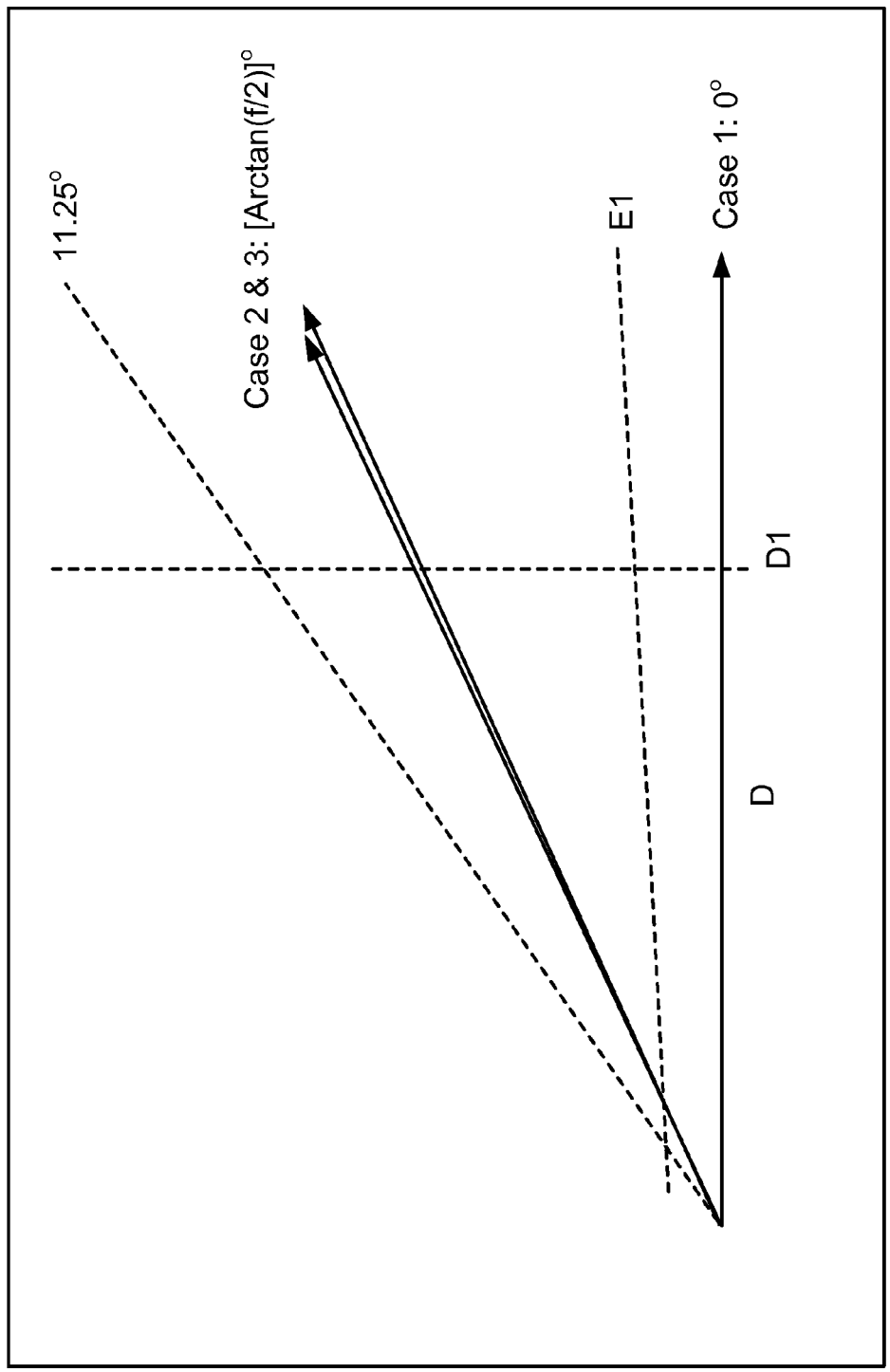
FIG. 6 presents post rotation data, in which D1 was selected so that case 1 and cases 2, 3 do not overlap. E1 represents an upper bound of the $99^{th}$ percent upper confidence interval of case 1 data.

See FIG. 6. For each data point (D, A) not ruled to be 4, if A >T2*D then transform to points to new coordinates (D1, A1). T2(D,A) a real valued function.

$$a=2A/D$$

$$A1=0.5D-A$$

$$D1=D$$

Step 3: Establish Threshold DT to Reduce Pollution from Case 1 Data

Disregard all data points below T2(D,A) a real valued function.

Step 4: Regression Estimate for Remaining Transformed Case 2 and 3 Data.

Apply regression through origin to remaining points. Fetal fraction estimate is twice the slope of the regression like.

Note that there are many classes of transformations that can be constructed to accomplish the same coincidence of case 2 and 3 data. Examples include trigonometric, transformation or use of rotation matrices. These deviations are intended to be included in the scope of this disclosure. Furthermore, many classes of regression (L2, L1, . . . ) or optimization can be used. Swapping the optimization algorithm is a trivial change and covered under the scope of this disclosure.

FIG. 6 presents post rotation data. Selecting D1 so that case 1 and cases 2 and 3 do not overlap. E1 represents an upper bound of the 99$^{th}$ percent upper confidence interval of case 1 data.

Method EM3 Weighted Least Squares

The regression method from EM2.3 assumes all of the translated data points have equal variance. It is more proper to account for the heteroskedasticity of the different data sources and even of points from the same heterozygosity pattern.

Steps 1 through 3 are identical to EM2.3.

Step 4: Regression

In the regression from EM2.3, the points from case 2 data will have variance v2(f,D)=[0.5*Df−0.25*D$f^2$] and points from case 3 data will have variance v3(f,D)= [0.25D(1−$f^2$)]. Assuming we give each point a different weight, w, as in EM2.3, we seek to minimize $$Q = \sum_{i=1}^{n} w_i(a_i - sd_i)^2 \qquad \text{Equation 1}$$

Setting first derivatives to zero and solving for s:

$$\frac{\partial Q}{\partial s} = \sum_{i=1}^{n} 2w_i(d_i - sa_i)(-a_i) = 0$$

$$\sum_{i=1}^{n} sa_i^2 - \sum_{i=1}^{n} 2w_i a_i x_i = 0$$

and $$s = \frac{\sum_{i=1}^{n} 2w_i d_i a_i}{\sum_{i=1}^{n} a_i^2}$$

where $d_i$ is the coverage of SNP $i$ and $a_i$ is the (transformed for case 3) minor allele count of SNP $i$.

Equation 2

This method weights with the inverse of the variance of each point, estimated as v2(2A/D,D), or v3(2A/D,D) as appropriate. The fetal fraction estimate is 2*s.

In certain embodiments, a mixture model may be employed to classify a collection of polymorphisms into two or more of the zygosity cases and concurrently estimate the fetal DNA fraction from mean allele frequencies for each of these cases. Generally, a mixture model assumes that a particular collection of data is made up of a mixture of different types of data, each of which has its own expected distribution (e.g., a normal distribution). The process attempts to find the mean and possibly other characteristics for each type of data. In embodiments disclosed herein, there are up to four different data types (the zygosity cases) that make the up the minor allele frequency data for the polymorphisms under consideration.

One implementation of a mixture model is presented in the following section. In this embodiment, the minor allele frequency A is a sum of four terms as shown in equation 3. Each of the terms corresponds to one of the four zygosity cases. Each term is the product of a polymorphism fraction and a binomial distribution of the minor allele frequency. The as are the fractions of the polymorphisms falling into each of the four cases. Each binominal distribution has an associated probability, p, and coverage, d. The minor allele probability for case 2, for example, is given by f/2.

The disclosed embodiments make use of "factorial moments" for the allele frequency data under consideration. As is well known, a distribution's mean is the first moment. It is the expected value of the minor allele frequency. The variance is the second moment. It is calculated from the expectation value of the allele frequency squared.

The allele frequency data across all polymorphisms may be used to calculate factorial moments (a first factorial moment, a second factorial moment, etc.) as shown in equation 4. As indicated by these equations, the factorial moments are summations of terms over i, the individual polymorphisms in the data set, where there are n such polymorphisms in the data set. The terms being summed are functions of the minor allele counts, $a_i$, and coverages $d_i$.

Usefully, the factorial moments have relationships with the values of $\alpha_i$ and $p_i$ as illustrated in equation 5. From the probabilities, $p_i$, one can determine the fetal fraction, f. For example, $p_2$=f/2 and $p_3$ is 1−f/2. Thus, the responsible logic can solve a system of equations relating the unknown αs and ps to the factorial moment expressions for minor allele fractions across the multiple polymorphisms under consideration. Of course, there are other techniques for solving the mixture models within the scope of this invention.

It is useful to further consider the mathematical or symbolic underpinnings of mixture model embodiments disclosed herein. The four heterozygosity cases described above suggest the following Binomial mixture model for the distribution of ai in points (ai,di):

$$A=\{a_i\} \sim \alpha_1 \text{Bin}(p_1,d_i) + \alpha_2 \text{Bin}(p_2,d_i) + \alpha_3 \text{Bin}(p_3,d_i) + \alpha_4 \text{Bin}(p_4,d_i)$$

where
$1 = \alpha_1 + \alpha_2 + \alpha_3 + \alpha_4$
$m = 4$
Equation 3

Various models for relating the $p_i$ to fetal fraction and sequencing error rates are described below. The parameters $\alpha_i$ relate to population specific parameters and the ability to let these values "float" give these methods additional robustness with respect to factors like ethnicity and progeny of the parents.

For various heterozygosity cases the equation above can be solved for fetal fraction. Perhaps the easiest method to solve for fetal fraction is through the method of factorial moments in which the mixture parameters can be expressed in terms of moments that can easily be estimated from the observed data.

Given n SNP positions, Factorial moments are defined as follows:

$$F_1 = \frac{1}{n}\sum_{i=1}^{n} \frac{a_i}{d_i}$$ Equation 4

$$F_2 = \frac{1}{n}\sum_{i=1}^{n} \frac{a_i(a_i-1)}{d_i(d_i-1)}$$

...

$$F_j = \frac{1}{n}\sum_{i=1}^{n} \frac{a_i(a_i-1)\cdots(a_i-j+1)}{d_i(d_i-1)(d_i-j+1)}$$

Factorial moments can be related to the $\{\alpha_i, p_i\}$ with $$F_1 \approx \sum_{i=1}^{m} \alpha_i p_i^1$$ Equation 5

$$F_2 \approx \sum_{i=1}^{m} \alpha_i p_i^2$$

...

$$F_j \approx \sum_{i=1}^{m} \alpha_i p_i^j$$

...

$$F_g \approx \sum_{i=1}^{m} \alpha_i p_i^g$$

A solution can be identified by solving for the $\{\alpha_i, p_i\}$ in a system of equations derived from the above relation Equation 5 when n>2*(number of parameters to be estimated). Obviously, the problem becomes much more difficult mathematically for higher g as more $\{\alpha_i, p_i\}$ need to be estimated.

It is typically not possible to accurately discriminate between case 1 and 2 (or case 3 and 4) data by simple thresholds at lower fetal fractions. Luckily for the use of reduced case models, case 1/2 data is easily separated from case 3/4 data by discriminating at point (2A/D)=T. Use of T=0.5 has been found to perform satisfactorily.

Note that the mixture model method employing equations 4 and 5 makes use of the data for all polymorphisms but does not separately account for the sequencing error. Appropriate methods that separate data for the first and second cases from data for the third and fourth cases can account for sequencing error.

In further examples, the data set provided to a mixture model contains data for only case 1 and case 2 polymorphisms. These are polymorphisms for which the mother is homozygous. A threshold technique may be employed to remove the case 3 and 4 polymorphisms. For example, polymorphisms with minor allele frequencies greater than a particular threshold are eliminated before employing the mixture model. Using appropriately filtered data and factorial moments as reduced to equations 7 and 8, one may calculate the fetal fraction, f, as shown in equation 9. Note that equation 7 is a restatement of equation 3 for this implementation of a mixture model. Note also that in this particular example, the sequencing error associated with the machine reading is not known. As a consequence, the system of equations must separately solve for the error, e.

Figure 7:
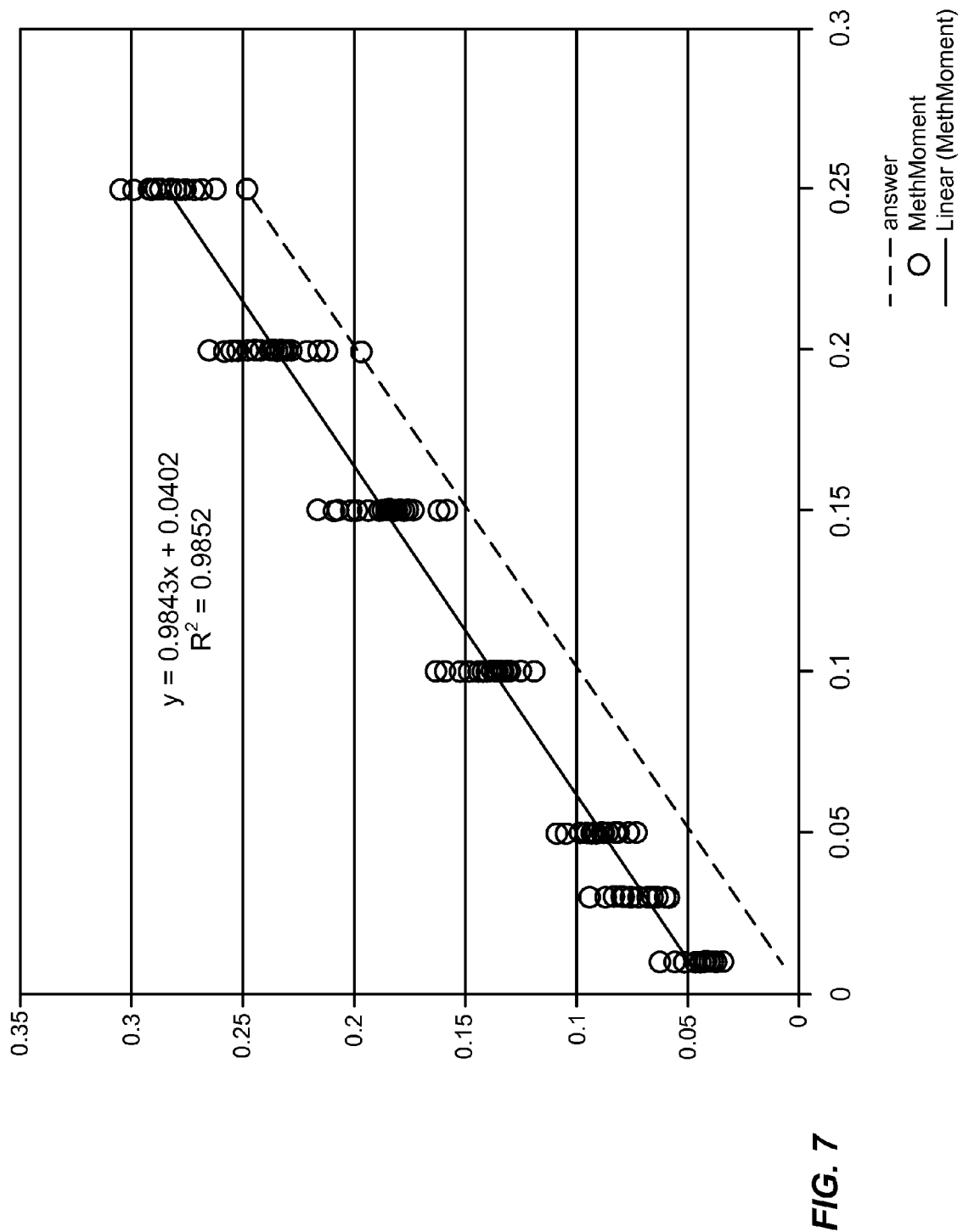
FIG. 7 shows a comparison of the results using a mixture model and the known fetal fraction and estimated fetal fraction.

FIG. 7 shows a comparison of the results using this mixture model and the known fetal fraction (x axis) and estimated fetal fraction. If the mixture model perfectly predicted the fetal fraction, the plotted results would follow the dashed line. Nevertheless, the estimated fractions are remarkably good, particularly considering that much of the data was eliminated prior to applying the mixture model.

To further elaborate, several other methods are available for parameter estimation of the model from Equation 3. In some cases tractable solution can be found by setting derivates to zero of the chi-squared statistic. In cases where no easy solution can be found by direct differentiation, taylor series expansion of the binomial PDF or other approximating polynomials can be effective. Minimum chi-square estimators are well-known to be efficient.

$$\chi^2(\alpha_i, p_i) = \sum_{i=1}^{n} \frac{(P_i - \sum \alpha_i \text{Binomial}(p_i, di))^2}{\text{Binomial}(n, p)}$$ Equation 6

Where Pi is the number of points of count i. An alternative method from Le Cam ["On the Asymptotic Theory of Estimation and Testing Hypotheses" Proceedings of the Third Berkeley Symposium on Mathematical Statistics and Probability, Volume 1 Berkeley Calif.: University of CA Press, 1956, pp. 129-156] uses Ralph-Newton iteration of the likelihood function. The method of moments solutions from Equation 5 can be used as a starting point for the iteration.

Under another application a method of resolving mixture models involving expectation maximization methods operating on mixtures of approximating Beta distributions is discussed.

Model Cases (1+2), Sequencing Error Unknown

Consider a reduced model that only accounts for heterozygosity cases 1 and 2. In this case the mixture distribution can be written as $$A=\{a_i\} \sim \alpha_i \text{Bin}(e,d_i) + \alpha_2 \text{Bin}(f/2,d_i)$$

where
$1 = \alpha_1 + \alpha_2$
$m = 4$
Equation 7
And the system $$F_1 = \alpha_1 e + (1-\alpha_1)(f/2)$$

$$F_2 = \alpha_1 e^2 + (1-\alpha_1)(f/2)^2$$

$$F_3 = \alpha_1 e^3 + (1-\alpha_1)(f/2)^3 \quad \text{Equation 8}$$

is solved for the e (sequencing error rate), alpha (proportion of case 1 points), and f (fetal fraction). Where the Fi are defined as in Equation 4 above. A closed form solution for fetal fraction is chosen to be the real solution of $$F \approx \frac{(F1-1)F2 \pm \sqrt{F2}\sqrt{4F1^3 + F2 - 3F1(2+F1)F2 + 4F2^2}}{2(F1^2 - F2)} \quad \text{Equation 9}$$

that is between 0 and 1.

To gauge the performance of estimators a simulated data-set of Hardy-Weinberg Equilibrium points (ai,di) was constructed with fetal fraction designed to be {1%, 3%, 5%, 10%, 15%, 20%, and 25%} and a constant sequencing error rate of 1%. The 1% error rate is the currently accepted rate for the sequencing machines and protocols we are using and is consistent with the graph of Illumina Genome analyzer II data shown in FIG. 3 above. Equation 9 was applied to the data and found, with the exception of a four point bias upwards, general agreement with the "known" fetal fraction. Interestingly, the sequencing error rate, e, is estimated to be just above 1%.

Figure 8:
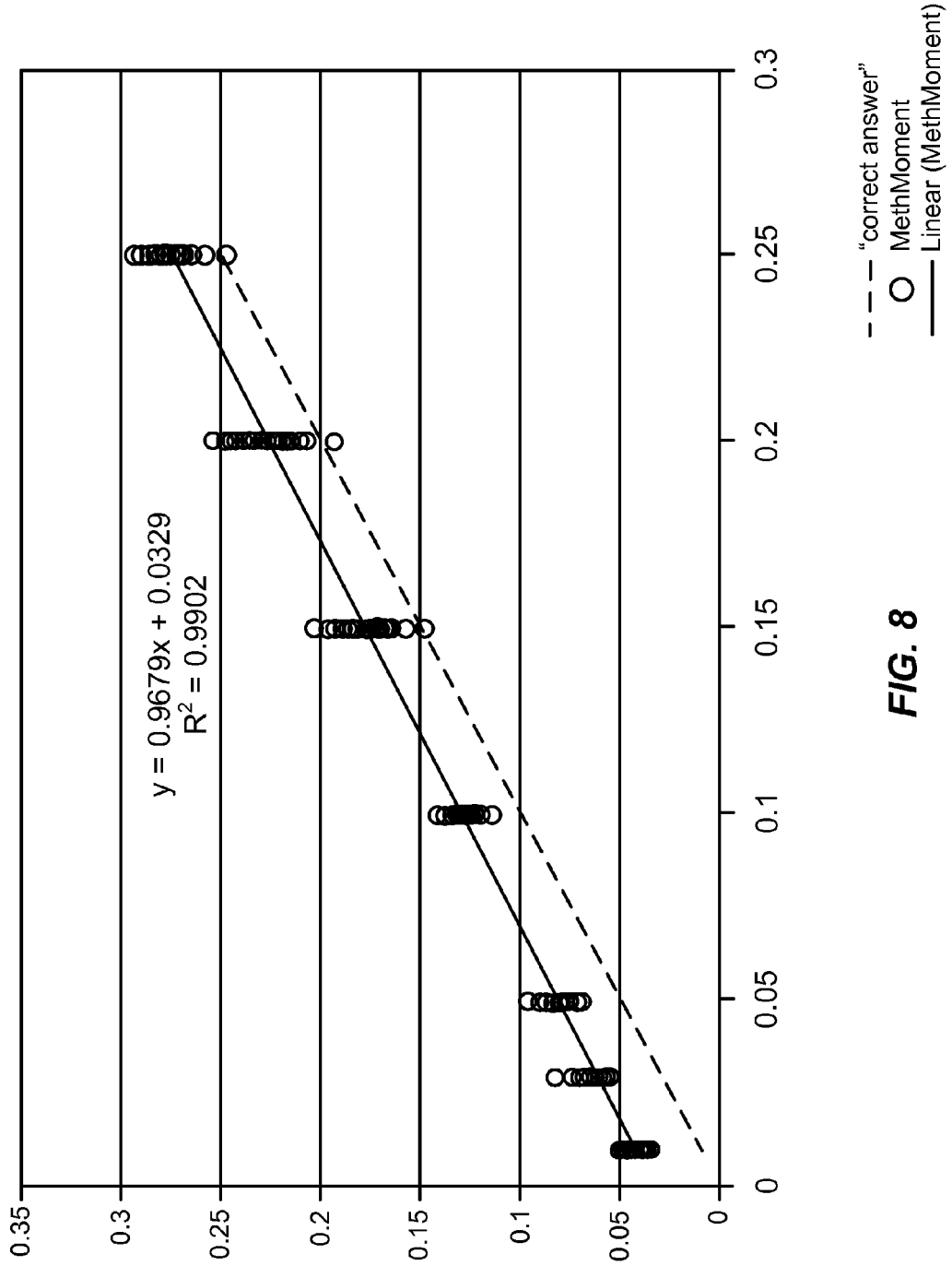
FIG. 8 shows that using the machine error rate as a known parameter reduces the upward bias by a point.

In the next mixture model example, thresholding or other filtering technique is again employed to remove data for polymorphisms falling into cases 3 and 4. However in this case, the sequencing error is known. This simplifies the resulting expression for fetal DNA fraction, f, as shown in equations 10. FIG. 8 shows that this version of a mixture model provided improved results compared to the approach employed with equation 9.

Figure 9:
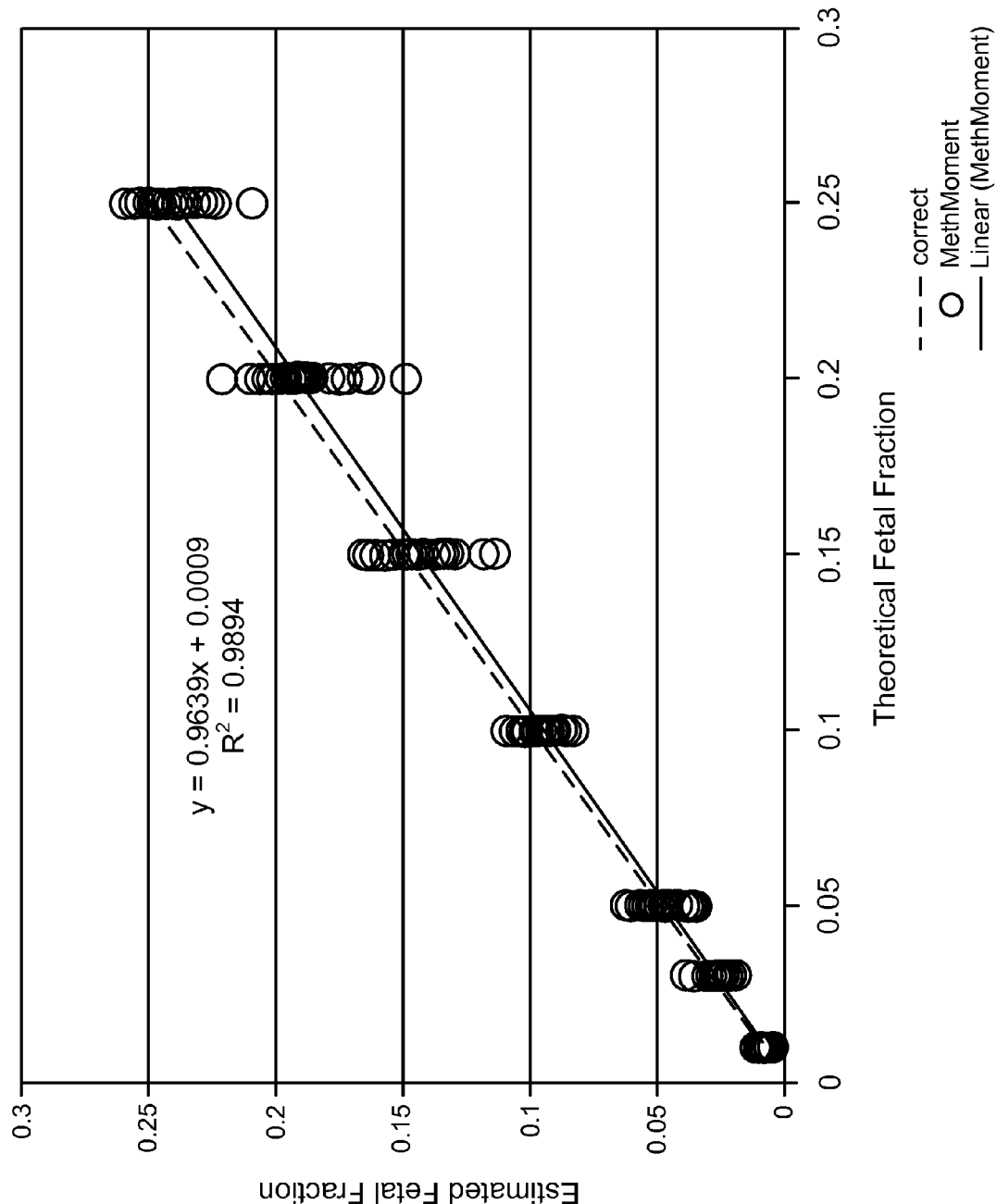
In FIG. 9 shows that simulated data using the machine error rate as a known parameter, enhancing the case 1 and 2 error models greatly reduces the upward bias to less than a point for fetal fraction below 0.2.

A similar approach is shown in equations 11 and 12. This approach recognizes that only some sequencing errors add the minor allele count. Rather only one in every four sequencing errors should increase the minor allele count. FIG. 9 shows remarkably good agreement between the actual and estimated fetal fractions using this technique.

Model Cases (1+2), Sequencing Error Known

Since the sequencing error rate of the machines used is known to a great extent, the bias and complexity of calculations can be reduced by eliminating e as a variable to be solved. Thus we obtain the system of equations $$F_1 = \alpha_1 e + (1-\alpha_1)(f/2)$$

$$F_2 = \alpha_1 e^2 + (1-\alpha_1)(f/2)^2 \quad \text{Equation 10}$$

for fetal fraction f to obtain the solution:

$$F \approx \frac{2(eF1 - F2)}{(e - F1)}$$

FIG. 8 shows that using the machine error rate as a known parameter reduces the upward bias by a point.

Model Cases (1+2), Sequencing Error Known, Improved Error Models

To ameliorate bias in the model we expanded the error model of the above equations to account for the fact that not every sequencing error event will add to minor allele count A=ai in heterozygosity case 1. Furthermore, we allow for the fact that sequencing error events may contribute to heterozygosity case 2 counts. Hence we determine fetal fraction F by solving for the following system of factorial moment relations:

$$F_1 = \alpha_1 e/4 + (1-\alpha_1)(e + f/2) \quad \text{Equation 11}$$

$$F_2 = \alpha_1 \left(\frac{e}{4}\right)^2 + (1-\alpha_1)(e + f/2)^2$$

which yields the solution $$F \approx \frac{-2(e^2 - 5eF1 + 4F2)}{(e - 4F1)}. \quad \text{Equation 12}$$

In FIG. 9 shows that simulated data using the machine error rate as a known parameter, enhancing the case 1 and 2 error models greatly reduces the upward bias to less than a point for fetal fraction below 0.2.

Implementation Options

Samples

Samples that are used in embodiments disclosed herein comprise genomic DNA that is cellular or cell-free. Cellular DNA is derived from whole cells by manually or mechanically extracting the genomic DNA from whole cells of the same or of differing genetic compositions. Cellular DNA can be derived for example, from whole cells of the same genetic composition derived from one subject, from a mixture of whole cells of different subjects, or from a mixture of whole cells that differ in genetic composition that are derived from one subject. Methods for extracting genomic DNA from whole cells are known in the art, and differ depending upon the nature of the source.

In some instances, it can be advantageous to fragment the cellular genomic DNA. Fragmentation can be random, or it can be specific, as achieved, for example, using restriction endonuclease digestion. Methods for random fragmentation are well known in the art, and include, for example, limited DNAse digestion, alkali treatment and physical shearing. In certain embodiments, the sample nucleic acids are subjected to fragmentation into fragments of approximately 500 or more base pairs, and to which next generation sequencing (NGS) methods can be readily applied. In one embodiment, sample nucleic acids are obtained from as cfDNA, which is not subjected to fragmentation.

Cell-free DNA is genomic DNA that naturally occurs as a mixture of genomic fragments typically found in biological fluids e.g. blood, of a subject. The genomic mixture can be derived from cells that naturally rupture to release their genomic content by biological processes e.g., apoptosis. A sample of cfDNA can comprise cfDNA derived from a mixture of cells of different subjects of the same species, from a mixture of cells from one subject that differ in genetic composition, or from a mixture of cells from different species e.g. a subject.

Cell-free nucleic acids, including cell-free DNA, can be obtained by various methods known in the art from biological samples including but not limited to plasma, serum and urine (Fan et al., Proc Natl Acad Sci 105:16266-16271 [2008]; Koide et al., Prenatal Diagnosis 25:604-607 [2005];

Chen et al., Nature Med. 2: 1033-1035 [1996]; Lo et al., Lancet 350: 485-487 [1997]; Botezatu et al., Clin Chem. 46: 1078-1084, 2000; and Su et al., J Mol. Diagn. 6: 101-107 [2004]). To separate cfDNA from cells, fractionation, centrifugation (e.g., density gradient centrifugation), DNA-specific precipitation, or high-throughput cell sorting and/or separation methods can be used. Commercially available kits for manual and automated separation of cfDNA are available (Roche Diagnostics, Indianapolis, Ind., Qiagen, Valencia, Calif., Macherey-Nagel, Duren, Del.).

The sample comprising the mixture of nucleic acids to which the methods described herein are applied may be a biological sample such as a tissue sample, a biological fluid sample, or a cell sample. In some embodiments, the mixture of nucleic acids is purified or isolated from the biological sample by any one of the known methods. A sample can be a purified or isolated polynucleotide. A biological fluid includes, as non-limiting examples, blood, plasma, serum, sweat, tears, sputum, urine, sputum, ear flow, lymph, saliva, cerebrospinal fluid, ravages, bone marrow suspension, vaginal flow, transcervical lavage, brain fluid, ascites, milk, secretions of the respiratory, intestinal and genitourinary tracts, amniotic fluid and leukophoresis samples. In some embodiments, the sample is a sample that is easily obtainable by non-invasive procedures e.g. blood, plasma, serum, sweat, tears, sputum, urine, sputum, ear flow, saliva or feces. Preferably, the biological sample is a peripheral blood sample, or the plasma and serum fractions. In other embodiments, the biological sample is a swab or smear, a biopsy specimen, or a cell culture. In another embodiment, the sample is a mixture of two or more biological samples e.g. a biological sample can comprise two or more of a biological fluid sample, a tissue sample, and a cell culture sample. As used herein, the terms "blood," "plasma" and "serum" expressly encompass fractions or processed portions thereof. Similarly, where a sample is taken from a biopsy, swab, smear, etc., the "sample" expressly encompasses a processed fraction or portion derived from the biopsy, swab, smear, etc.

In some embodiments, samples can be obtained from sources, including, but not limited to, samples from different individuals, different developmental stages of the same or different individuals, different diseased individuals (e.g., individuals with cancer or suspected of having a genetic disorder), normal individuals, samples obtained at different stages of a disease in an individual, samples obtained from an individual subjected to different treatments for a disease, samples from individuals subjected to different environmental factors, or individuals with predisposition to a pathology, or individuals with exposure to an infectious disease agent (e.g., HIV).

In one embodiment, the sample is a maternal sample that is obtained from a pregnant female, for example a pregnant woman. In this instance, the sample can be analyzed using the methods described herein to provide a prenatal diagnosis of potential chromosomal abnormalities in the fetus. The maternal sample can be a tissue sample, a biological fluid sample, or a cell sample. A biological fluid includes, as non-limiting examples, blood, plasma, serum, sweat, tears, sputum, urine, sputum, ear flow, lymph, saliva, cerebrospinal fluid, ravages, bone marrow suspension, vaginal flow, transcervical lavage, brain fluid, ascites, milk, secretions of the respiratory, intestinal and genitourinary tracts, and leukophoresis samples. In another embodiment, the maternal sample is a mixture of two or more biological samples e.g. a biological sample can comprise two or more of a biological fluid sample, a tissue sample, and a cell culture sample. In some embodiments, the sample is a sample that is easily obtainable by non-invasive procedures e.g. blood, plasma, serum, sweat, tears, sputum, urine, sputum, ear flow, saliva and feces. In some embodiments, the biological sample is a peripheral blood sample, or the plasma and serum fractions. In other embodiments, the biological sample is a swab or smear, a biopsy specimen, or a cell culture.

Samples can also be obtained from in vitro cultured tissues, cells, or other polynucleotide-containing sources. The cultured samples can be taken from sources including, but not limited to, cultures (e.g., tissue or cells) maintained in different media and conditions (e.g., pH, pressure, or temperature), cultures (e.g., tissue or cells) maintained for different periods of length, cultures (e.g., tissue or cells) treated with different factors or reagents (e.g., a drug candidate, or a modulator), or cultures of different types of tissue or cells. Methods of isolating nucleic acids from biological sources are well known and will differ depending upon the nature of the source as explained above.

Polymorphisms for Use in Identifying Genomic Fraction

As explained, polymorphisms may be used to assess the fetal fraction. The allele fraction and zygosity of one or more polymorphisms is used in the assessment. Examples of useful polymorphisms include, without limitation, single nucleotide polymorphisms (SNPs), tandem SNPs, small-scale multi-base deletions or insertions, called IN-DELS (also called deletion insertion polymorphisms or DIPs), Multi-Nucleotide Polymorphisms (MNPs), Short Tandem Repeats (STRs), restriction fragment length polymorphisms (RFLPs), deletions, including microdeletions, insertions, including microinsertions, duplications, inversions, translocations, multiplications, complex multi-site variants, copy number variations (CNVs), and polymorphisms comprising any other change of sequence in a chromosome.

In some embodiments, polymorphisms that are used in the disclosed methods include SNPs and/or STRs. SNP polymorphisms can be single SNP, tandem SNPs. Single SNPs include individual SNPs, and tag SNPs i.e. SNPs present in a haplotype, and/or a haplotype block. In some embodiments, combinations of polymorphisms are used. For example, differences in copy number can be detected by comparison of a combination of polymorphic sequences comprising one or more SNPs and one or more STRs.

In general, any polymorphic site that can be encompassed by the reads generated by the sequencing methods described herein can be used to identify genomic fraction in samples comprising DNA of different genomes. Polymorphic sequences useful for practicing the methods of the invention are available from a variety of publicly accessible databases, which are continuously expanding. For example, useful databases include without limitation Human SNP Database at world wide web address wi.mit.edu, NCBI dbSNP Home Page at world wide web address ncbi.nlm.nih.gov, world wide web address lifesciences.perkinelmer.com, Celera Human SNP database at world wide web address celera.com, the SNP Database of the Genome Analysis Group (GAN) at world wide web address gan.iarc.fr, ATCC short tandem repeat (STR) database at world wide web address atcc.org, and the HapMap database at world wide web address hapmap.org.

The number of polymorphisms that can be used in a fetal fraction assessment can be at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 35, 40, 45, 50, 55, 60, 65, 70, 75, 80, 85, 90, 95, 100, 200, 300, 400, 500, 600, 700, 800, 900, 1000 or more. For example, it is estimated that the human genome comprises at least about 10 million SNPs. Therefore, the number of available polymorphisms that can be genotyped in a sample from a human subject can be at least about 10 million SNPs, as well as many other types of polymorphisms that are present in any one human genome. In some embodiments, identification of one or more polymorphisms in a first genome of a sample comprising a mixture of DNA e.g. cfDNA, of a first and a second genome is performed by whole genome sequencing using a NGS method as described herein. In some embodiments, the whole genome sequencing method is an NGS method that identifies the polymorphic sequences by massively parallel sequencing clonally amplified nucleic acid molecules or by massively parallel sequencing of single nucleic acid molecules i.e. single molecule sequencing.

Applications

The fraction of nucleic acid originating from each of two distinct genomic sources in a sample can be used for various purposes. In various embodiments described herein, the fraction of fetal DNA in cell free DNA of a material sample is used to facilitate prenatal diagnoses and to assist in making decisions concerning treatment of pregnancies. In other embodiments, the genomes under consideration are not maternal and fetal. Various examples of genomic sources for determining fractional genome presence are presented below.

Cell-free fetal DNA and RNA circulating in maternal blood can be used for the early non-invasive prenatal diagnosis (NIPD) of an increasing number of genetic conditions, both for pregnancy management and to aid reproductive decision-making. Small amounts of circulating fetal DNA are present in the maternal bloodstream during pregnancy (Lo et al., Lancet 350:485-487 [1997]). Thought to originate from dying placental cells, cell-free fetal DNA has been shown to consists of short fragments typically fewer than 200 bp in length Chan et al., Clin Chem 50:88-92 [2004]), which can be discerned as early as 4 weeks gestation (Illanes et al., Early Human Dev 83:563-566 [2007]), and known to be cleared from the maternal circulation within hours of delivery (Lo et al., Am J Hum Genet 64:218-224 [1999]). In addition to cfDNA, fragments of cell-free fetal RNA (cfRNA) can also be discerned in the maternal bloodstream, originating from genes that are transcribed in the fetus or placenta. The extraction and subsequent analysis of these fetal genetic elements from a maternal blood sample offers novel opportunities for NIPD.

As explained, the disclosed methods determine the fraction of a second genome in a biological sample. The methods optionally determine the presence or absence of a number of disorders in a blood sample comprising a mixture of DNA (such as cfDNA) of a first and a second genome. In some embodiments, determination the fetal fraction may comprise (a) genome sequencing at least a portion of the mixture of cfDNA to obtain a plurality of sequence tags; (b) determining in the plurality of sequence tags the presence or absence of multiple polymorphisms, and (c) associating the multiple polymorphisms with the first and/or second genome in the mixture. In preferred embodiments, the mixture is unenriched for the multiple polymorphisms. Identification of the multiple polymorphisms in the mixture of DNA is performed by comparing the sequence of the mapped tags obtained by the whole genome sequencing method to multiple reference polymorphisms, as described herein.

In embodiment disclosed above, the first genome is a fetal genome, and a second genome is a maternal genome. In another embodiment, the first genome is a genome of an unaffected cell and the second genome is a genome from an affected cell e.g. a cancer cell. In some embodiments, the affected and unaffected cells are derived from the same subject. For example, the affected cell can be a cell whose genome has been altered by a disorder. In some embodiments the disorder is a monogenic disorder. In other embodiments, the disorder is a polygenic disorder. Disorders can be identified by a single polymorphism e.g. a tag SNP, or by multiple polymorphisms present in a haplotype. In some embodiments, the multiple polymorphisms identified according to the present method are present in a haplotype block.

The disorders that can be identified with the aid of the present method are genetic disorders, which are illnesses caused at least in part by abnormalities in genes or chromosomes. Knowledge of a fetal fraction in a sample can assist in identifying such disorders in a prenatal context. Disorders identified by the present method include monogenic i.e. single gene, disorders and polygenic i.e. complex disorders. Single gene disorders include autosomal dominant, autosomal recessive, X-linked dominant, X-linked recessive, and Y-linked.

In autosomal dominant disorders, only one mutated copy of the gene will be necessary for a person to be affected by the disorder. Typically, an affected subject has one affected parent, and there is a 50% chance that the offspring will inherit the mutated gene. Conditions that are autosomal dominant sometimes have reduced penetrance, which means that although only one mutated copy is needed, not all individuals who inherit that mutation go on to develop the disease. Examples of autosomal dominant disorders that can be identified by the present method include without limitation familial hypercholesterolemia, hereditary spherocytosis, Marfan syndrome, neurofibromatosis type 1, hereditary nonpolyposis colorectal cancer, and hereditary multiple exostoses, and Huntington disease.

Autosomal recessive disorders detected using the present method include Sickle cell anemia, Cystic fibrosis, Tay-Sachs disease, Tay-Sachs disease, Mucopolysaccharidoses, Glycogen storage diseases, and Galactosemia. X-linked disorders detected by the present method include Duchenne muscular dystrophy and hemophilia. In autosomal recessive disorders, two copies of the gene must be mutated for a subject to be affected by an autosomal recessive disorder. An affected subject usually has unaffected parents who each carry a single copy of the mutated gene (and are referred to as carriers). Two unaffected people who each carry one copy of the mutated gene have a 25% chance with each pregnancy of having a child affected by the disorder. Examples of this type of disorder that can be identified by the present method include are cystic fibrosis, sickle-cell disease, Tay-Sachs disease, Niemann-Pick disease, spinal muscular atrophy, and Roberts syndrome. Certain other phenotypes, such as wet versus dry earwax, are also determined in an autosomal recessive fashion. X-linked dominant disorders are caused by mutations in genes on the X chromosome. Only a few disorders have this inheritance pattern, with a prime example being X-linked hypophosphatemic rickets. Males and females are both affected in these disorders, with males typically being more severely affected than females. Some X-linked dominant conditions such as Rett syndrome, incontinentiapigmenti type 2 and Aicardi syndrome are usually fatal in males, and are therefore predominantly seen in females. Exceptions to this finding are extremely rare cases in which boys with Klinefelter syndrome (47,XXY) also inherit an X-linked dominant condition and exhibit symptoms more similar to those of a female in terms of disease severity. The chance of passing on an X-linked dominant disorder differs between men and women. The sons of a man with an X-linked dominant disorder will all be unaffected (since they receive their father's Y chromosome), and his daughters will all inherit the condition. A woman with an X-linked dominant disorder has a 50% chance of having an affected fetus with each pregnancy, although it should be noted that in cases such as incontinentiapigmenti only female offspring are generally viable. In addition, although these conditions do not alter fertility per se, individuals with Rett syndrome or Aicardi syndrome rarely reproduce.

The present method can also facilitate identification of polymorphisms associated with X-linked disorders. X-linked recessive conditions are also caused by mutations in genes on the X chromosome. Males are more frequently affected than females, and the chance of passing on the disorder differs between men and women. The sons of a man with an X-linked recessive disorder will not be affected, and his daughters will carry one copy of the mutated gene. A woman who is a carrier of an X-linked recessive disorder ($X^R X^r$) has a 50% chance of having sons who are affected and a 50% chance of having daughters who carry one copy of the mutated gene and are therefore carriers. X-linked recessive conditions include without limitation the serious diseases Hemophilia A, Duchenne muscular dystrophy, and Lesch-Nyhan syndrome as well as common and less serious conditions such as male pattern baldness and red-green color blindness. X-linked recessive conditions can sometimes manifest in females due to skewed X-inactivation or monosomy X (Turner syndrome).

Y-linked disorders are caused by mutations on the Y chromosome. Because males inherit a Y chromosome from their fathers, every son of an affected father will be affected. Because females inherit an X chromosome from their fathers, female offspring of affected fathers are never affected. Since the Y chromosome is relatively small and contains very few genes, there are relatively few Y-linked disorders. Often the symptoms include infertility, which may be circumvented with the help of some fertility treatments. Examples are male infertility and hypertrichosis pinnae.

As explained the disclosed methods for detecting genomic fractions in a sample can be used to facilitate detection of aneuploidy from material samples. In some embodiments, the aneuploidy is a complete chromosomal trisomy or monosomy, or a partial trisomy or monosomy. Partial aneuploidies are caused by loss or gain of part of a chromosome, and encompass chromosomal imbalances resulting from unbalanced translocations, unbalanced inversions, deletions and insertions. By far, the most common known aneuploidy compatible with life is trisomy 21 i.e. Down Syndrome (DS), which is caused by the presence of part or all of chromosome 21. Rarely, DS can be cause by an inherited or sporadic defect whereby an extra copy of all or part of chromosome 21 becomes attached to another chromosome (usually chromosome 14) to form a single aberrant chromosome. DS is associated with intellectual impairment, severe learning difficulties and excess mortality caused by long-term health problems such as heart disease. Other aneuploidies with known clinical significance include Edward syndrome (trisomy 18) and Patau Syndrome (trisomy 13), which are frequently fatal within the first few months of life. Abnormalities associated with the number of sex chromosomes are also known and include monosomy X e.g. Turner syndrome (XO), and triple X syndrome (XXX) in female births and Kleinefelter syndrome (XXY) and XYY syndrome in male births, which are all associated with various phenotypes including sterility and reduction in intellectual skills. Monosomy X [45,X] is a common cause of early pregnancy loss accounting for about 7% of spontaneous abortions. Based on the liveborn frequency of 45,X (also called Turner syndrome) of 1-2/10,000, it is estimated that less than 1% of 45,X conceptuses will survive to term. About 30% of Turners syndrome patients are mosaic with both a 45,X cell line and either a 46,XX cell line or one containing a rearranged X chromosome (Hook and Warburton 1983). The phenotype in a liveborn infant is relatively mild considering the high embryonic lethality and it has been hypothesized that possibly all liveborn females with Turner syndrome carry a cell line containing two sex chromosomes. Monosomy X can occur in females as 45,X or as 45,X/46XX, and in males as 45,X/46XY. Autosomal monosomies in human are generally suggested to be incompatible with life; however, there is quite a number of cytogenetic reports describing full monosomy of one chromosome 21 in live born children (Vosranoval et al., Molecular Cytogen. 1:13 [2008]; Joosten et al., Prenatal Diagn. 17:271-5 [1997]. The method of the invention can be used to diagnose these and other chromosomal abnormalities prenatally.

According to some embodiments, fetal fraction can useful in determining the presence or absence of chromosomal trisomies of any one of chromosomes 1-22, X and Y. Examples of chromosomal trisomies that can be detected according to the present method include without limitation trisomy 21 (T21; Down Syndrome), trisomy 18 (T18; Edward's Syndrome), trisomy 16 (T16), trisomy 20 (T20), trisomy 22 (T22; Cat Eye Syndrome), trisomy 15 (T15; PraderWilli Syndrome), trisomy 13 (T13; Patau Syndrome), trisomy 8 (T8; Warkany Syndrome), trisomy 9, and the XXY (Kleinefelter Syndrome), XYY, or XXX trisomies. Complete trisomies of other autosomes existing in a non-mosaic state are lethal, but can be compatible with life when present in a mosaic state. It will be appreciated that various complete trisomies, whether existing in a mosaic or non-mosaic state, and partial trisomies can be determined in fetal cfDNA according to the teachings of the present invention.

Non-limiting examples of partial trisomies that can be determined by the present method include, but are not limited to, partial trisomy 1q32-44, trisomy 9 p, trisomy 4 mosaicism, trisomy 17p, partial trisomy 4q26-qter, partial 2p trisomy, partial trisomy 1q, and/or partial trisomy 6p/monosomy 6q.

The methods disclosed herein can also be used to help determine chromosomal monosomy X, chromosomal monosomy 21, and partial monosomies such as, monosomy 13, monosomy 15, monosomy 16, monosomy 21, and monosomy 22, which are known to be involved in pregnancy miscarriage. Partial monosomy of chromosomes typically involved in complete aneuploidy can also be determined by the method of the invention. Non-limiting examples of deletion syndromes that can be determined according to the present method include syndromes caused by partial deletions of chromosomes. Examples of partial deletions that can be determined according to the method of the invention include without limitation partial deletions of chromosomes 1, 4, 5, 7, 11, 18, 15, 13, 17, 22 and 10, which are described in the following.

1q21.1 deletion syndrome or 1q21.1 (recurrent) microdeletion is a rare aberration of chromosome 1. Next to the deletion syndrome, there is also a 1q21.1 duplication syndrome. While there is a part of the DNA missing with the deletion syndrome on a particular spot, there are two or three copies of a similar part of the DNA on the same spot with the duplication syndrome. Literature refers to both the deletion and the duplication as the 1q21.1 copy-number variations (CNV). The 1q21.1 deletion can be associated with the TAR Syndrome (Thrombocytopenia with Absent radius).

Wolf-Hirschhorn syndrome (WHS) (OMIN #194190) is a contiguous gene deletion syndrome associated with a hemizygous deletion of chromosome 4p16.3. Wolf-Hirschhorn syndrome is a congenital malformation syndrome characterized by pre- and postnatal growth deficiency, developmental disability of variable degree, characteristic craniofacial features ('Greek warrior helmet' appearance of the nose, high forehead, prominent glabella, hypertelorism, high-arched eyebrows, protruding eyes, epicanthal folds, short philtrum, distinct mouth with downturned corners, and micrognathia), and a seizure disorder.

Partial deletion of chromosome 5, also known as 5p- or 5p minus, and named Cris du Chat syndrome (OMIN#123450), is caused by a deletion of the short arm (p arm) of chromosome 5 (5p15.3-p15.2). Infants with this condition often have a high-pitched cry that sounds like that of a cat. The disorder is characterized by intellectual disability and delayed development, small head size (microcephaly), low birth weight, and weak muscle tone (hypotonia) in infancy, distinctive facial features and possibly heart defects.

Williams-Beuren Syndrome also known as chromosome 7q11.23 deletion syndrome (OMIN 194050) is a contiguous gene deletion syndromeresulting in a multisystem disorder caused by hemizygous deletion of 1.5 to 1.8 Mb on chromosome 7q11.23, which contains approximately 28 genes.

Jacobsen Syndrome, also known as 11q deletion disorder, is a rare congenital disorder resulting from deletion of a terminal region of chromosome 11 that includes band 11q24.1. It can cause intellectual disabilities, a distinctive facial appearance, and a variety of physical problems including heart defects and a bleeding disorder.

Partial monosomy of chromosome 18, known as monosomy 18p is a rare chromosomal disorder in which all or part of the short arm (p) of chromosome 18 is deleted (monosomic). The disorder is typically characterized by short stature, variable degrees of mental retardation, speech delays, malformations of the skull and facial (craniofacial) region, and/or additional physical abnormalities. Associated craniofacial defects may vary greatly in range and severity from case to case.

Conditions caused by changes in the structure or number of copies of chromosome 15 include Angelman Syndrome and Prader-Willi Syndrome, which involve a loss of gene activity in the same part of chromosome 15, the 15q11-q13 region. It will be appreciated that several translocations and microdeletions can be asymptomatic in the carrier parent, yet can cause a major genetic disease in the offspring. For example, a healthy mother who carries the 15q11-q13 microdeletion can give birth to a child with Angelman syndrome, a severe neurodegenerative disorder. Thus, the present invention can be used to identify such a partial deletion and other deletions in the fetus.

Partial monosomy 13q is a rare chromosomal disorder that results when a piece of the long arm (q) of chromosome 13 is missing (monosomic). Infants born with partial monosomy 13q may exhibit low birth weight, malformations of the head and face (craniofacial region), skeletal abnormalities (especially of the hands and feet), and other physical abnormalities. Mental retardation is characteristic of this condition. The mortality rate during infancy is high among individuals born with this disorder. Almost all cases of partial monosomy 13q occur randomly for no apparent reason (sporadic).

Smith-Magenis syndrome (SMS—OMIM #182290) is caused by a deletion, or loss of genetic material, on one copy of chromosome 17. This well-known syndrome is associated with developmental delay, mental retardation, congenital anomalies such as heart and kidney defects, and neurobehavioral abnormalities such as severe sleep disturbances and self-injurious behavior. Smith-Magenis syndrome (SMS) is caused in most cases (90%) by a 3.7-Mb interstitial deletion in chromosome 17p11.2.

22q11.2 deletion syndrome, also known as DiGeorge syndrome, is a syndrome caused by the deletion of a small piece of chromosome 22. The deletion (22 q11.2) occurs near the middle of the chromosome on the long arm of one of the pair of chromosome. The features of this syndrome vary widely, even among members of the same family, and affect many parts of the body. Characteristic signs and symptoms may include birth defects such as congenital heart disease, defects in the palate, most commonly related to neuromuscular problems with closure (velo-pharyngeal insufficiency), learning disabilities, mild differences in facial features, and recurrent infections. Microdeletions in chromosomal region 22q11.2 are associated with a 20 to 30-fold increased risk of schizophrenia.

Deletions on the short arm of chromosome 10 are associated with a DiGeorge Syndrome like phenotype. Partial monosomy of chromosome 10p is rare but has been observed in a portion of patients showing features of the DiGeorge Syndrome.

In one embodiment, the method of the invention is used to determine partial monosomies including but not limited to partial monosomy of chromosomes 1, 4, 5, 7, 11, 18, 15, 13, 17, 22 and 10, e.g. partial monosomy 1q21.11, partial monosomy 4p16.3, partial monosomy 5p15.3-p15.2, partial monosomy 7q11.23, partial monosomy 11q24.1, partial monosomy 18p, partial monosomy of chromosome 15 (15q11-q13), partial monosomy 13q, partial monosomy 17p11.2, partial monosomy of chromosome 22 (22q11.2), and partial monosomy 10p can also be determined using the method.

Other partial monosomies that can be determined according to the method of the invention include unbalanced translocation t(8;11)(p23.2;p15.5); 11q23 microdeletion; 17p11.2 deletion; 22q13.3 deletion; Xp22.3 microdeletion; 10p14 deletion; 20p microdeletion, [del(22)(q11.2q11.23)], 7q11.23 and 7q36 deletions; 1p36 deletion; 2p microdeletion; neurofibromatosis type 1 (17q11.2 microdeletion), Yq deletion; 4p16.3 microdeletion; 1p36.2 microdeletion; 11q14 deletion; 19q13.2 microdeletion; Rubinstein-Taybi (16 p13.3 microdeletion); 7p21 microdeletion; Miller-Dieker syndrome (17p13.3); and 2q37 microdeletion. Partial deletions can be small deletions of part of a chromosome, or they can be microdeletions of a chromosome where the deletion of a single gene can occur.

Several duplication syndromes caused by the duplication of part of chromosome arms have been identified (see OMIN [Online Mendelian Inheritance in Man viewed online at ncbi.nlm.nih.gov/omim]) In one embodiment, the present method can be used to determine the presence or absence of duplications and/or multiplications of segments of any one of chromosomes 1-22, X and Y. Non-limiting examples of duplications syndromes that can be determined according to the present method include duplications of part of chromosomes 8, 15, 12, and 17, which are described in the following.

8p23.1 duplication syndrome is a rare genetic disorder caused by a duplication of a region from human chromosome 8. This duplication syndrome has an estimated prevalence of 1 in 64,000 births and is the reciprocal of the 8p23.1 deletion syndrome. The 8p23.1 duplication is associated with a variable phenotype including one or more of speech delay, developmental delay, mild dysmorphism, with prominent forehead and arched eyebrows, and congenital heart disease (CHD).

Chromosome 15q Duplication Syndrome (Dup15q) is a clinically identifiable syndrome which results from duplications of chromosome 15q11-13.1 Babies with Dup15q usually have hypotonia (poor muscle tone), growth retardation; they may be born with a cleft lip and/or palate or malformations of the heart, kidneys or other organs; they show some degree of cognitive delay/disability (mental retardation), speech and language delays, and sensory processing disorders.

Pallister Killian syndrome is a result of extra #12 chromosome material. There is usually a mixture of cells (mosaicism), some with extra #12 material, and some that are normal (46 chromosomes without the extra #12 material). Babies with this syndrome have many problems including severe mental retardation, poor muscle tone, "coarse" facial features, and a prominent forehead. They tend to have a very thin upper lip with a thicker lower lip and a short nose. Other health problems include seizures, poor feeding, stiff joints, cataracts in adulthood, hearing loss, and heart defects. Persons with Pallister Killian have a shortened lifespan.

Individuals with the genetic condition designated as dup (17)(p11.2p11.2) or dup 17p carry extra genetic information (known as a duplication) on the short arm of chromosome 17. Duplication of chromosome 17p11.2 underlies Potocki-Lupski syndrome (PTLS), which is a newly recognized genetic condition with only a few dozen cases reported in the medical literature. Patients who have this duplication often have low muscle tone, poor feeding, and failure to thrive during infancy, and also present with delayed development of motor and verbal milestones. Many individuals who have PTLS have difficulty with articulation and language processing. In addition, patients may have behavioral characteristics similar to those seen in persons with autism or autism-spectrum disorders. Individuals with PTLS may have heart defects and sleep apnea. A duplication of a large region in chromosome 17p12 that includes the gene PMP22 is known to cause Charcot-Marie Tooth disease.

CNV have been associated with stillbirths. However, due to inherent limitations of conventional cytogenetics, the contribution of CNV to stillbirth is thought to be underrepresented (Harris et al., Prenatal Diagn 31:932-944 [2011]). The present methods are useful in assisting determination of the presence of partial aneuploidies e.g. deletions and multiplications of chromosome segments, and can be used to help identify and determine the presence or absence of CNV that are associated with stillbirths.

The present method can also assist in identifying polymorphisms associated with genetic disorders that are complex, multifactorial, or polygenic, meaning that they are likely associated with the effects of multiple genes in combination with lifestyle and environmental factors. Multifactorial disorders include for example, heart disease and diabetes. Although complex disorders often cluster in families, they do not have a clear-cut pattern of inheritance. On a pedigree, polygenic diseases do tend to "run in families", but the inheritance does is not simple as is with Mendelian diseases. Strong environmental components are associated with many complex disorders e.g., blood pressure. The present method can be used to identify polymorphisms that are associated with polygenic disorders including but not limited to asthma, autoimmune diseases such as multiple sclerosis, cancers, ciliopathies, cleft palate, diabetes, heart disease, hypertension, inflammatory bowel disease, mental retardation, mood disorder, obesity, refractive error, and infertility. In some embodiments, the polymorphisms are SNPs. In other embodiments, the polymorphisms are STRs. In yet other embodiments, the polymorphisms are a combination of SNPs and STRs.

In one embodiment, identification of the polymorphic sequences associated with disorders comprises sequencing at least a portion of the cellular genome corresponding to the second genome in the mixture of cfDNA. Identification of polymorphic sequences contributed by a first genome is performed by determining the sequence at multiple polymorphic sites in a first sample containing DNA molecules derived essentially from only a second genome, determining the sequence at the corresponding multiple polymorphic sites in a second sample containing a mixture of DNA molecules derived from a first and a second genome, and comparing the polymorphic sequences determined in both samples thereby identifying multiple polymorphisms in a first genome of a sample comprising a mixture of two genomes. For example, identification of polymorphic sequences contributed by a fetal genome i.e. first genome, is performed by determining the sequence at multiple polymorphic sites in a maternal buffy coat sample i.e. a sample containing DNA molecules derived essentially from only a second genome, determining the sequence at the corresponding multiple polymorphic sites in a purified plasma sample i.e. a second sample containing a mixture of cfDNA molecules derived from the fetal and the maternal genomes, and comparing the polymorphic sequences determined in both samples to identify multiple fetal polymorphisms. In one embodiment, the first genome is a fetal genome, and a second genome is a maternal genome. In another embodiment, the first genome is a genome of an unaffected cell and the second genome is a genome from an affected cell. In some embodiments, the affected and unaffected cells are derived from the same subject. For example, the affected cell can be a cell whose genome has been altered by a disorder.

In one embodiment, the disclosed methods of estimating genomic fraction assist in detecting cancer in a patient. In various examples, a cancer is detected by a method comprising: providing a sample from a patient comprising a mixture of genomes derived from normal i.e. unaffected, and cancerous i.e. affected, cells; and identifying multiple polymorphisms associated with cancer. In some embodiments, the sample is selected from blood, plasma, serum and urine. In some embodiments, the sample is a plasma sample. In other embodiments, the sample is a urine sample.

In one embodiment, identifying multiple polymorphisms associated with cancer comprises enriching the DNA in the sample for polymorphic target sequences. In other embodiments, enrichment of the sample for polymorphic target sequences is not performed. In some embodiments, identifying multiple polymorphisms associated with cancer comprises quantifying the number of copies of the polymorphic sequence.

Cancers that can be identified and/or monitored according to the method of the invention include solid tumors, as well as, hematologic tumors and/or malignancies. Various cancers to be treated include sarcomas, carcinomas, and adenocarcinomas not limited to breast cancer, lung cancer, colorectal cancer, pancreatic cancer, ovarian cancer, prostate cancer, renal carcinoma, hepatoma, brain cancer, melanoma, multiple myeloma, lymphoma, Hodgkin's lymphoma, non-Hodgkin's lymphoma, childhood lymphomas, and lymphomas of lymphocytic and cutaneous origin, leukemia, childhood leukemia, hairy-cell leukemia, acute lymphocytic leukemia, acute myelocytic leukemia, chronic lymphocytic leukemia, chronic myelocytic leukemia, chronic myelogenous leukemia, and mast cell leukemia, myeloid neoplasms, mast cell neoplasms, hematologic tumor, and lymphoid tumor, including metastatic lesions in other tissues or organs distant from the primary tumor site.

The methods of the present invention are useful, for example, in diagnosing or determining a prognosis in a disease condition known to be associated with a specific haplotype(s), to determine novel haplotypes, and to detect haplotype associations with responsiveness to pharmaceuticals. The association of multiple polymorphic sequences with multiple disorders can be determined from the identity of a single polymorphic sequence for each of the multiple disorders. Alternatively, association of multiple polymorphic sequences with multiple disorders can be determined from the identity of multiple polymorphic sequences for each of the multiple disorders.

Conventional genotyping techniques have been limited to identifying polymorphisms in short genomic regions of a few kilobases, and identification of haplotypes has relied on family data and statistical estimation using computational algorithms. Whole genome sequencing enables the identification of haplotypes by directly identifying the polymorphisms on a genome. The identification of the haplotypes according to various embodiments is not limited by the intervening distance between polymorphisms. In some embodiments, a method comprises whole genome sequencing maternal cellular DNA. Maternal cellular DNA can be obtained from a biological sample devoid of fetal genomic DNA. For example, maternal DNA can be obtained from the buffy coat layer of a maternal blood. Haplotypes comprising a plurality of polymorphic sequences that span entire chromosomes can be determined. In one embodiment, the fetal haplotypes are compared to known disorder-associated haplotypes, and based on a match of the fetal haplotype with any one of the known disorder-associated haplotypes indicates that the fetus has the disorder or that the fetus is susceptible for the disorder. Fetal haplotypes can also be compared to haplotypes associated with treatment responsiveness or unresponsiveness of the specific polymorphism. Comparison of the identified fetal haplotypes to known haplotype databases allow for the diagnosis and/or prognosis of a disorder. Any biological sample comprising a mixture of fetal and maternal cfDNA can be used to determine the presence or absence of the fetal disorder. Preferably, the biological sample is selected from blood, or fractions thereof including plasma, or urine. In one embodiment, the biological sample is a blood sample. In another embodiment, the biological sample is a plasma sample. In yet another embodiment, the biological sample is a urine sample.

In one embodiment, the invention provides a method for determining the presence or absence of multiple fetal disorders, comprising (a) obtaining a maternal blood sample comprising a cell-free mixture of fetal and maternal DNA, (b) whole genome sequencing at least a portion of the cell-free mixture of fetal and maternal DNA, thereby obtaining a plurality of sequence tags; (c) determining multiple fetal polymorphisms in the sequence tags, and (d) determining the presence or absence of multiple fetal disorders. Examples of multiple fetal disorders that can be identified according to the present method include monogenic and polygenic disorders described herein.

In one embodiment, the invention provides a method for determining the presence or absence of multiple fetal disorders that comprises identifying multiple fetal polymorphisms associated with multiple disorders related haplotypes. In some embodiments, each of the haplotypes comprises at least at least two, at least three, at least four, at least five, at least ten or at least fifteen different tag polymorphisms. The tag polymorphisms present in the haplotype can be of the same type of polymorphism e.g. all tag SNP polymorphisms, or can be a combination of polymorphisms e.g. tag SNPs and tag deletions. In one embodiment, the polymorphisms are tag SNPs. In another embodiment, the polymorphisms are tag STRs. In yet another embodiment, the polymorphisms are a combination of tag SNPs and tag STRs. The tag polymorphisms can be in coding and/or non-coding regions of the genome. Identification of the polymorphisms is performed by whole genome sequencing using NGS technologies as described herein.

The invention provides a method for identifying copy number variations (CNV) as polymorphisms of a sequence of interest in a test sample that comprises a mixture of nucleic acids derived from two different genomes, and which are known or are suspected to differ in the amount of one or more sequence of interest. Copy number variations determined by the method of the invention include gains or losses of entire chromosomes, alterations involving very large chromosomal segments that are microscopically visible, and an abundance of sub-microscopic copy number variation of DNA segments ranging from kilobases (kb) to megabases (Mb) in size.

CNV in the human genome significantly influence human diversity and predisposition to disease (Redon et al., Nature 23:444-454 [2006], Shaikh et al. Genome Res 19:1682-1690 [2009]). CNVs have been known to contribute to genetic disease through different mechanisms, resulting in either imbalance of gene dosage or gene disruption in most cases. In addition to their direct correlation with genetic disorders, CNVs are known to mediate phenotypic changes that can be deleterious. Recently, several studies have reported an increased burden of rare or de novo CNVs in complex disorders such as Autism, ADHD, and schizophrenia as compared to normal controls, highlighting the potential pathogenicity of rare or unique CNVs (Sebat et al., 316: 445-449 [2007]; Walsh et al., Science 320:539-543 [2008]). CNV arise from genomic rearrangements, primarily owing to deletion, duplication, insertion, and unbalanced translocation events.

Embodiments of the invention provide for a method to assess copy number variation of a sequence of interest e.g. a clinically-relevant sequence, in a test sample that comprises a mixture of nucleic acids derived from two different genomes, and which are known or are suspected to differ in the amount of one or more sequence of interest. The mixture of nucleic acids is derived from two or more types of cells. In one embodiment, the mixture of nucleic acids is derived from normal and cancerous cells derived from a subject suffering from a medical condition e.g. cancer.

It is believed that many solid tumors, such as breast cancer, progress from initiation to metastasis through the accumulation of several genetic aberrations. [Sato et al., Cancer Res., 50: 7184-7189 [1990]; Jongsma et al., J Clin Pathol: Mol Path 55:305-309 [2002])]. Such genetic aberrations, as they accumulate, may confer proliferative advantages, genetic instability and the attendant ability to evolve drug resistance rapidly, and enhanced angiogenesis, proteolysis and metastasis. The genetic aberrations may affect either recessive "tumor suppressor genes" or dominantly acting oncogenes. Deletions and recombination leading to loss of heterozygosity (LOH) are believed to play a major role in tumor progression by uncovering mutated tumor suppressor alleles.

cfDNA has been found in the circulation of patients diagnosed with malignancies including but not limited to lung cancer (Pathak et al. Clin Chem 52:1833-1842 [2006]), prostate cancer (Schwartzenbach et al. Clin Cancer Res 15:1032-8 [2009]), and breast cancer (Schwartzenbach et al. available online at breast-cancer-research.com/content/11/5/R71 [2009]). Identification of genomic instabilities associated with cancers that can be determined in the circulating cfDNA in cancer patients is a potential diagnostic and prognostic tool. In one embodiment, the method of the invention assesses CNV of a sequence of interest in a sample comprising a mixture of nucleic acids derived from a subject that is suspected or is known to have cancer e.g. carcinoma, sarcoma, lymphoma, leukemia, germ cell tumors and blastoma. In one embodiment, the sample is a plasma sample derived (processes) from peripheral blood and that comprises a mixture of cfDNA derived from normal and cancerous cells. In another embodiment, the biological sample that is needed to determine whether a CNV is present is derived from a mixture of cancerous and non-cancerous cells from other biological fluids including but not limited to serum, sweat, tears, sputum, urine, sputum, ear flow, lymph, saliva, cerebrospinal fluid, ravages, bone marrow suspension, vaginal flow, transcervical lavage, brain fluid, ascites, milk, secretions of the respiratory, intestinal and genitourinary tracts, and leukophoresis samples, or in tissue biopsies, swabs or smears.

The sequence of interest is a nucleic acid sequence that is known or is suspected to play a role in the development and/or progression of the cancer. Examples of a sequence of interest include nucleic acids sequences that are amplified or deleted in cancerous cells as described in the following.

Dominantly acting genes associated with human solid tumors typically exert their effect by overexpression or altered expression. Gene amplification is a common mechanism leading to upregulation of gene expression. Evidence from cytogenetic studies indicates that significant amplification occurs in over 50% of human breast cancers. Most notably, the amplification of the proto-oncogene human epidermal growth factor receptor 2 (HER2) located on chromosome 17 (17(17q21-q22)), results in overexpression of HER2 receptors on the cell surface leading to excessive and dysregulated signaling in breast cancer and other malignancies (Park et al., Clinical Breast Cancer 8:392-401 [2008]). A variety of oncogenes have been found to be amplified in other human malignancies. Examples of the amplification of cellular oncogenes in human tumors include amplifications of: c-myc in promyelocytic leukemia cell line HL60, and in small-cell lung carcinoma cell lines, N-myc in primary neuroblastomas (stages III and IV), neuroblastoma cell lines, retinoblastoma cell line and primary tumors, and small-cell lung carcinoma lines and tumors, L-myc in small-cell lung carcinoma cell lines and tumors, c-myb in acute myeloid leukemia and in colon carcinoma cell lines, c-erbb in epidermoid carcinoma cell, and primary gliomas, c-K-ras-2 in primary carcinomas of lung, colon, bladder, and rectum, N-ras in mammary carcinoma cell line (Varmus H., Ann Rev Genetics 18: 553-612 (1984) [cited in Watson et al., Molecular Biology of the Gene (4th ed.; Benjamin/Cummings Publishing Co. 1987)].

Chromosomal deletions involving tumor suppressor genes may play an important role in the development and progression of solid tumors. The retinoblastoma tumor suppressor gene (Rb-1), located in chromosome 13q14, is the most extensively characterized tumor suppressor gene. The Rb-1 gene product, a 105 kDa nuclear phosphoprotein, apparently plays an important role in cell cycle regulation (Howe et al., Proc Natl Acad Sci (USA) 87:5883-5887 [1990]). Altered or lost expression of the Rb protein is caused by inactivation of both gene alleles either through a point mutation or a chromosomal deletion. Rb-i gene alterations have been found to be present not only in retinoblastomas but also in other malignancies such as osteosarcomas, small cell lung cancer (Rygaard et al., Cancer Res 50: 5312-5317 [1990)]) and breast cancer. Restriction fragment length polymorphism (RFLP) studies have indicated that such tumor types have frequently lost heterozygosity at 13q suggesting that one of the Rb-1 gene alleles has been lost due to a gross chromosomal deletion (Bowcock et al., Am J Hum Genet, 46: 12 [1990]). Chromosome 1 abnormalities including duplications, deletions and unbalanced translocations involving chromosome 6 and other partner chromosomes indicate that regions of chromosome 1, in particular 1q21-1q32 and 1p11-13, might harbor oncogenes or tumor suppressor genes that are pathogenetically relevant to both chronic and advanced phases of myeloproliferative neoplasms (Caramazza et al., Eur J Hematol 84:191-200 [2010]). Myeloproliferative neoplasms are also associated with deletions of chromosome 5. Complete loss or interstitial deletions of chromosome 5 are the most common karyotypic abnormality in myelodysplastic syndromes (MDSs). Isolated del(5q)/5q-MDS patients have a more favorable prognosis than those with additional karyotypic defects, who tend to develop myeloproliferative neoplasms (MPNs) and acute myeloid leukemia. The frequency of unbalanced chromosome 5 deletions has led to the idea that 5q harbors one or more tumor-suppressor genes that have fundamental roles in the growth control of hematopoietic stem/progenitor cells (HSCs/HPCs). Cytogenetic mapping of commonly deleted regions (CDRs) centered on 5q31 and 5q32 identified candidate tumor-suppressor genes, including the ribosomal subunit RPS14, the transcription factor Egr1/Krox20 and the cytoskeletal remodeling protein, alpha-catenin (Eisenmann et al., Oncogene 28:3429-3441 [2009]). Cytogenetic and allelotyping studies of fresh tumours and tumour cell lines have shown that allelic loss from several distinct regions on chromosome 3p, including 3p25, 3p21-22, 3p21.3, 3p12-13 and 3p14, are the earliest and most frequent genomic abnormalities involved in a wide spectrum of major epithelial cancers of lung, breast, kidney, head and neck, ovary, cervix, colon, pancreas, esophagous, bladder and other organs. Several tumor suppressor genes have been mapped to the chromosome 3p region, and are thought that interstitial deletions or promoter hypermethylation precede the loss of the 3p or the entire chromosome 3 in the development of carcinomas (Angeloni D., Briefings Functional Genomics 6:19-39 [2007]).

Newborns and children with Down syndrome (DS) often present with congenital transient leukemia and have an increased risk of acute myeloid leukemia and acute lymphoblastic leukemia. Chromosome 21, harboring about 300 genes, may be involved in numerous structural aberrations, e.g., translocations, deletions, and amplifications, in leukemias, lymphomas, and solid tumors. Moreover, genes located on chromosome 21 have been identified that play an important role in tumorigenesis. Somatic numerical as well as structural chromosome 21 aberrations are associated with leukemias, and specific genes including RUNX1, TMPRSS2, and TFF, which are located in 21q, play a role in tumorigenesis (Fonatsch C Gene Chromosomes Cancer 49:497-508 [2010]).

In one embodiment, the method provides a means to assess the association between gene amplification and the extent of tumor evolution. Correlation between amplification and/or deletion and stage or grade of a cancer may be prognostically important because such information may contribute to the definition of a genetically based tumor grade that would better predict the future course of disease with more advanced tumors having the worst prognosis. In addition, information about early amplification and/or deletion events may be useful in associating those events as predictors of subsequent disease progression. Gene amplification and deletions as identified by the method can be associated with other known parameters such as tumor grade, histology, Brd/Urd labeling index, hormonal status, nodal involvement, tumor size, survival duration and other tumor properties available from epidemiological and biostatistical studies. For example, tumor DNA to be tested by the method could include atypical hyperplasia, ductal carcinoma in situ, stage I-III cancer and metastatic lymph nodes in order to permit the identification of associations between amplifications and deletions and stage. The associations made may make possible effective therapeutic intervention. For example, consistently amplified regions may contain an overexpressed gene, the product of which may be able to be attacked therapeutically (for example, the growth factor receptor tyrosine kinase, p185$^{HER2}$).

The method can be used to identify amplification and/or deletion events that are associated with drug resistance by determining the copy number variation of nucleic acids from primary cancers to those of cells that have metastasized to other sites. If gene amplification and/or deletion is a manifestation of karyotypic instability that allows rapid development of drug resistance, more amplification and/or deletion in primary tumors from chemoresistant patients than in tumors in chemosensitive patients would be expected. For example, if amplification of specific genes is responsible for the development of drug resistance, regions surrounding those genes would be expected to be amplified consistently in tumor cells from pleural effusions of chemoresistant patients but not in the primary tumors. Discovery of associations between gene amplification and/or deletion and the development of drug resistance may allow the identification of patients that will or will not benefit from adjuvant therapy.

In other embodiments, the present method can be used to identify polymorphisms associated with trinucleotide repeat disorders, which are a set of genetic disorders caused by trinucleotide repeat expansion. Trinucleotide expansions are a subset of unstable microsatellite repeats that occur throughout all genomic sequences. If the repeat is present in a healthy gene, a dynamic mutation may increase the repeat count and result in a defective gene. In one embodiment, the method can be used to identify trinucleotide repeats associated with fragile X syndrome. The long arm of the X chromosome of patients suffering from fragile X syndrome can contain from 230 to 4000 CGG, as compared with 60 to 230 repeats in carriers and 5 to 54 repeats in unaffected individuals. The chromosomal instability resulting from this trinucleotide expansion presents clinically as mental retardation, distinctive facial features, and macroorchidism in males. The second, related DNA-triplet repeat disease, fragile X-E syndrome, was also identified on the X chromosome, but was found to be the result of an expanded CCG repeat. The present method can identify trinucleotide repeats associated with other repeat expansion disorders including Categories I, II and III. Category I disorders include Huntington's disease (HD) and the spinocerebellar ataxias that are caused by a CAG repeat expansion in protein-coding portions of specific genes. Category II expansions tend to be more phenotypically diverse with heterogeneous expansions that are generally small in magnitude, but also found in the exons of genes. Category III includes fragile X syndrome, myotonic dystrophy, two of the spinocerebellar ataxias, juvenile myoclonic epilepsy and friereich's ataxia. These diseases are characterized by typically much larger repeat expansions than the first two groups, and the repeats are located outside of the protein-coding regions of the genes.

In other embodiments, the present method can identify CAG trinucleotide repeats associated with at least ten neurologic disorders known to be caused by an increased number of CAG repeats, typically in coding regions of otherwise unrelated proteins. During protein synthesis, the expanded CAG repeats are translated into a series of uninterrupted glutamine residues forming what is known as a polyglutamine tract ("polyQ"). Such polyglutamine tracts may be subject to increased aggregation. These disorders are characterized by autosomal dominant mode of inheritance (with the exception of spino-bulbar muscular atrophy which shows X-linked inheritance), midlife onset, a progressive course, and a correlation of the number of CAG repeats with the severity of disease and the age at onset. Causative genes are widely expressed in all of the known polyglutamine diseases. A common symptom of PolyQ diseases is characterized by a progressive degeneration of nerve cells usually affecting people later in life. Although these diseases share the same repeated codon (CAG) and some symptoms, the repeats for the different polyglutamine diseases occur on different chromosomes. Examples of polyQ disorders that can be identified by the present method include without limitation DRPLA (Dentatorubropallidoluysian atrophy), HD (Huntington's disease), SBMA (Spinobulbar muscular atrophy or Kennedy disease), SCA1 (Spinocerebellar ataxia Type 1), SCA2 (Spinocerebellar ataxia Type 2), SCA3 (Spinocerebellar ataxia Type 3 or Machado-Joseph disease), SCA6 (Spinocerebellar ataxia Type 6), SCA7 (Spinocerebellar ataxia Type 7), SCA17 (Spinocerebellar ataxia Type 17). Examples of non-polyQ disorders that can be identified by the present method include FRAXA (Fragile X syndrome), FXTAS (Fragile X-associated tremor/ataxia syndrome), FRAXE (Fragile XE mental retardation), FRDA (Friedreich's ataxia), DM (Myotonic dystrophy), SCA8 (Spinocerebellar ataxia Type 8), SCA12 (Spinocerebellar ataxia Type 12).

In addition to the role of CNV in cancer, CNVs have been associated with a growing number of common complex disease, including human immunodeficiency virus (HIV), autoimmune diseases and a spectrum of neuropsychiatric disorders.

To date a number of studies have reported association between CNV in genes involved in inflammation and the immune response and HIV, asthma, Crohn's disease and other autoimmune disorders (Fanciulli et al., Clin Genet 77:201-213 [2010]). For example, CNV in CCL3L1, has been implicated in HIV/AIDS susceptibility (CCL3L1, 17q11.2 deletion), rheumatoid arthritis (CCL3L1, 17q11.2 deletion), and Kawasaki disease (CCL3L1, 17q11.2 duplication); CNV in HBD-2, has been reported to predispose to colonic Crohn's disease (HDB-2, 8p23.1 deletion) and psoriasis (HDB-2, 8p23.1 deletion); CNV in FCGR3B, was shown to predispose to glomerulonephritis in systemic lupus erthematosous (FCGR3B, 1q23 deletion, 1q23 duplication), anti-neutrophil cytoplasmic antibody (ANCA)-associated vasculatis (FCGR3B, 1q23 deletion), and increase the risk of developing rheumatoid arthritis. There are at least two inflammatory or autoimmune diseases that have been shown to be associated with CNV at different gene loci. For example, Crohn's disease is associated with low copy number at HDB-2, but also with a common deletion polymorphism upstream of the IGRM gene that encodes a member of the p47 immunity-related GTPase family. In addition to the association with FCGR3B copy number, SLE susceptibility has also been reported to be significantly increased among subjects with a lower number of copies of complement component C4.

Associations between genomic deletions at the GSTM1 (GSTM1, 1q23deletion) and GSTT1 (GSTT1, 22q11.2 deletion) loci and increased risk of atopic asthma have been reported in a number of independent studies. In some embodiments, the present method can be used to determine the presence or absence of a CNV associated with inflammation and/or autoimmune diseases. For example, the present method can be used to determine the presence of a CNV in a patient suspected to be suffering from HIV, asthma, or Crohn's disease. Examples of CNV associated with such diseases include without limitation deletions at 17q11.2, 8p23.1, 1q23, and 22q11.2, and duplications at 17q11.2, and 1q23. In some embodiments, the present method can be used to determine the presence of CNV in genes including but not limited to CCL3L1, HBD-2, FCGR3B, GSTM, GSTT1, C4, and MGM.

Associations between de novo and inherited CNV and several common neurological and psychiatric diseases have been reported in autism, schizophrenia and epilepsy, and some cases of neurodegenerative diseases such as Parkinson's disease, amyotrophic lateral sclerosis (ALS) and autosomal dominant Alzheimer's disease (Fanciulli et al., Clin Genet 77:201-213 [2010]). Cytogenetic abnormalities have been observed in patients with autism and autism spectrum disorders (ASDs) with duplications at 15q11-q13. According to the Autism Genome project Consortium, 154 CNV including several recurrent CNVs, either on chromosome 15q11-q13 or at new genomic locations including chromosome 2p16, 1q21 and at 17p12 in a region associated with Smith-Magenis syndrome that overlaps with ASD. Recurrent microdeletions or microduplications on chromosome 16p11.2 have highlighted the observation that de novo CNVs are detected at loci for genes such as SHANK3 (22q13.3 deletion), neurexin 1 (NRXNJ, 2p16.3 deletion) and the neuroglins (NLGN4, Xp22.33 deletion) that are known to regulate synaptic differentiation and regulate glutaminergic neurotransmitter release. Schizophrenia has also been associated with multiple de novo CNVs. Microdeletions and microduplications associated with schizophrenia contain an overrepresentation of genes belonging to neurodevelopmental and glutaminergic pathways, suggesting that multiple CNVs affecting these genes may contribute directly to the pathogenesis of schizophrenia e.g. ERBB4, 2q34 deletion, SLC1A3, 5p13.3 deletion; RAPEGF4, 2q31.1 deletion; CIT, 12.24 deletion; and multiple genes with de novo CNV. CNVs have also been associated with other neurological disorders including epilepsy (CHRNA7, 15q13.3 deletion), Parkinson's disease (SNCA 4q22 duplication) and ALS (SMN1, 5q12.2.-q13.3 deletion; and SMN2 deletion). In some embodiments, the present method can be used to determine the presence or absence of a CNV associated with diseases of the nervous system. For example, the present method can be used to determine the presence of a CNV in a patient suspected to be suffering from autism, schizophrenia, epilepsy, neurodegenerative diseases such as Parkinson's disease, amyotrophic lateral sclerosis (ALS) or autosomal dominant Alzheimer's disease. The present method can be used to determine CNV of genes associated with diseases of the nervous system including without limitation any of the Autism Spectrum Disorders (ASD), schizophrenia, and epilepsy, and CNV of genes associated with neurodegenerative disorders such as Parkinson's disease. Examples of CNV associated with such diseases include without limitation duplications at 15q11-q13, 2p16, 1q21, 17p12, 16p11.2, and 4q22, and deletions at 22q13.3, 2p16.3, Xp22.33, 2q34, 5p13.3, 2q31.1, 12.24, 15q13.3, and 5q12.2. In some embodiments, the present method can be used to determine the presence of CNV in genes including but not limited to SHANK3, NLGN4, NRXN1, ERBB4, SLC1A3, RAPGEF4, CIT, CHRNA7, SNCA, SMN1, and SMN2.

The association between metabolic and cardiovascular traits, such as familial hypercholesterolemia (FH), atherosclerosis and coronary artery disease, and CNVs has been reported in a number of studies (Fanciulli et al., Clin Genet 77:201-213 [2010]). For example, germline rearrangements, mainly deletions, have been observed at the LDLR gene (LDLR, 19p13.2 deletion/duplication) in some FH patients who carry no other LDLR mutations. Another example is the LPA gene that encodes apolipoprotein(a) (apo(a)) whose plasma concentration is associated with risk of coronary artery disease, myocardial infarction (MI) and stroke. Plasma concentrations of the apo(a) containing lipoprotein Lp(a) vary over 1000-fold between individuals and 90% of this variability is genetically determined at the LPA locus, with plasma concentration and Lp(a) isoform size being proportional to a highly variable number of 'kringle 4' repeat sequences (range 5-50). These data indicate that CNV in at least two genes can be associated with cardiovascular risk. The present method can be used in large studies to search specifically for CNV associations with cardiovascular disorders. In some embodiments, the present method can be used to determine the presence or absence of a CNV associated with metabolic or cardiovascular disease. For example, the present method can be used to determine the presence of a CNV in a patient suspected to be suffering from familial hypercholesterolemia. The present method can be used to determine CNV of genes associated with metabolic or cardiovascular disease e.g. hypercholesterolemia. Examples of CNV associated with such diseases include without limitation 19p13.2 deletion/duplication of the LDLR gene, and multiplications in the LPA gene.

Sequencing

In various embodiments, the method described herein employs next generation sequencing technology (NGS) in which clonally amplified DNA templates or single DNA molecules are sequenced in a massively parallel fashion within a flow cell (e.g. as described in Volkerding et al. Clin Chem 55:641-658 [2009]; Metzker M Nature Rev 11:31-46 [2010]). In addition to high-throughput sequence information, NGS provides digital quantitative information, in that each sequence read is a countable "sequence tag" representing an individual clonal DNA template or a single DNA molecule. The sequencing technologies of NGS include pyrosequencing, sequencing-by-synthesis with reversible dye terminators, sequencing by oligonucleotide probe ligation and real time sequencing.

In various embodiments, one can analyze samples that are not amplified, or are only partially amplified (target amplification). In some cases, the methods of determining fetal fraction can be accomplished without requiring any type of targeted amplification.

Whole genome amplification that occurs as part of the sequencing process provides sufficient copies that can be covered by increasing number of sequencing cycles to provide increasingly better coverage.

In preferred embodiments, the sample comprising the mixture of DNA molecules derived from two different genomes is non-specifically enriched for the whole genome sequences prior to whole genome sequencing i.e. whole genome amplification is performed prior to sequencing.

Non-specific enrichment of sample DNA may refer to the whole genome amplification of the genomic DNA fragments of the sample that can be used to increase the level of the sample DNA prior to identifying polymorphisms by sequencing. Non-specific enrichment can be the selective enrichment of one of the two genomes present in the sample. For example, non-specific enrichment can be selective of the fetal genome in a maternal sample, which can be obtained by known methods to increase the relative proportion of fetal to maternal DNA in a sample. Alternatively, non-specific enrichment can be the non-selective amplification of both genomes present in the sample. For example, non-specific amplification can be of fetal and maternal DNA in a sample comprising a mixture of DNA from the fetal and maternal genomes. Methods for whole genome amplification are known in the art. Degenerate oligonucleotide-primed PCR (DOP), primer extension PCR technique (PEP) and multiple displacement amplification (MDA), are examples of whole genome amplification methods. In some embodiments, the sample comprising the mixture of cfDNA from different genomes is unenriched for cfDNA of the genomes present in the mixture. In other embodiments, the sample comprising the mixture of cfDNA from different genomes is non-specifically enriched for any one of the genomes present in the sample.

In other embodiments, the cfDNA in the sample is enriched specifically. Specific enrichment refers to the enrichment of a genomic sample for specific sequences e.g. polymorphic target sequence, which are selected for amplification prior to sequencing the DNA sample. However, an advantage of the disclosed embodiments is that targeted amplification is not needed. Polymorphic Some of the sequencing technologies are available commercially, such as the sequencing-by-hybridization platform from Affymetrix Inc. (Sunnyvale, Calif.) and the sequencing-by-synthesis platforms from 454 Life Sciences (Bradford, Conn.), Illumina/Solexa (Hayward, Calif.) and Helicos Biosciences (Cambridge, Mass.), and the sequencing-by-ligation platform from Applied Biosystems (Foster City, Calif.), as described below. In addition to the single molecule sequencing performed using sequencing-by-synthesis of Helicos Biosciences, other single molecule sequencing technologies are encompassed by the disclosed method and include the SMRT™ technology of Pacific Biosciences, the Ion Torrent™ technology, and nanopore sequencing being developed for example, by Oxford Nanopore Technologies.

While the automated Sanger method is considered as a 'first generation' technology, Sanger sequencing including the automated Sanger sequencing, can also be employed by the disclosed method. Additional sequencing methods that comprise the use of developing nucleic acid imaging technologies e.g. atomic force microscopy (AFM) or transmission electron microscopy (TEM), are also encompassed by the disclosed method. Exemplary sequencing technologies are described below.

In one embodiment, the DNA sequencing technology that is used in the disclosed methods is the Helicos True Single Molecule Sequencing (tSMS) (e.g. as described in Harris T. D. et al., Science 320:106-109 [2008]). In the tSMS technique, a DNA sample is cleaved into strands of approximately 100 to 200 nucleotides, and a polyA sequence is added to the 3' end of each DNA strand. Each strand is labeled by the addition of a fluorescently labeled adenosine nucleotide. The DNA strands are then hybridized to a flow cell, which contains millions of oligo-T capture sites that are immobilized to the flow cell surface. The templates can be at a density of about 100 million templates/cm$^2$. The flow cell is then loaded into an instrument, e.g., HeliScope™ sequencer, and a laser illuminates the surface of the flow cell, revealing the position of each template. A CCD camera can map the position of the templates on the flow cell surface. The template fluorescent label is then cleaved and washed away. The sequencing reaction begins by introducing a DNA polymerase and a fluorescently labeled nucleotide. The oligo-T nucleic acid serves as a primer. The polymerase incorporates the labeled nucleotides to the primer in a template directed manner. The polymerase and unincorporated nucleotides are removed. The templates that have directed incorporation of the fluorescently labeled nucleotide are discerned by imaging the flow cell surface. After imaging, a cleavage step removes the fluorescent label, and the process is repeated with other fluorescently labeled nucleotides until the desired read length is achieved. Sequence information is collected with each nucleotide addition step. Whole genome sequencing by single molecule sequencing technologies excludes PCR-based amplification in the preparation of the sequencing libraries, and the directness of sample preparation allows for direct measurement of the sample, rather than measurement of copies of that sample.

In one embodiment, the DNA sequencing technology that is used in the disclosed methods is the 454 sequencing (Roche) (e.g. as described in Margulies, M. et al. Nature 437:376-380 (2005)). 454 sequencing involves two steps. In the first step, DNA is sheared into fragments of approximately 300-800 base pairs, and the fragments are blunt-ended. Oligonucleotide adaptors are then ligated to the ends of the fragments. The adaptors serve as primers for amplification and sequencing of the fragments. The fragments can be attached to DNA capture beads, e.g., streptavidin-coated beads using, e.g., Adaptor B, which contains 5'-biotin tag. The fragments attached to the beads are PCR amplified within droplets of an oil-water emulsion. The result is multiple copies of clonally amplified DNA fragments on each bead. In the second step, the beads are captured in wells (pico-liter sized). Pyrosequencing is performed on each DNA fragment in parallel. Addition of one or more nucleotides generates a light signal that is recorded by a CCD camera in a sequencing instrument. The signal strength is proportional to the number of nucleotides incorporated. Pyrosequencing makes use of pyrophosphate (PPi) which is released upon nucleotide addition. PPi is converted to ATP by ATP sulfurylase in the presence of adenosine 5' phosphosulfate. Luciferase uses ATP to convert luciferin to oxyluciferin, and this reaction generates light that is discerned and analyzed.

In one embodiment, the DNA sequencing technology that is used in the disclosed methods is the SOLiD™ technology (Applied Biosystems). In SOLiD™ sequencing-by-ligation, genomic DNA is sheared into fragments, and adaptors are attached to the 5' and 3' ends of the fragments to generate a fragment library. Alternatively, internal adaptors can be introduced by ligating adaptors to the 5' and 3' ends of the fragments, circularizing the fragments, digesting the circularized fragment to generate an internal adaptor, and attaching adaptors to the 5' and 3' ends of the resulting fragments to generate a mate-paired library. Next, clonal bead populations are prepared in microreactors containing beads, primers, template, and PCR components. Following PCR, the templates are denatured and beads are enriched to separate the beads with extended templates. Templates on the selected beads are subjected to a 3' modification that permits bonding to a glass slide. The sequence can be determined by sequential hybridization and ligation of partially random oligonucleotides with a central determined base (or pair of bases) that is identified by a specific fluorophore. After a color is recorded, the ligated oligonucleotide is cleaved and removed and the process is then repeated.

In one embodiment, the DNA sequencing technology that is used in the disclosed methods is the single molecule, real-time (SMRT™) sequencing technology of Pacific Biosciences. In SMRT sequencing, the continuous incorporation of dye-labeled nucleotides is imaged during DNA synthesis. Single DNA polymerase molecules are attached to the bottom surface of individual zero-mode wavelength identifiers (ZMW identifiers) that obtain sequence information while phospholinked nucleotides are being incorporated into the growing primer strand. A ZMW is a confinement structure which enables observation of incorporation of a single nucleotide by DNA polymerase against the background of fluorescent nucleotides that rapidly diffuse in an out of the ZMW (in microseconds). It takes several milliseconds to incorporate a nucleotide into a growing strand. During this time, the fluorescent label is excited and produces a fluorescent signal, and the fluorescent tag is cleaved off. Identification of the corresponding fluorescence of the dye indicates which base was incorporated. The process is repeated.

In one embodiment, the DNA sequencing technology that is used in the disclosed methods is nanopore sequencing (e.g. as described in Soni G V and Meller A. Clin Chem 53: 1996-2001 [2007]). Nanopore sequencing DNA analysis techniques are being industrially developed by a number of companies, including Oxford Nanopore Technologies (Oxford, United Kingdom). Nanopore sequencing is a single-molecule sequencing technology whereby a single molecule of DNA is sequenced directly as it passes through a nanopore. A nanopore is a small hole, of the order of 1 nanometer in diameter. Immersion of a nanopore in a conducting fluid and application of a potential (voltage) across it results in a slight electrical current due to conduction of ions through the nanopore. The amount of current which flows is sensitive to the size and shape of the nanopore. As a DNA molecule passes through a nanopore, each nucleotide on the DNA molecule obstructs the nanopore to a different degree, changing the magnitude of the current through the nanopore in different degrees. Thus, this change in the current as the DNA molecule passes through the nanopore represents a reading of the DNA sequence.

In one embodiment, the DNA sequencing technology that is used in the disclosed methods is the chemical-sensitive field effect transistor (chemFET) array (e.g., as described in U.S. Patent Publication No. 2009/0026082 filed Dec. 17, 2007). In one example of the technique, DNA molecules can be placed into reaction chambers, and the template molecules can be hybridized to a sequencing primer bound to a polymerase. Incorporation of one or more triphosphates into a new nucleic acid strand at the 3' end of the sequencing primer can be discerned by a change in current by a chemFET. An array can have multiple chemFET sensors. In another example, single nucleic acids can be attached to beads, and the nucleic acids can be amplified on the bead, and the individual beads can be transferred to individual reaction chambers on a chemFET array, with each chamber having a chemFET sensor, and the nucleic acids can be sequenced.

In one embodiment, the DNA sequencing technology that is used in the disclosed methods is the Halcyon Molecular's method that uses transmission electron microscopy (TEM). The method, termed Individual Molecule Placement Rapid Nano Transfer (IMPRNT), comprises utilizing single atom resolution transmission electron microscope imaging of high-molecular weight (150 kb or greater) DNA selectively labeled with heavy atom markers and arranging these molecules on ultra-thin films in ultra-dense (3 nm strand-to-strand) parallel arrays with consistent base-to-base spacing. The electron microscope is used to image the molecules on the films to determine the position of the heavy atom markers and to extract base sequence information from the DNA. The method is further described in PCT patent publication WO 2009/046445. The method allows for sequencing complete human genomes in less than ten minutes.

In one embodiment, the DNA sequencing technology is the Ion Torrent single molecule sequencing, which pairs semiconductor technology with a simple sequencing chemistry to directly translate chemically encoded information (A, C, G, T) into digital information (0, 1) on a semiconductor chip. In nature, when a nucleotide is incorporated into a strand of DNA by a polymerase, a hydrogen ion is released as a byproduct. Ion Torrent uses a high-density array of micro-machined wells to perform this biochemical process in a massively parallel way. Each well holds a different DNA molecule. Beneath the wells is an ion-sensitive layer and beneath that an ion sensor. When a nucleotide, for example a C, is added to a DNA template and is then incorporated into a strand of DNA, a hydrogen ion will be released. The charge from that ion will change the pH of the solution, which can be identified by Ion Torrent's ion sensor. The sequencer—essentially the world's smallest solid-state pH meter—calls the base, going directly from chemical information to digital information. The Ion personal Genome Machine (PGM™) sequencer then sequentially floods the chip with one nucleotide after another. If the next nucleotide that floods the chip is not a match. No voltage change will be recorded and no base will be called. If there are two identical bases on the DNA strand, the voltage will be double, and the chip will record two identical bases called. Direct identification allows recordation of nucleotide incorporation in seconds.

In some embodiments, the methods employ PCR or a related technique for amplifying sample nucleotide sequences before identifying or mapping them. However, the algorithmic techniques disclosed herein generally do not require amplification, particularly targeted amplification of polymorphisms used to estimate genome fraction.

Certain embodiments employ digital PCR and sequencing by hybridization. Digital polymerase chain reaction (digital PCR or dPCR) can be used to directly identify and quantify nucleic acids in a sample. Digital PCR can be performed in an emulsion. Individual nucleic acids are separated, e.g., in a microfluidic chamber device, and each nucleic acid is individually amplified by PCR. Nucleic acids can be separated such there is an average of approximately 0.5 nucleic acids/well, or not more than one nucleic acid/well. Different probes can be used to distinguish fetal alleles and maternal alleles. Alleles can be enumerated to determine copy number. In sequencing by hybridization, the hybridization comprises contacting the plurality of polynucleotide sequences with a plurality of polynucleotide probes, wherein each of the plurality of polynucleotide probes can be optionally tethered to a substrate. The substrate might be flat surface comprising an array of known nucleotide sequences. The pattern of hybridization to the array can be used to determine the polynucleotide sequences present in the sample. In other embodiments, each probe is tethered to a bead, e.g., a magnetic bead or the like. Hybridization to the beads can be identified and used to identify the plurality of polynucleotide sequences within the sample.

In one embodiment, the method employs massively parallel sequencing of millions of DNA fragments using Illumina's sequencing-by-synthesis and reversible terminator-based sequencing chemistry (e.g. as described in Bentley et al., Nature 6:53-59 [2009]). Template DNA can be genomic DNA e.g. cfDNA. In some embodiments, genomic DNA from isolated cells is used as the template, and it is fragmented into lengths of several hundred base pairs. In other embodiments, cfDNA is used as the template, and fragmentation is not required as cfDNA exists as short fragments. For example fetal cfDNA circulates in the bloodstream as fragments of <300 bp, and maternal cfDNA has been estimated to circulate as fragments of between about 0.5 and 1 Kb (Li et al., Clin Chem, 50: 1002-1011 (2004)). Illumina's sequencing technology relies on the attachment of fragmented genomic DNA to a planar, optically transparent surface on which oligonucleotide anchors are bound. Template DNA is end-repaired to generate 5'-phosphorylated blunt ends, and the polymerase activity of Klenow fragment is used to add a singleA base to the 3' end of the blunt phosphorylated DNA fragments. This addition prepares the DNA fragments for ligation to oligonucleotide adapters, which have an overhang of a single T base at their 3' end to increase ligation efficiency. The adapter oligonucleotides are complementary to the flow-cell anchors. Under limiting-dilution conditions, adapter-modified, single-stranded template DNA is added to the flow cell and immobilized by hybridization to the anchors. Attached DNA fragments are extended and bridge amplified to create an ultra-high density sequencing flow cell with hundreds of millions of clusters, each containing ~1,000 copies of the same template. In one embodiment, the randomly fragmented genomic DNA e.g. cfDNA, is amplified using PCR before it is subjected to cluster amplification. Alternatively, an amplification-free genomic library preparation is used, and the randomly fragmented genomic DNA e.g. cfDNA is enriched using the cluster amplification alone (Kozarewa et al., Nature Methods 6:291-295 [2009]). The templates are sequenced using a robust four-color DNA sequencing-by-synthesis technology that employs reversible terminators with removable fluorescent dyes. High-sensitivity fluorescence identification is achieved using laser excitation and total internal reflection optics. Short sequence reads of about 20-40 bp e.g. 36 bp, are aligned against a repeat-masked reference genome and genetic differences are called using specially developed data analysis pipeline software. After completion of the first read, the templates can be regenerated in situ to enable a second read from the opposite end of the fragments. Thus, either single-end or paired end sequencing of the DNA fragments is used according to the method. Partial sequencing of DNA fragments present in the sample is performed, and sequence tags comprising reads of predetermined length e.g. 36 bp, that are mapped to a known reference genome are counted.

The length of the sequence read is associated with the particular sequencing technology. NGS methods provide sequence reads that vary in size from tens to hundreds of base pairs. In some embodiments of the method described herein, the sequence reads are about 20 bp, about 25 bp, about 30 bp, about 35 bp, about 40 bp, about 45 bp, about 50 bp, about 55 bp, about 60 bp, about 65 bp, about 70 bp, about 75 bp, about 80 bp, about 85 bp, about 90 bp, about 95 bp, about 100 bp, about 110 bp, about 120 bp, about 130, about 140 bp, about 150 bp, about 200 bp, about 250 bp, about 300 bp, about 350 bp, about 400 bp, about 450 bp, or about 500 bp. It is expected that technological advances will enable single-end reads of greater than 500 bp enabling for reads of greater than about 1000 bp when paired end reads are generated. In one embodiment, the sequence reads are 36 bp. Other sequencing methods that can be employed by the disclosed methods include the single molecule sequencing methods that can sequence nucleic acids molecules>5000 bp. The massive quantity of sequence output is transferred by an analysis pipeline that transforms primary imaging output from the sequencer into strings of bases. A package of integrated algorithms performs the core primary data transformation steps: image analysis, intensity scoring, base calling, and alignment.

Mapping

Various computational methods can be used to map each identified sequence to a bin, e.g., by identifying all sequences in the sample that map to a particular gene, chromosome, allele, or other structure. A number of computer algorithms exist to align sequences, including without limitation BLAST (Altschul et al., 1990), BLITZ (MPsrch) (Sturrock& Collins, 1993), FASTA (Person &Lipman, 1988), BOWTIE (Langmead et al., Genome Biology 10:R25.1-R25.10 [2009]), or ELAND (Illumina, Inc., San Diego, Calif., USA), In some embodiments, the sequences of the bins are found in nucleic acid databases known to those in the art, including without limitation GenBank, dbEST, dbSTS, EMBL (the European Molecular Biology Laboratory), and the DDBJ (the DNA Databank of Japan). BLAST or similar tools can be used to search the identified sequences against the sequence databases, and search hits can be used to sort the identified sequences into the appropriate bins.

Apparatus

Analysis of the sequencing data and the diagnoses derived therefrom are typically performed using computer hardware operating according to defined algorithms and programs. Therefore, certain embodiments employ processes involving data stored in or transferred through one or more computer systems or other processing systems. Embodiments of the invention also relate to apparatus for performing these operations. This apparatus may be specially constructed for the required purposes, or it may be a general-purpose computer (or a group of computers) selectively activated or reconfigured by a computer program and/or data structure stored in the computer. In some embodiments, a group of processors performs some or all of the recited analytical operations collaboratively (e.g., via a network or cloud computing) and/or in parallel. A processor or group of processors for performing the methods described herein may be of various types including microcontrollers and microprocessors such as programmable devices (e.g., CPLDs and FPGAs) and other devices such as gate array ASICs, digital signal processors, and/or general purpose microprocessors.

In addition, certain embodiments relate to tangible and/or non-transitory computer readable media or computer program products that include program instructions and/or data (including data structures) for performing various computer-implemented operations. Examples of computer-readable media include, but are not limited to, semiconductor memory devices, magnetic media such as disk drives, magnetic tape, optical media such as CDs, magneto-optical media, and hardware devices that are specially configured to store and perform program instructions, such as read-only memory devices (ROM) and random access memory (RAM). The computer readable media may be directly controlled by an end user or the media may be indirectly controlled by the end user. Examples of directly controlled media include the media located at a user facility and/or media that are not shared with other entities. Examples of indirectly controlled media include media that is indirectly accessible to the user via an external network and/or via a service providing shared resources such as the "cloud." Examples of program instructions include both machine code, such as produced by a compiler, and files containing higher level code that may be executed by the computer using an interpreter.

In one embodiment, a computer program product is provided for generating an output indicating the fraction of nucleic acid derived from a defined genome (such as that of a fetus) and optionally other information such as the presence or absence of a fetal aneuploidy in a test sample. The computer product may contain instructions for performing any one or more of the above-described methods for determining a fraction of nucleic acids from a particular organism. As explained, the computer product may include a non-transitory and/or tangible computer readable medium having a computer executable or compilable logic (e.g., instructions) recorded thereon for enabling a processor to determine genome fraction and, in some cases, whether an aneuploidy or other condition is present or absent in the genome. In one example, the computer product comprises a computer readable medium having a computer executable or compilable logic (e.g., instructions) recorded thereon for enabling a processor to determine fetal fraction and diagnose a fetal aneuploidy comprising: a receiving procedure for receiving sequencing data from at least a portion of nucleic acid molecules from a maternal biological sample, wherein said sequencing data comprises sequences at the loci of one or more polymorphisms; computer assisted logic for analyzing sequences to determine allele counts for the one or more polymorphisms, and determining fetal fraction of the nucleic acids in the maternal biological sample; and an output procedure for generating an output indicating the fetal fraction of nucleic acids in the sample.

The sequence information from the sample under consideration may be mapped to polymorphism reference sequences as described. Further, the mapped sequence information may be used to generate allele counts and/or determine zygosity cases for the polymorphisms. Such information may be used to determine fetal fraction. In various embodiments, polymorphism reference sequences are stored in a database such as a relational or object database, for example. It should be understood that it is not practical, or even possible in most cases, for an unaided human being to perform any one or all of these computational operations. For example, mapping a single 30 bp read from a sample to a database of polymorphism reference sequences will take potentially a prohibitively long period without the assistance of a computational apparatus. Of course, the problem is compounded because reliable calls often require mapping thousands (e.g., at least about 10,000) or even millions of reads to one or more chromosomes.

In certain embodiments, the disclosed methods make use of a stored list or other organized collection of data concerning reference polymorphisms for the organism producing the nucleic acid sequences to be analyzed. As explained above, the sequences from the sample under consideration can be aligned or otherwise mapped to the stored polymorphisms. The individual polymorphisms are typically sequences of a length sufficient to unambiguously map to sequences identified from the nucleic acid sample. Typically, the polymorphisms come in groups, one for each allele. In various embodiments, the reference polymorphisms are stored in a database containing characteristics of the polymorphisms in addition to their sequences. This collection of information about polymorphisms may be stored in a relational or object database, for example.

Figure 10:
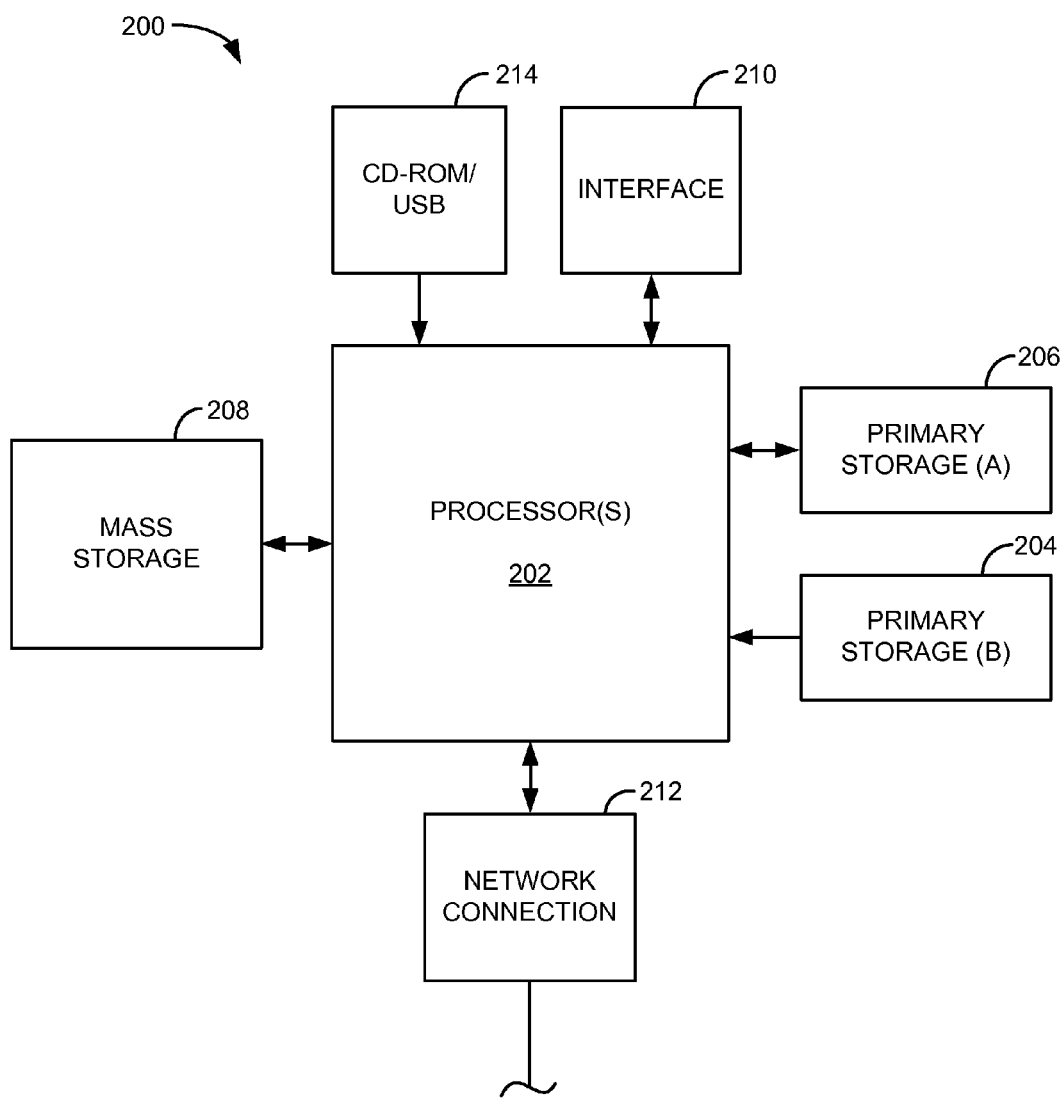
FIG. 10 is a schematic depiction of a computer system that, when appropriately configured (e.g., programmed) or designed, can serve as an analysis apparatus for disclosed embodiments.

FIG. 10 illustrates a typical computer system that, when appropriately configured or designed, can serve as an analysis apparatus of this invention. The computer system 200 includes any number of processors 202 (also referred to as central processing units, or CPUs) that are coupled to storage devices including primary storage 206 (typically a random access memory, or RAM), primary storage 204 (typically a read only memory, or ROM). CPU 202 may be of various types including microcontrollers and microprocessors such as programmable devices (e.g., CPLDs and FPGAs) and unprogrammable devices such as gate array ASICs or general purpose microprocessors. As is well known in the art, primary storage 204 acts to transfer data and instructions to the CPU and primary storage 206 is used typically to transfer data and instructions in a bi-directional manner. Both of these primary storage devices may include any suitable computer-readable media such as those described above. A mass storage device 208 is also coupled bi-directionally to CPU 202 and provides additional data storage capacity and may include any of the computer-readable media described above. Mass storage device 208 may be used to store programs, data and the like and is typically a secondary storage medium such as a hard disk. It will be appreciated that the information retained within the mass storage device 208, may, in appropriate cases, be incorporated in standard fashion as part of primary storage 206 as virtual memory. A specific mass storage device such as a CD-ROM 214 may also pass data uni-directionally to the CPU.

CPU 202 is also coupled to an interface 210 that connects to one or more input/output devices such as such as video monitors, mice, keyboards, microphones, touch-sensitive displays, transducer card readers, tablets, styluses, voice or handwriting recognizers, or other well-known input devices such as, of course, other computers. Finally, CPU 202 optionally may be coupled to an external device such as a database or a computer or telecommunications network using an external connection as shown generally at 212. With such a connection, it is contemplated that the CPU might receive information from the network, or might output information to the network in the course of performing the method steps described herein.

Sequence or other data, can be input into a computer by a user either directly or indirectly. In one embodiment, the computer system 200 is directly coupled to a sequencing tool that reads and/or analyzes sequences of amplified nucleic acids. Sequences or other information from such tools are provided via interface 212 for analysis by system 200. Alternatively, the sequences processed by system 200 are provided from a sequence storage source such as a database or other repository. Once in the processing apparatus 200, a memory device such as primary storage 206 or mass storage 208 buffers or stores, at least temporarily, sequences of the nucleic acids. In addition, the memory device may store tag numbers for various chromosomes or genes, calculated copy counts, etc. The memory may also store various routines and/or programs for analyzing the presenting the sequence or mapped data. Such programs/routines may include programs for performing statistical analyses, etc.

In one example, a user provides a sample into a sequencing apparatus. Data is collected and/or analyzed by the sequencing apparatus which is connected to a computer. Software on the computer allows for data collection and/or analysis. Data can be stored, displayed (via a monitor or other similar device), and/or sent to another location. As indicated, the computer may be connected to the internet which is used to transmit data to a handheld device utilized by a remote user (e.g., a physician, scientist or analyst). It is understood that the data can be stored and/or analyzed prior to transmittal. In some embodiments, raw data is collected and sent to a remote user (or apparatus) who will analyze and/or store the data. Transmittal can occur via the internet, but can also occur via satellite or other connection. Alternately, data can be stored on a computer-readable medium (e.g., CD or semiconductor memory storage device) and the medium can be shipped to an end user (e.g., via mail). The remote user can be in the same or a different geographical location including, but not limited to a building, city, state, country or continent.

In some embodiments, the methods of the invention further comprise collecting data regarding a plurality of polynucleotide sequences and sending the data to a computer. For example, the computer can be connected to laboratory equipment, e.g., a sample collection apparatus, a nucleotide amplification apparatus, a nucleotide sequencing apparatus, or a hybridization apparatus. The computer can then collect applicable data gathered by the laboratory device. The data can be stored on a computer at any step, e.g., while collected in real time, prior to the sending, during or in conjunction with the sending, or following the sending. The data can be stored on a computer-readable medium that can be extracted from the computer. The data collected or stored can be transmitted from the computer to a remote location, e.g., via a local network or a wide area network such as the internet.

In one aspect, the invention further provides a system capable of performing quantitative analysis of nucleotide sequencing with a precision of at least 60%, 65%, 70%, 75%, 80%, 85%, 90%, 91%, 92%, 93%, 94%, 95%, 96%, 97%, 98%, or at least 99%. The nucleotide sequencing can comprise Sanger sequencing, massively parallel sequencing, hybridization or other techniques as described herein. The system can comprise various components, e.g., laboratory equipment and computer systems, and can be configured to carry out the methods of the invention disclosed herein.

In some embodiments, the apparatus and/or programming instructions may further include instructions for automatically recording information pertinent to the method such as fetal DNA fraction and optionally the presence or absence of a fetal chromosomal aneuploidy in a patient medical record for a human subject providing the maternal test sample. The patient medical record may be maintained by, for example, a laboratory, physician's office, a hospital, a health maintenance organization, an insurance company, or a personal medical record website. Further, based on the results of the processor-implemented analysis, the method may further involve prescribing, initiating, and/or altering treatment of a human subject from whom the maternal test sample was taken. This may involve performing one or more additional tests or analyses on additional samples taken from the subject.

EXAMPLE

Fetal Fraction Predicted from Sequenced Variations: Case 2

To demonstrate that the present method can be used to reliably estimate fetal fraction in a maternal sample, an artificial 'maternal' sample was created, and base variations were identified at all loci of chromosomes 1 and 7 to predict the fraction of the minor contributing genome.

cfDNA that is isolated from a pregnant female is a mixture of maternal and fetal cfDNA, with the level of fetal cfDNA corresponding to a median of ~10% of the total cfDNA (Lo et al., 2010, "Maternal Plasma DNA sequencing reveals the genome-wide genetic and mutational profile of the fetus", Prenatal Diagnosis, 2, 1-12). To create the artificial maternal sample, genomic DNA (gDNA) obtained from a mother and her son (mother and son DNAs NA10924 and NA10925; The Coriell Institute for Medical Research, Camden, N.J.) was used to create the sample of mixed genomes. Five micrograms of each of the mother's and son's gDNA were sheared into fragments of about 200 bp, and the concentration of each was determined. An artificial sample containing 10% DNA from the son and 90% DNA from the mother was created to imitate a maternal blood sample, which is believed to typically contain 2-40% fetal cfDNA, depending on the gestational age [Lun et al, 2008, "Microfluidics digital PCR reveals a higher than expected fraction of fetal DNA in maternal plasma", Clinical Chemistry, 54, 1664-1672]. A sequencing library was prepared from the DNA of the artificial sample, and subjected to 50 sequencing cycles on 4 lanes of the flow cell using the IlluminaHiSeq 2000. Approximately 800 million 49-mer sequence reads were generated.

The ~800 million reads were aligned to the Repeat-masked Human Reference Genome (hg19 build) using the GSNAP algorithm (http://research-pub.gene.com/gmap/), allowing for one mismatch and no insertions and no deletions. Sequences that mapped to multiple locations on the genome were ignored. All other mapped reads were counted as sequence tags, and only loci to which 40 and 100 sequence tags were mapped were considered for further analysis i.e. only bases having coverage of 40 and 100 tags were considered.

For each base locus, the number of tags that mapped to each of the four bases were counted. Loci having more than two possible bases were eliminated, and only tags that mapped to monoallelic and biallelic loci were used to predict the artificial fetal fraction. The total number of tags that mapped at each base locus represented the coverage (D) at that locus. In this simulated maternal sample, it is expected that the contribution of the mother's major allele (B) would reflect the 90% portion of the tags, and the contribution of the son's minor allele (A) would reflect the 10% portion of the tags.

Figure 11A:
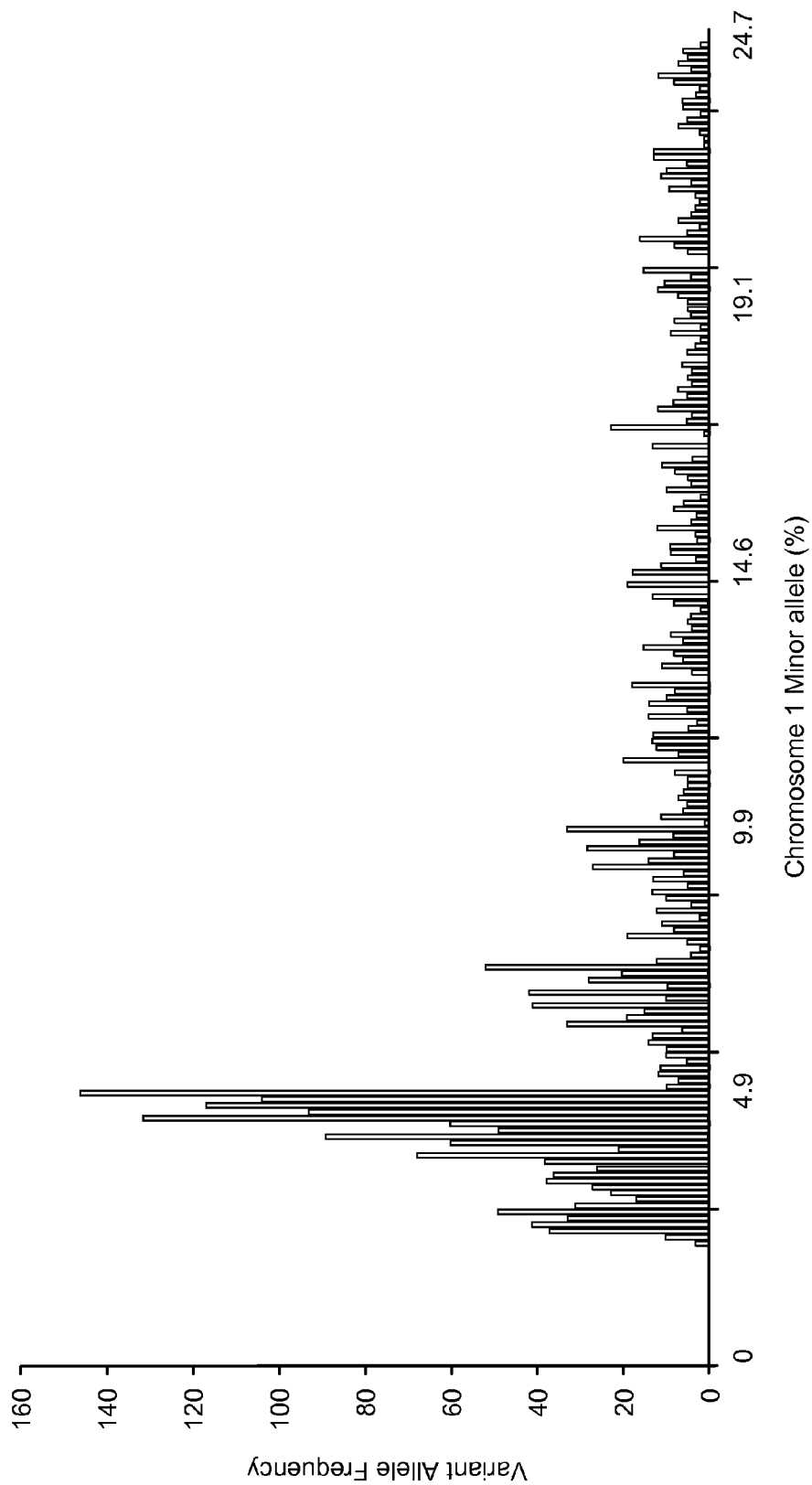
FIGS. 11A and B show a histogram of the number of variant observations (Frequency) at the minor allele percent (A/D) for chromosome chromosomes 1(A) and chromosome 7 as produced in an example.
Figure 11B:
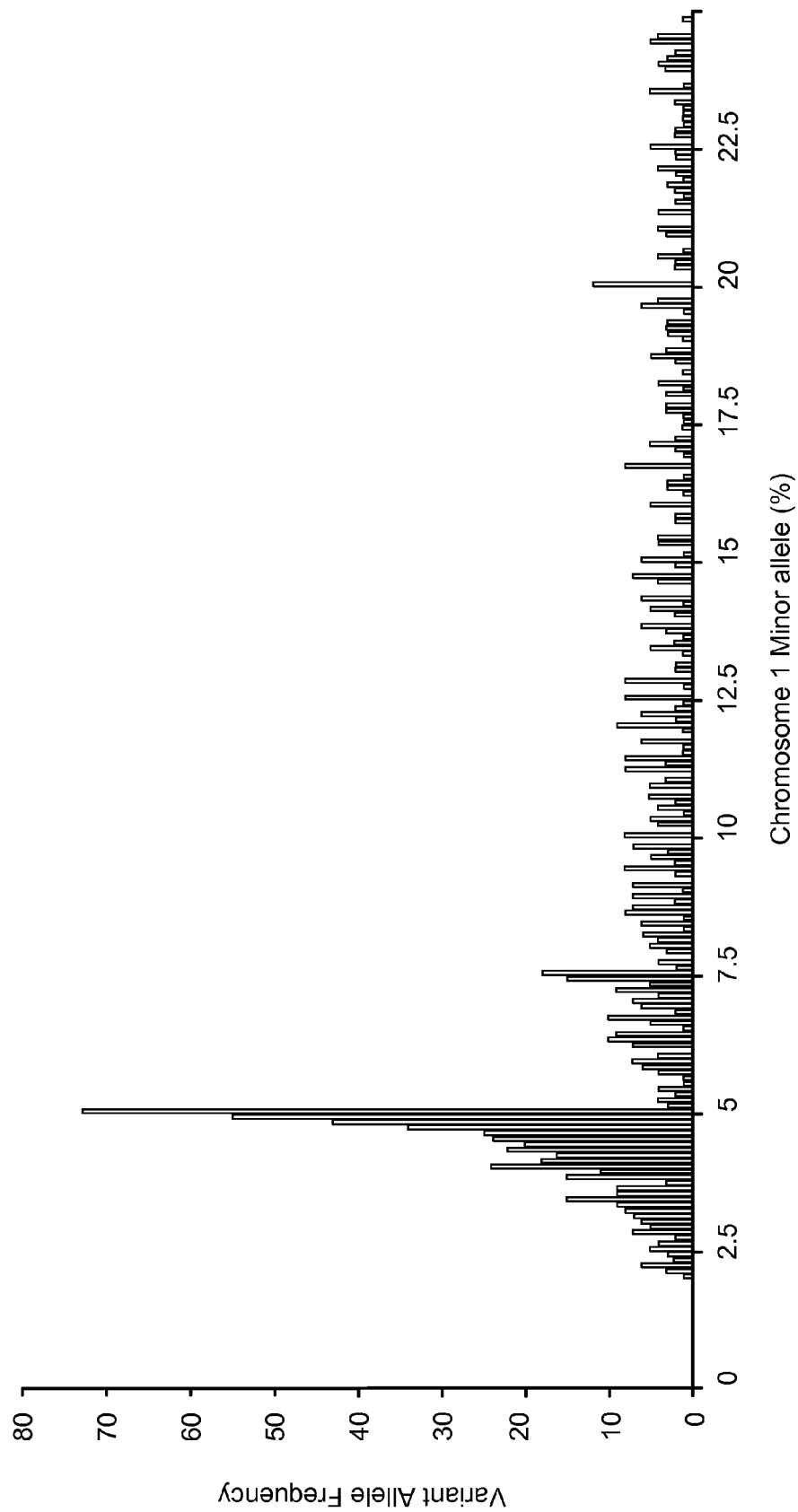

FIGS. 11 A and B show histograms of the number of variant base observations (Frequency) on chromosomes 1 and 7, respectively for minor allele percentages (A/D) for chromosomes 1 and 7. The percent minor allele is the percent of the total number of alleles at a given locus. For example, for a given locus at which there are 8 occurrences of minor allele A and 56 occurrences of major allele B, then the percent minor allele is 8%. The data show that the greatest number of occurrences (Frequency) for the minor allele are observed when the minor allele is present at 5%, which represents half of the fetal fraction. Accordingly, the data predicted that the sample contained a fetal fraction of 10%, which corresponds with that used to create the artificial maternal sample.

Figure 12A:
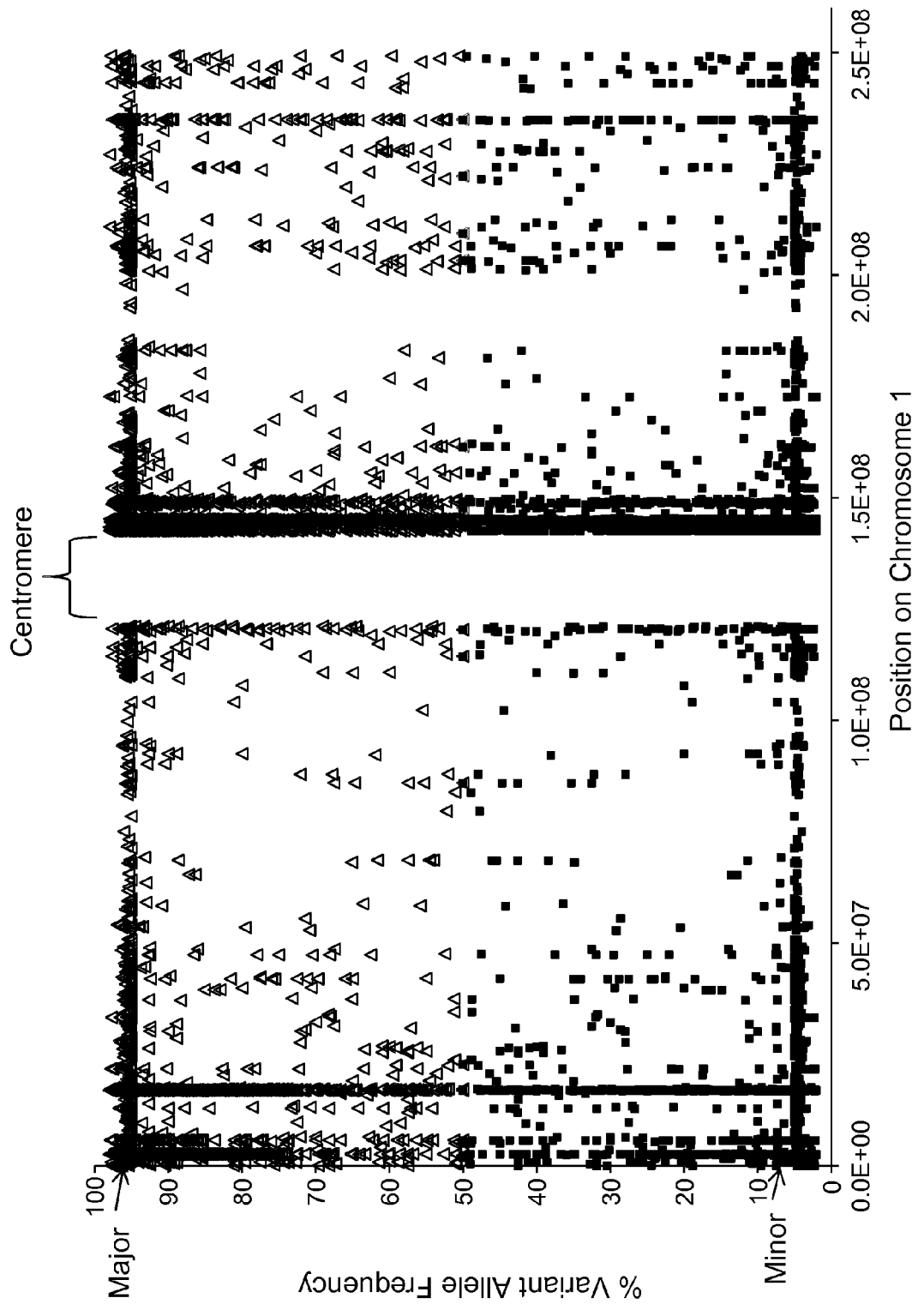
FIGS. 12A and B show the distribution of allelic frequency along chromosomes 1 (A) and chromosome 7.
Figure 12B:
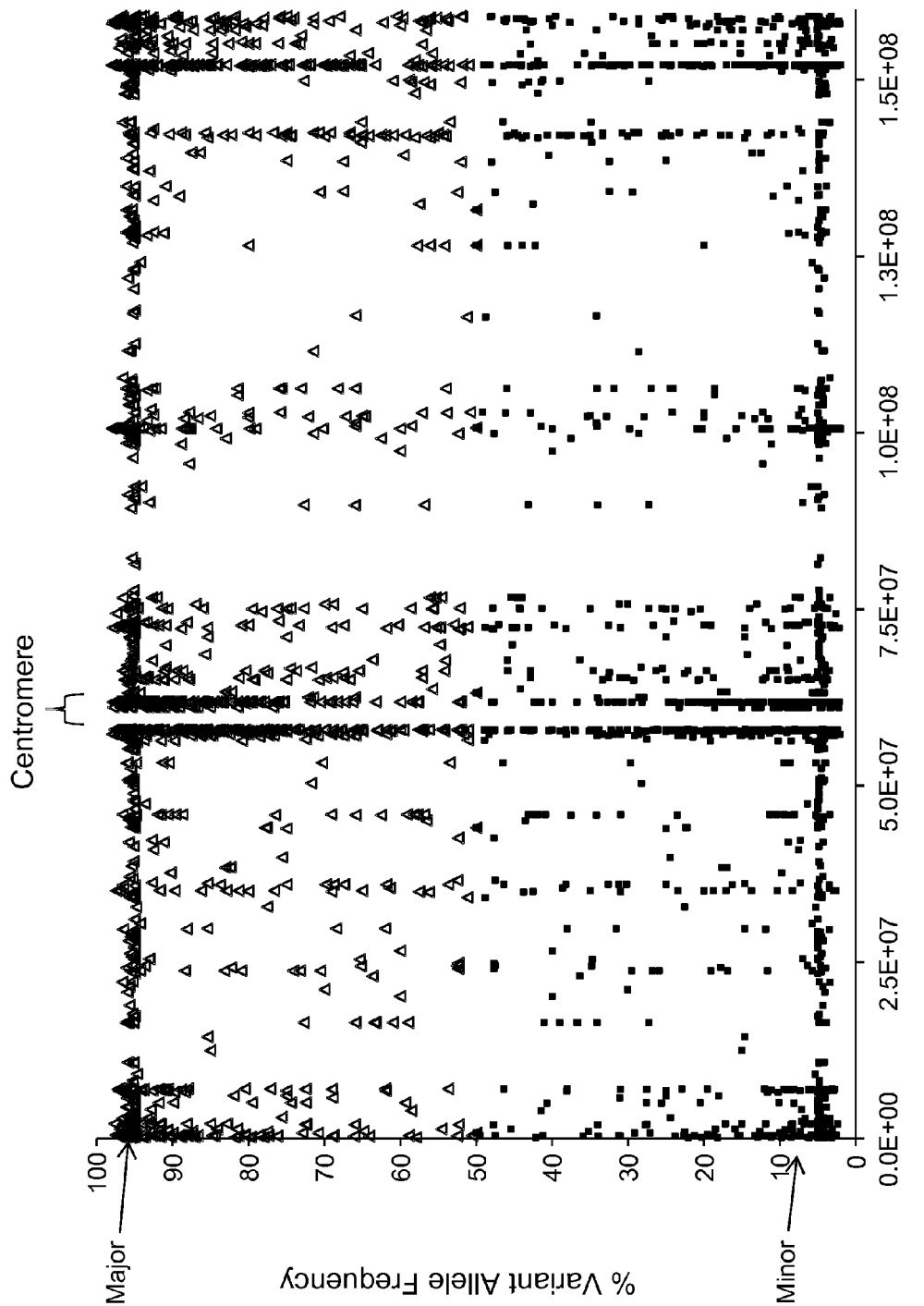

FIGS. 12A and B show the distribution of allelic frequency along chromosomes 1 and 7, respectively. Both plots show the maximum number of variant alleles along the chromosomes occur at minor allele frequency of 5% and major allele frequency of 95%. Some of the remaining data points represent biallelic loci present in the mother's genome, while others represent noise of the sequencing methodology. The central portion of each plot where variant alleles are not represented coincides with the chromosome's centromeres, which are known to be repeat-rich regions of chromosomes, to which tags map at more than one locus and are therefore excluded from the analysis. At other regions, for example regions flanking the centromere and regions corresponding to telomeres, variant alleles are over-represented. Over-representation of these regions can be attributed to the sequencing methodology whereby some regions are sequenced at greater levels than others.

Therefore, the present method can be used to predict fetal fraction. The method is particularly useful as it does not require identification of targeted sequences e.g. SNPs, and any variation at any position of any chromosome can serve to predict the percent fetal fraction.

Other Embodiments

Although the above has generally described the present invention according to specific processes and apparatus, the present invention has a much broader range of applicability. In particular, the present invention has been described in terms of detecting the fraction of fetal DNA in a DNA sample taken from a pregnant individual, but is not so limited, as the concepts and methods presented herein may also be applied in other contexts such as detecting the relative amounts of DNA types in a sample having DNA originating from two or more different genomes. Of course, those of ordinary skill in the art will recognize other variations, modifications, and alternatives.

For example, although most of the examples and applications described herein concern estimation of the fetal fraction of DNA in a DNA sample taken from an individual carrying a fetus, the invention is not so limited. More generally, various embodiments provide for assessing relative amounts of nucleic from two different genomes in a test sample that contains a mixture of nucleic acids from the two different genomes, and which are known or are suspected to differ in the amount of one or more sequence of interest. The mixture of nucleic acids is derived from two or more types of cells.

Further, although most of the examples presented herein concern samples taken from a pregnant human, the disclosure is not so limited. For example, the individual providing a sample to be tested can be an organism comprising polynucleotide sequences, e.g., a plant, an insect such as a fly, or an animal. In some embodiments, the subject is a mammal, e.g., a mouse, rat, dog, monkey or human. As indicted, the subject can be a pregnant individual. The subject might be an individual with a disease such as a cancer, or might be infected with a foreign body such as a microorganism, e.g., a virus. The sample can comprise a bodily fluid from the subject, e.g., blood, plasma, serum, sputum, saliva, urine, excrement, pus, lymph, mucous or the like. For example, the sample may be a maternal plasma sample containing a mixture of maternal and fetal cell free DNA. Generally, the disclosed methods may involve sequencing DNA from a sample; mapping the sequence reads to polymorphisms; classifying the polymorphisms on the basis of zygosity; and estimating the fraction of DNA from a secondary source in the sample.

What is claimed is:

1. A method of estimating a fraction of fetal DNA in DNA obtained from a bodily fluid of a pregnant individual carrying a fetus, the method comprising:
   (a) receiving a sample of the bodily fluid;
   (b) extracting DNA from the sample under conditions that extract DNA of both a maternal genome and a fetal genome present in the bodily fluid;
   (c) sequencing the extracted DNA with a nucleic acid sequencer under conditions that produce DNA sequence reads containing a plurality of polymorphisms;
   (d) mapping the DNA sequence reads to a plurality of polymorphism sites on a reference sequence corresponding to the plurality of polymorphisms, wherein the mapping is performed using a computational apparatus programmed to map nucleic acid sequences to polymorphism sites of the reference sequence;
   (e) determining allele frequencies of the mapped DNA sequence reads for the plurality of polymorphisms; and
   (f) estimating the fraction of fetal DNA in the extracted DNA, wherein the estimating comprises performing a calculation or calculations using the allele frequencies determined in (e) for polymorphisms of two or more of the following zygosity cases: (i) the pregnant individual is homozygous and the fetus is homozygous, (ii) the pregnant individual is homozygous and the fetus is heterozygous, (iii) the pregnant individual is heterozygous and the fetus is homozygous, and (iv) the pregnant individual is heterozygous and the fetus is heterozygous;

wherein (e)-(f) are performed on one or more processors running under program instructions for the determining and estimating.

2. The method of claim 1, wherein the allele frequencies for polymorphisms of two or more of the four zygosity cases in (f) comprise allele frequencies of polymorphisms in case (ii).

3. The method of claim 2, wherein the estimating of (f) comprises combining data of case (ii) and (iii) to calculate the fraction of fetal DNA.

4. The method of claim 3, wherein combining data of case (ii) and (iii) comprises transforming data of case (iii) to data of case (ii).

5. The method of claim 4, wherein combining data of case (ii) and (iii) to calculate the fraction of fetal DNA comprises applying regression techniques to the data of case (ii) and the transformed data of case (iii).

6. The method of claim 5, wherein the fraction of fetal DNA is estimated as twice the slope of a regression line of a linear regression model.

7. The method of claim 4, wherein transforming data of case (iii) to data of case (ii) comprises transforming data (D, A) to (D1, A1) as:

$$A1 = 0.5D - A$$

$$D1 = D$$

wherein D is the coverage of the polymorphism and A is the minor allele count of the polymorphism.

8. The method of claim 4, wherein transforming data of case (iii) to data of case (ii) comprises trigonometric transformation or use of rotation matrices.

9. The method of claim 3, wherein the fraction of fetal DNA is estimated as 2 A/D for case (ii) and as 1−2 A/D for case (iii), wherein A is the minor allele frequency and D is the coverage for the polymorphism in question.

10. The method of claim 1, wherein the estimating of (f) further comprises filtering the plurality of polymorphisms to remove from consideration any polymorphism among the plurality of polymorphisms having a minor allele frequency of greater than a defined threshold.

11. The method of claim 1, wherein the estimating of (f) further comprises filtering the plurality of polymorphisms to remove from consideration any polymorphism among the plurality of polymorphisms having a minor allele frequency of less than a defined threshold.

12. The method of claim 1, further comprising applying a threshold to the allele frequencies determined in (e) before the estimating in (f).

13. The method of claim 1, wherein the estimating of (f) further comprises applying the allele frequencies determined in (e) to a mixture model.

14. The method of claim 13, wherein the mixture model employs factorial moments to combine data from two or more of the four zygosity cases to calculate the fraction of fetal DNA.

15. The method of claim 14, wherein the factorial moments are calculated as:

$$F_1 = \frac{1}{n} \sum_{i=1}^{n} \frac{a_i}{d_i}$$

$$F_2 = \frac{1}{n} \sum_{i=1}^{n} \frac{a_i(a_i - 1)}{d_i(d_i - 1)}$$

$$\ldots$$

$$F_j = \frac{1}{n} \sum_{i=1}^{n} \frac{a_i(a_i - 1) \ldots (a_i - j + 1)}{d_i(d_i - 1)(d_i - j + 1)}$$

wherein $F_j$ is the $j^{th}$ factorial moment, $a_i$ is the minor allele frequency of the $i^{th}$ polymorphism, $d_i$ is the coverage of the $i^{th}$ polymorphism, and n is the number of polymorphisms.

16. The method of claim 15, further comprising calculating the fraction of fetal DNA based on the following relations between the factorial moments and probabilities of minor allele in zygosity cases:

$$F_1 \approx \sum_{i=1}^{m} \alpha_i p_i^1$$

$$F_2 \approx \sum_{i=1}^{m} \alpha_i p_i^2$$

$$\ldots$$

$$F_j \approx \sum_{i=1}^{m} \alpha_i p_i^j$$

$$\ldots$$

$$F_g \approx \sum_{i=1}^{m} \alpha_i p_i^g$$

wherein $\alpha_i$ is the portion of the plurality of polymorphisms in zygosity case i, $p_i$ is the binomial probability of the minor allele in zygosity case i, m is the number of zygosity cases, and g is the number of calculated factorial moments.

17. The method of claim 15, wherein the plurality of polymorphisms consists of polymorphisms in cases (i) and (ii), the method further comprising calculating the fraction of fetal DNA based on the following relations:

$$F_1 \approx \alpha_1 e + (1 - \alpha_1)\left(\frac{f}{2}\right)$$

$$F_2 \approx \alpha_1 e^2 + (1 - \alpha_1)\left(\frac{f}{2}\right)^2$$

$$F_3 \approx \alpha_1 e^3 + (1 - \alpha_1)\left(\frac{f}{2}\right)^3$$

wherein $F_1$, $F_2$, and $F_3$ are the first three factorial moments, $\alpha_1$ is the portion of the plurality of polymorphisms in zygosity case (i), e is an unknown sequencing error rate, and f is the fraction of fetal DNA.

18. The method of claim 15, wherein the plurality of polymorphisms consists of polymorphisms in cases (i) and (ii), the method further comprising calculating the fraction of fetal DNA based on the following relations:

$$F_1 \approx \alpha_1 e + (1 - \alpha_1)\left(\frac{f}{2}\right)$$

$$F_2 \approx \alpha_1 e^2 + (1 - \alpha_1)\left(\frac{f}{2}\right)^2$$

wherein $F_1$ and $F_2$ are the first two factorial moments, $\alpha_1$ is the portion of the plurality of polymorphisms in zygosity case (i), e is a known sequencing error rate, and f is the fraction of fetal DNA.

19. The method of claim 15, wherein the plurality of polymorphisms consists of polymorphisms in cases (i) and (ii), the method further comprising calculating the fraction of fetal DNA based on the following relations:

$$F_1 = \alpha_1 \frac{e}{4} + (1-\alpha_1)\left(e + \frac{f}{2}\right)$$

$$F_2 = \alpha_1 \left(\frac{e}{4}\right)^2 + (1-\alpha_1)\left(e + \frac{f}{2}\right)^2$$

wherein $F_1$ and $F_2$ are the first two factorial moments, $\alpha_1$ is the portion of the plurality of polymorphisms in zygosity case (i), e is a known sequencing error rate that is differentially applied to cases (i) and (ii), and f is the fraction of fetal DNA.

20. The method of claim 1, wherein the extracted DNA comprises cell-free DNA obtained from a plasma of the pregnant individual.

21. The method of claim 1, wherein the sequencing is conducted without selectively amplifying any of the plurality of polymorphisms.

22. The method of claim 1, further comprising executing program instructions on the one or more processors to automatically record the fraction of fetal DNA as estimated in (f) in a patient medical record, stored on a computer readable medium, for the pregnant individual.

23. The method of claim 22, wherein said patient medical record is maintained by a laboratory, physician's office, a hospital, a health maintenance organization, an insurance company, or a personal medical record website.

24. The method of claim 1, further comprising, based on the estimate of the fraction of fetal DNA, prescribing, initiating, and/or altering treatment of a human subject from whom the sample was taken.

25. The method of claim 1, further comprising, based on the estimate of the fraction of fetal DNA, ordering and/or performing one or more additional tests.

26. A method of estimating a fraction of fetal DNA in DNA obtained from a bodily fluid of a pregnant individual carrying a fetus, the method comprising:
 (a) receiving a sample of the bodily fluid;
 (b) extracting DNA from the sample under conditions that extract DNA of both a maternal genome and a fetal genome present in the bodily fluid;
 (c) sequencing the extracted DNA with a nucleic acid sequencer under conditions that produce DNA sequence reads;
 (d) identifying a plurality of biallelic polymorphisms for the DNA sequence reads, wherein the identifying is based on comparing the DNA sequence reads to a reference sequence or to each other using a computational apparatus programmed to compare nucleic acid sequences and identify polymorphisms;
 (e) determining allele frequencies of the DNA sequence reads for the plurality of biallelic polymorphisms; and
 (f) estimating the fraction of fetal DNA in the extracted DNA, wherein the estimating comprises performing a calculation or calculations using the allele frequencies determined in (e) for polymorphisms of two or more of the following zygosity cases: (i) the pregnant individual is homozygous and the fetus is homozygous, (ii) the pregnant individual is homozygous and the fetus is heterozygous, (iii) the pregnant individual is heterozygous and the fetus is homozygous, and (iv) the pregnant individual is heterozygous and the fetus is heterozygous;
 wherein (e)-(f) are performed on one or more processors running under program instructions for the determining and estimating.

27. The method of claim 26, wherein the calculation or calculations uses/use the allele frequencies determined in (e) for polymorphisms of zygosity case (ii).

28. The method of claim 26, wherein the estimating of (f) further comprises filtering the plurality of biallelic polymorphisms to remove from consideration any polymorphism having a minor allele frequency of greater than a defined threshold.

29. The method of claim 26, wherein the DNA sequence reads have a length of between about 20 base pairs and about 300 base pairs.

30. The method of claim 26, further comprising applying a threshold to the allele frequencies determined in (e) before the estimating in (f).

31. The method of claim 26, wherein the estimating of (f) further comprises applying the allele frequencies determined in (e) to a mixture model.

32. The method of claim 31, wherein the mixture model employs factorial moments.

33. The method of claim 26, wherein the extracted DNA comprises cell-free DNA obtained from the plasma of the pregnant individual.

34. The method of claim 26, wherein the estimating of (f) comprises combining data from case (ii) and (iii) to calculate the fraction of fetal DNA.

35. The method of claim 34, wherein combining data of case (ii) and (iii) comprises transforming data of case (iii) to data of case (ii).

36. The method of claim 1, wherein the estimating of (f) does not employ information obtained from cellular DNA of the pregnant individual.

37. The method of claim 1, wherein the estimating of (f) comprises combining the allele frequencies of the polymorphisms of the two or more zygosity cases.

38. The method of claim 26, wherein the estimating of (f) does not employ information obtained from cellular DNA of the pregnant individual.

39. The method of claim 26, wherein the estimating of (f) comprises combining the allele frequencies of the polymorphisms of the two or more zygosity cases.

* * * * *

SEQUENCE LISTING

```
<160> NUMBER OF SEQ ID NOS: 32

<210> SEQ ID NO 1
<211> LENGTH: 111
<212> TYPE: DNA
<213> ORGANISM: Homo sapiens

<400> SEQUENCE: 1
cacatgcaca gccagcaacc ctgtcagcag gagttcccac cagtttcttt ctgagaacat      60
ctgttcaggt ttctctccat ctctatttac tcaggtcaca ggaccttggg g              111

<210> SEQ ID NO 2
<211> LENGTH: 111
<212> TYPE: DNA
<213> ORGANISM: Homo sapiens

<400> SEQUENCE: 2
cacatgcaca gccagcaacc ctgtcagcag gagttcccac cagtttcttt ctgagaacat      60
ctgttcaggt ttctctccat ctctgtttac tcaggtcaca ggaccttggg g              111

<210> SEQ ID NO 3
<211> LENGTH: 126
<212> TYPE: DNA
<213> ORGANISM: Homo sapiens

<400> SEQUENCE: 3
tgaggaagtg aggctcagag ggtaagaaac tttgtcacag agctggtggt gagggtggag      60
attttacact ccctgcctcc cacaccagtt tctccagagt ggaaagactt tcatctcgca     120
ctggca                                                                126
```

<210> SEQ ID NO 4
<211> LENGTH: 126
<212> TYPE: DNA
<213> ORGANISM: Homo sapiens

<400> SEQUENCE: 4
tgaggaagtg aggctcagag ggtaagaaac tttgtcacag agctggtggt gagggtggag      60
attttacact ccctgcctcc cacaccagtt tctccggagt ggaaagactt tcatctcgca     120
ctggca                                                                126

<210> SEQ ID NO 5
<211> LENGTH: 121
<212> TYPE: DNA
<213> ORGANISM: Homo sapiens

<400> SEQUENCE: 5
gtgccttcag aacctttgag atctgattct attttttaaag cttcttagaa gagagattgc    60
aaagtgggtt gtttctctag ccagacaggg caggcaaata ggggtggctg gtgggatggg    120
a                                                                    121

<210> SEQ ID NO 6
<211> LENGTH: 121
<212> TYPE: DNA
<213> ORGANISM: Homo sapiens

<400> SEQUENCE: 6
gtgccttcag aacctttgag atctgattct attttttaaag cttcttagaa gagagattgc    60
aaagtgggtt gtttctctag ccagacaggg caggtaaata ggggtggctg gtgggatggg    120
a                                                                    121

<210> SEQ ID NO 7
<211> LENGTH: 111
<212> TYPE: DNA
<213> ORGANISM: Homo sapiens

<400> SEQUENCE: 7
aggtgtgtct ctcttttgtg aggggagggg tcccttctgg cctagtagag ggcctggcct     60
gcagtgagca ttcaaatcct caaggaacag ggtggggagg tgggacaaag g             111

<210> SEQ ID NO 8
<211> LENGTH: 111
<212> TYPE: DNA
<213> ORGANISM: Homo sapiens

<400> SEQUENCE: 8
aggtgtgtct ctcttttgtg aggggagggg tcccttctgg cctagtagag ggcctggcct     60
gcagtgagca ttcaaatcct cgaggaacag ggtggggagg tgggacaaag g             111

<210> SEQ ID NO 9
<211> LENGTH: 139
<212> TYPE: DNA
<213> ORGANISM: Homo sapiens

<400> SEQUENCE: 9
cctcgcctac tgtgctgttt ctaaccatca tgcttttccc tgaatctctt gagtcttttt     60
ctgctgtgga ctgaaacttg atcctgagat tcacctctag tccctctgag cagcctcctg    120

```
gaatactcag ctgggatgg                                              139

<210> SEQ ID NO 10
<211> LENGTH: 139
<212> TYPE: DNA
<213> ORGANISM: Homo sapiens

<400> SEQUENCE: 10
cctcgcctac tgtgctgttt ctaaccatca tgcttttccc tgaatctctt gagtcttttt    60
ctgctgtgga ctgaaacttg atcctgagat tcacctctag tccctctggg cagcctcctg   120
gaatactcag ctgggatgg                                              139

<210> SEQ ID NO 11
<211> LENGTH: 114
<212> TYPE: DNA
<213> ORGANISM: Homo sapiens

<400> SEQUENCE: 11
gcaactccct caactccaag gcagacacca aagccctccc tgcctgtggc tttgtagttc    60
tagtgtggga tctgactccc cacagcccac ccaaagccgg ggaactcctc actg         114

<210> SEQ ID NO 12
<211> LENGTH: 114
<212> TYPE: DNA
<213> ORGANISM: Homo sapiens

<400> SEQUENCE: 12
gcaactccct caactccaag gcagacacca aagccctccc tgcctgtggc tttgtagttc    60
tagtgtggga tctgactccc cacagcctac ccaaagccgg ggaactcctc actg         114

<210> SEQ ID NO 13
<211> LENGTH: 117
<212> TYPE: DNA
<213> ORGANISM: Homo sapiens

<400> SEQUENCE: 13
aattgcaatg gtgagaggtt gatggtaaaa tcaaacggaa cttgttattt tgtcattctg    60
atggactgga actgaggatt ttcaatttcc tctccaaccc aagacacttc tcactgg     117

<210> SEQ ID NO 14
<211> LENGTH: 117
<212> TYPE: DNA
<213> ORGANISM: Homo sapiens

<400> SEQUENCE: 14
aattgcaatg gtgagaggtt gatggtaaaa tcaaacggaa cttgttattt tgtcattctg    60
atggactgga actgaggatt ttcaatttcc tttccaaccc aagacacttc tcactgg     117

<210> SEQ ID NO 15
<211> LENGTH: 114
<212> TYPE: DNA
<213> ORGANISM: Homo sapiens

<400> SEQUENCE: 15
gaaatgcctt ctcaggtaat ggaaggttat ccaaatattt ttcgtaagta tttcaaatag    60
caatggctcg tctatggtta gtctcacagc cacattctca gaactgctca aacc         114

<210> SEQ ID NO 16
<211> LENGTH: 114
```

<212> TYPE: DNA
<213> ORGANISM: Homo sapiens

<400> SEQUENCE: 16

```
gaaatgcctt ctcaggtaat ggaaggttat ccaaatattt ttcgtaagta tttcaaatag    60
caatggctcg tctatggtta gtctcgcagc cacattctca gaactgctca aacc         114
```

<210> SEQ ID NO 17
<211> LENGTH: 128
<212> TYPE: DNA
<213> ORGANISM: Homo sapiens

<400> SEQUENCE: 17

```
acccaaaaca ctggaggggc ctcttctcat tttcggtaga ctgcaagtgt tagccgtcgg    60
gaccagcttc tgtctggaag ttcgtcaaat tgcagttaag tccaagtatg ccacatagca   120
gataaggg                                                            128
```

<210> SEQ ID NO 18
<211> LENGTH: 128
<212> TYPE: DNA
<213> ORGANISM: Homo sapiens

<400> SEQUENCE: 18

```
acccaaaaca ctggaggggc ctcttctcat tttcggtaga ctgcaagtgt tagccgtcgg    60
gaccagcttc tgtctggaag ttcgtcaaat tgcagttagg tccaagtatg ccacatagca   120
gataaggg                                                            128
```

<210> SEQ ID NO 19
<211> LENGTH: 110
<212> TYPE: DNA
<213> ORGANISM: Homo sapiens

<400> SEQUENCE: 19

```
gcaccagaat ttaaacaacg ctgacaataa atatgcagtc gatgatgact tcccagagct    60
ccagaagcaa ctccagcaca cagagaggcg ctgatgtgcc tgtcaggtgc              110
```

<210> SEQ ID NO 20
<211> LENGTH: 110
<212> TYPE: DNA
<213> ORGANISM: Homo sapiens

<400> SEQUENCE: 20

```
gcaccagaat ttaaacaacg ctgacaataa atatgcagtc gatgatgact tcccagagct    60
ccagaagcaa ctccagcaca cggagaggcg ctgatgtgcc tgtcaggtgc              110
```

<210> SEQ ID NO 21
<211> LENGTH: 139
<212> TYPE: DNA
<213> ORGANISM: Homo sapiens

<400> SEQUENCE: 21

```
gcccagatta gatggaacct tttcctcttt tccagtgcaa gacaagcgat tgaaagaagt    60
ggatgtgtta ttgcgggcac aatggagcca ctgaactgca gtgcaaaaat gcagtaaggc   120
atacagatag aagaaggag                                                139
```

<210> SEQ ID NO 22
<211> LENGTH: 139
<212> TYPE: DNA

<213> ORGANISM: Homo sapiens

<400> SEQUENCE: 22

| gcccagatta gatggaacct tttcctctttt tccagtgcaa gacaagcgat tgaaagaagt | 60 |
| ggatgtgtta ttgcgggcac aatggagcca ctgaactgca gtgcaaaaat gcagtaaggg | 120 |
| atacagatag aagaaggag | 139 |

<210> SEQ ID NO 23
<211> LENGTH: 116
<212> TYPE: DNA
<213> ORGANISM: Homo sapiens

<400> SEQUENCE: 23

| tgactgtata ccccaggtgc acccttgggt catctctatc atagaactta tctcacagag | 60 |
| tataagagct gatttctgtg tctgcctctc acactagact tccacatcct tagtgc | 116 |

<210> SEQ ID NO 24
<211> LENGTH: 116
<212> TYPE: DNA
<213> ORGANISM: Homo sapiens

<400> SEQUENCE: 24

| tgactgtata ccccaggtgc acccttgggt catctctatc atagaactta tctcacagag | 60 |
| tataagagct gatttctgtg tctgcctgtc acactagact tccacatcct tagtgc | 116 |

<210> SEQ ID NO 25
<211> LENGTH: 110
<212> TYPE: DNA
<213> ORGANISM: Homo sapiens

<400> SEQUENCE: 25

| tgtacgtggt caccagggga cgcctggcgc tgcgagggag gccccgagcc tcgtgccccc | 60 |
| gtgaagcttc agctcccctc cccggctgtc cttgaggctc ttctcacact | 110 |

<210> SEQ ID NO 26
<211> LENGTH: 110
<212> TYPE: DNA
<213> ORGANISM: Homo sapiens

<400> SEQUENCE: 26

| tgtacgtggt caccagggga cgcctggcgc tgcgagggag gccccgagcc tcgtgccccc | 60 |
| gtgaagcttc agctcccctc cctggctgtc cttgaggctc ttctcacact | 110 |

<210> SEQ ID NO 27
<211> LENGTH: 114
<212> TYPE: DNA
<213> ORGANISM: Homo sapiens

<400> SEQUENCE: 27

| cagtggaccc tgctgcacct ttcctcccct cccatcaacc tcttttgtgc ctcccccctcc | 60 |
| gtgtaccacc ttctctgtca ccaaccctgg cctcacaact ctctcctttg ccac | 114 |

<210> SEQ ID NO 28
<211> LENGTH: 114
<212> TYPE: DNA
<213> ORGANISM: Homo sapiens

<400> SEQUENCE: 28

| cagtggaccc tgctgcacct ttcctcccct cccatcaacc tcttttgtgc ctcccccctcc | 60 |

```
gtgtaccacc ttctctgtca ccacccctgg cctcacaact ctctcctttg ccac          114
```

<210> SEQ ID NO 29
<211> LENGTH: 110
<212> TYPE: DNA
<213> ORGANISM: Homo sapiens

<400> SEQUENCE: 29

```
cagtggcata gtagtccagg ggctcctcct cagcacctcc agcaccttcc aggaggcagc    60
agcgcaggca gagaacccgc tggaagaatc ggcggaagtt gtcggagagg              110
```

<210> SEQ ID NO 30
<211> LENGTH: 110
<212> TYPE: DNA
<213> ORGANISM: Homo sapiens

<400> SEQUENCE: 30

```
cagtggcata gtagtccagg ggctcctcct cagcacctcc agcaccttcc aggaggcagc    60
agcgcaggca gagaacccgc tggaaggatc ggcggaagtt gtcggagagg              110
```

<210> SEQ ID NO 31
<211> LENGTH: 140
<212> TYPE: DNA
<213> ORGANISM: Homo sapiens

<400> SEQUENCE: 31

```
gctgcagaat ccacagagcc agacgccccc tgggccccca gcgccccct gcacaagtgg     60 ggaaactagg tcatggggcc caggcagtgt ggaaggcgtt gcaggagttg cccagggcgt   120
ggggtcctcc agcctcagtg                                               140
```

<210> SEQ ID NO 32
<211> LENGTH: 140
<212> TYPE: DNA
<213> ORGANISM: Homo sapiens

<400> SEQUENCE: 32

```
gctgcagaat ccacagagcc agacgccccc tgggccccca gcgccccct gcacaagtgg     60 ggaaactagg tcatggggcc caggcagtgt ggaaggcgtt gcaggagttg cccagggtgt   120
ggggtcctcc agcctcagtg                                               140
```